US010201570B2

(12) United States Patent
Roth et al.

(10) Patent No.: US 10,201,570 B2
(45) Date of Patent: Feb. 12, 2019

(54) HALOGEN TREATMENT OF HEART ATTACK AND ISCHEMIC INJURY

(71) Applicant: Fred Hutchinson Cancer Research Center, Seattle, WA (US)

(72) Inventors: Mark B. Roth, Seattle, WA (US); Michael L. Morrison, Seattle, WA (US); Akiko Iwata, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 15/117,602

(22) PCT Filed: Feb. 10, 2015

(86) PCT No.: PCT/US2015/015227
§ 371 (c)(1),
(2) Date: Aug. 9, 2016

(87) PCT Pub. No.: WO2015/120458
PCT Pub. Date: Aug. 13, 2015

(65) Prior Publication Data
US 2016/0346323 A1    Dec. 1, 2016

Related U.S. Application Data

(60) Provisional application No. 62/082,957, filed on Nov. 21, 2014, provisional application No. 62/060,338, filed on Oct. 6, 2014, provisional application No. 62/007,015, filed on Jun. 3, 2014, provisional application No. 61/937,943, filed on Feb. 10, 2014.

(51) Int. Cl.
*A61K 33/18* (2006.01)
*A61K 38/06* (2006.01)
*A61K 9/00* (2006.01)
*A61K 33/00* (2006.01)
*A61K 33/04* (2006.01)
*A61K 33/16* (2006.01)

(52) U.S. Cl.
CPC ............ *A61K 33/18* (2013.01); *A61K 9/0053* (2013.01); *A61K 33/00* (2013.01); *A61K 33/04* (2013.01); *A61K 33/16* (2013.01); *A61K 38/063* (2013.01); *Y02A 50/481* (2018.01)

(58) Field of Classification Search
None
See application file for complete search history.

(56) References Cited

U.S. PATENT DOCUMENTS

| 5,492,742 | A  | 2/1996  | Zenner et al. |
| 6,458,758 | B1 | 10/2002 | Hsia |
| 7,745,150 | B2 | 6/2010  | Liang et al. |
| 8,680,151 | B2 | 3/2014  | Ruan et al. |
| 2005/0084447 | A1 | 4/2005 | Wei |
| 2007/0265223 | A1 | 11/2007 | Tomaselli et al. |
| 2009/0011051 | A1 | 1/2009 | Roth et al. |
| 2010/0021387 | A1 | 1/2010 | Roth et al. |

FOREIGN PATENT DOCUMENTS

| WO | WO 1995/018824 A1 | 7/1995 | |
| WO | WO 1996/002140 A1 | 2/1996 | |
| WO | WO 1997/026327 A1 | 7/1997 | |
| WO | WO 1998/034121 A2 | 8/1998 | |
| WO | WO 1999/021567 A1 | 5/1999 | |
| WO | WO-0224210 A2 * | 3/2002 | ............ A61K 33/00 |
| WO | WO 2002/060389 A2 | 8/2002 | |
| WO | WO 2005/039291 A2 | 5/2005 | |
| WO | WO 2005/041655 A1 | 5/2005 | |
| WO | WO 2005/041656 A2 | 5/2005 | |
| WO | WO 2006/113914 A2 | 10/2006 | |
| WO | WO 2007/124447 A2 | 11/2007 | |
| WO | WO 2008/040002 A2 | 4/2008 | |
| WO | WO 2008/043081 A2 | 4/2008 | |
| WO | WO 2008/079993 A2 | 7/2008 | |
| WO | WO 2008/089439 A2 | 7/2008 | |
| WO | WO 2008/157393 A1 | 12/2008 | |
| WO | WO 2009/003061 A1 | 12/2008 | |
| WO | WO 2010/045582 A2 | 4/2010 | |
| WO | WO 2010/090850 A1 | 8/2010 | |
| WO | WO 2013/003429 A1 | 1/2013 | |
| WO | WO 2013/149075 A1 | 10/2013 | |
| WO | WO-2013149075 A1 * | 10/2013 | ............... A61K 9/08 |
| WO | WO 2013/188528 A1 | 12/2013 | |
| WO | WO 2015/120458 A1 | 8/2015 | |

OTHER PUBLICATIONS

Alissa, E.M., "Antioxidants and Cardiovascular Diseases: A Summary of the Evidence." Journal of Cardiovascular Disease (2015); 3 (3): 347-356.
Bardia, et al., "Efficacy of Antioxidant Supplementation in Reducing Primary Cancer Incidence and Mortality: Systematic Review and Meta-analysis." Mayo Clinic Proc. (2008); 83 (1): 23-34.
Bjelakovic, et al., "Antioxidant supplements for prevention of gastrointestinal cancers: a systematic review and meta-analysis." Lancet (2004); 364 (9441): 1219-1228.
Delanty and Dichter, "Antioxidant Therapy in Neurologic Disease." Arch. Neurol. (2000); 57 (9): 1265-1270.
Filograna, et al., "Anti-Oxidants in Parkinson's Disease Therapy: A Critical Point of View." Current Neuropharmacology (2016); 14 (3): 260-271.
Ghezzi, et al., "The oxidative stress theory of disease: levels of evidence and epistemological aspects." British Journal of Pharmacology (2017); 174 (12): 1784-1796.

(Continued)

Primary Examiner — Michael P Cohen
(74) Attorney, Agent, or Firm — Cooley LLP

(57) ABSTRACT

The present invention relates to the use of halogen compounds, including iodide, and chalcogenide compounds, including iodide, sulfide and selenide, to treat and prevent diseases and injuries. The present invention further relates to compositions comprising a halogen compound and/or a chalcogenide compound, including pharmaceutical compositions, as well as methods of manufacturing such compounds and administering such compositions to subjects in need thereof.

8 Claims, 14 Drawing Sheets

(56) References Cited

OTHER PUBLICATIONS

Giustarini, et al., "Oxidative stress and human diseases: Origin, link, measurement, mechanisms, and biomarkers." Critical Reviews in Clinical Laboratory Sciences (2009); 46: (5-6): 241-281.

Mingsheng Luo and Tianhui Gao as chief editor, A Complete Collection of Pharmaceutical Necessities, Second Edition, Sichuan Science and Technology Press, Published on Jan. 2006 in Chengdu, p. 1341 (with English summary of pertinent portion), 3 pages.

Myung, et al., "Effects of antioxidant supplements on cancer prevention: meta-analysis of randomized controlled trials." Annals of Oncology (2010); 21 (1): 166-179.

Persson, et al., "Oxidative Stress in Alzheimer's Disease: Why Did Antioxidant Therapy Fail?" Oxidative Medicine and Cellular Longevity (2014); vol. 2014, Article ID 427318, 11 pages.

Singal, et al., "Antioxidants as Therapeutic Agents for Liver Disease." Liver Int. (2011); 31(10): 1432-1448.

Sugamura and Keaney Jr., "Reactive Oxygen Species in Cardiovascular Disease." Free Radic Biol Med. (2011); 51 (5): 978-992.

Warnholtz and Münzel, "Why do antioxidants fail to provide clinical benefit?" Curr Control Trials Cardiovasc Med (2000); 1 (1): 38-40.

PCT/US2015/015227, International Search Report and Written Opinion dated May 14, 2015, 14 pages.

PCT/US2015/015227, International Preliminary Report on Patentability dated Aug. 16, 2016, 11 pages.

EP 15746855.4, Extended European Search Report dated Sep. 6, 2017, 15 pages.

Anonymous, "Potassium Iodide (KI) Tabletsfor Radiation Protection—iOSAT by Anbex." Jan. 1, 2013, XP055401593, 2 pages, Retrieved from the Internet: URL:http://www.anbex.com/ [retrieved on Aug. 28, 2017].

Cann, S.A.H., "Hypothesis: Dietary Iodine Intake in the Etiology of Cardiovascular Disease." Journal of the American College of Nutrition (2006); 25(1): 1-11.

Curtis, M.J., et al., "Anion manipulation, a novel antiarrhythmic approach: mechanism of action." J Mol Cell Cardiol. (1993); 25(4): 417-436.

D'Alessandro, A., et al., "Red blood cell subpopulations in freshly drawn blood: application of proteomics and metabolomics to a decades-long biological issue." Blood Transfus. (2013); 11(1): 75-87.

Gao, Fen-Fei, et al., "Protective Effects of N-n-butyl Haloperidol Iodide on Myocardial Ischemia-Reperfusion Injury in Rabbits." Chinese Journal of Physiology (2004); 47(2): 61-66.

Iwata, A., et al., "Iodide Protects Heart Tissue from Reperfusion Injury." PLoS ONE (2014); 9(11): e112458.

Salmi, H., et al., "Change in plasma and erythrocyte thiol levels in children undergoing fasting studies for investigation of hypoglycaemia." Pediatric Endocrinology, Diabetes, and Metabolism (2011); 17(1): 14-19.

Senthil, S., et al., "Oxidative stress and antioxidants in patients with cardiogenic shock complicating acute myocardial infarction." Clinica Chimica Acta (2004); 348(1-2): 131-137.

Zhang, T., et al., "Perchlorate and Iodide in Whole Blood Samples from Infants, Children, and Adults in Nanchang, China." Environ. Sci. Technol. (2010); 44(18): 6947-6953.

\* cited by examiner

Figure 6 continued

Media:
RPMI/Hepes (Cl 100 mM)
Pen/Strep
L-Glutamine
10 % Human Serum

Incubation:       6 days
Start       02/21/13 Thursday
Pulse       02/26/13 Tuesday    (18 hours)
Harvest     02/27/13 Wednesday PBMC needed:

|   | no irrad | irrad.  |   | no irrad | irrad. |
|---|----------|---------|---|----------|--------|
| A | 0.3 Mio  | 0.3 Mio | B | 0.3 Mio  | 0.3 Mio |
| A | 1.2 Mio  |         | B |          | 1.2 Mio |
| A | 1.2 Mio  |         | B |          | 1.2 Mio |
| A |          | 1.2 Mio | B | 1.2 Mio  |        |
| A |          | 1.2 Mio | B | 1.2 Mio  |        |
| PBMC (Mio) | 2.7 | 2.7 |   | 2.7 | 2.7 |

Plate cells in 100 uL media (total). = each A or B: 50 uL, (4 ×10⁶/mL)

Add 100 ul media ± drug (2x)

<u>Premix (2X)</u>

| Drug | 2X concentration | 2 mL Premix |
|------|------------------|-------------|
| CSP (50 ug/mL -> 50 ng/uL) | 400 ng/mL | 800 ng= 16 µL |
| Iodide1 | 40 µg/mL |  |
| Iodide2 | 4 µg/mL | serial dilute 1:10 |
| Iodide3 | 0.4 µg/mL | serial dilute 1:10 |
| Selenide1 | 8 µg/mL |  |
| Selenide2 | 0.8 µg/mL | serial dilute 1:10 |
| Selenide3 | 0.08 µg/mL | serial dilute 1:10 |

Figure 7

| plate 1 | | | | |
|---|---|---|---|---|
| PBMC | Stimulator | Drug | Mean cpm (triplicate) | |
| A | 0 (Media) | 0 | 670 | neg. control |
| A | Ax | 0 | 497 | neg. control |
| A | Bx | 0 | 19395 | pos. control |
| A | Bx | CSA | 962 | |
| A | Bx | Iod (20 ug/mL) | 6344 | |
| A | Bx | Iod (2 ug/mL) | 64012 | |
| A | Bx | Iod (0.2 ug/mL) | 52145 | |
| A | Bx | Sel (4 ug/mL) | 234 | |
| A | Bx | Sel (0.4 ug/mL) | 248 | |
| A | Bx | Sel (0.04 ug/mL) | 182 | |
| B | Medium | 0 | 645 | neg. control |
| B | Bx | 0 | 1236 | neg. control |
| B | Ax | 0 | 35718 | pos. control |
| B | Ax | CSA | 625 | |
| B | Ax | Iod (20 ug/mL) | 12431 | |
| B | Ax | Iod (2 ug/mL) | 101335 | |
| B | Ax | Iod (0.2 ug/mL) | 93274 | |
| B | Ax | Sel (4 ug/mL) | 208 | |
| B | Ax | Sel (0.4 ug/mL) | 581 | |
| B | Ax | Sel (0.04 ug/mL) | 183 | |

Figure 7 continued plate 2

| PBMC | Stimulator | Drug | Mean cpm (triplicate) | |
|---|---|---|---|---|
| A | 0 (Media) | 0 | 467 | neg. control |
| A | Ax | 0 | 540 | neg. control |
| A | Bx | 0 | 16970 | pos. control |
| A | Bx | CSA | 574 | |
| A | Bx | Iod (20 ug/mL) | 7820 | |
| A | Bx | Iod (2 ug/mL) | 57632 | |
| A | Bx | Iod (0.2 ug/mL) | 32433 | |
| A | Bx | Sel (4 ug/mL) | 269 | |
| A | Bx | Sel (0.4 ug/mL) | 782 | |
| A | Bx | Sel (0.04 ug/mL) | 521 | |
| | | | | |
| B | Medium | 0 | 1196 | neg. control |
| B | Bx | 0 | 1245 | neg. control |
| B | Ax | 0 | 47188 | pos. control |
| B | Ax | CSA | 613 | |
| B | Ax | Iod (20 ug/mL) | 7084 | |
| B | Ax | Iod (2 ug/mL) | 99606 | |
| B | Ax | Iod (0.2 ug/mL) | 103191 | |
| B | Ax | Sel (4 ug/mL) | 246 | |
| B | Ax | Sel (0.4 ug/mL) | 571 | |
| B | Ax | Sel (0.04 ug/mL) | 1183 | |

HALOGEN TREATMENT OF HEART ATTACK AND ISCHEMIC INJURY

CROSS REFERENCE TO RELATED APPLICATIONS

This application claims priority to U.S. Provisional Application No. 61/937,943, filed on Feb. 10, 2014, U.S. Provisional Application No. 62/007,015, filed on Jun. 3, 2014, U.S. Provisional Application No. 62/060,338, filed on Oct. 6, 2014, and U.S. Provisional Application No. 62/082,957, filed on Nov. 21, 2014, each of which is incorporated by reference herein in its entirety.

GOVERNMENT INTEREST

This invention was made with government support under D12AP00008 awarded by the Department of the Interior. The government has certain rights in the invention.

FIELD OF THE INVENTION

This invention relates to compositions comprising halogen and/or chalcogenide compounds, including those comprising a halogen and/or a chalcogen compound in a reduced form, e.g. halides and/or chalcogenides, and methods for treating or preventing injuries and diseases, including diseases and injuries associated with hypoxia, ischemia or reperfusion injury and/or the formation of reactive oxygen species, e.g., heart attack, chronic heart failure, diseases and injuries associated with excessive metabolic rate, e.g., epilepsy, and diseases and injuries associated with an undesired immune or inflammatory response, e.g., graft versus host disease (GVHD) or organ transplant. The present invention also relates to methods for reducing or inhibiting an immune response, using a composition comprising a halide and/or a chalcogenide compound.

BACKGROUND OF THE INVENTION

Compounds containing a halogen element, i.e., those in Group 17 of the periodic table are commonly termed "halogens" or "halogen compounds." These elements are iodine (I), fluorine (F), chlorine (Cl), bromine (Br) and astatine (At). The artificially created element 117 (ununseptium) may also be a halogen. The term "halogen" means "salt-former," and compounds containing halogens are usually called "salts." All halogens have 7 electrons in their outer shells, giving them an oxidation number of −1. The halogens all form binary compounds with hydrogen known as the hydrogen halides: hydrogen fluoride (HF), hydrogen chloride (HCl), hydrogen bromide (HBr), hydrogen iodide (HI), and hydrogen astatide (HAt). When in aqueous solution, the hydrogen halides are known as hydrohalic acids. The names of these acids are as follows: hydrofluoric acid, hydrochloric acid, hydrobromic acid, and hydroiodic acid. Chlorine plays a biological role in higher animal life as aqueous chloride anions, which are included in the electrolyte makeup of inter- and intra-cellular fluids. Iodine is known to be needed by our bodies in trace amounts, particularly by the thyroid gland, and iron deficiency can cause goiter. The other three halogens have no known biological role.

In medicine, ischemia-reperfusion injuries are commonly associated with blood loss or reduced blood flow to a tissue or organ. Ischemia-reperfusion injury is a complex phenomenon often encountered when blood flow is restricted to an organ or tissue due to injury or blood loss, and also in surgical practice. Ischemia generally refers to a restriction in blood supply to tissues, causing a shortage of oxygen and glucose needed for cellular metabolism. Ischemia is generally caused by problems with blood vessels, with resultant damage to or dysfunction of tissue. It also refers to local anemia in a tissue or organ, which may result from injury or congestion (e.g., vasoconstriction, thrombosis or embolism). The consequences of such injury are local and remote tissue destruction, and sometimes death. Reperfusion refers generally to the restoration of blood flow to an ischemic tissue or organ. Primary reperfusion therapies, including primary percutaneous coronary intervention (PCI) and thrombolysis, are the standard of care for the treatment of acute coronary syndromes. Prompt restoration of blood flow to ischemic myocardium limits infarct size and reduces mortality. Unfortunately, however, the return of blood flow can also result in tissue, e.g., cardiac, damage and complications, referred to as reperfusion injury. Reperfusion injury is the tissue damage caused when blood supply returns to the tissue after a period of ischemia or lack of oxygen. The absence of oxygen and nutrients from blood during the ischemic period creates a condition in which the restoration of circulation results in inflammation and oxidative damage through the induction of oxidative stress rather than restoration of normal function. For example, in myocardial ischemia, considerable evidence attributes reactive oxygen species (ROS), produced either by the myocardium itself or by infiltrating inflammatory cells, as an early event in this process. Once produced, ROS can lead to cellular damage through a number of pathways including direct damage to membranes and proteins or indirect damage through the activation of pro-apoptotic pathways.

Effective therapies to reduce or prevent ischemic and reperfusion injuries have proven elusive. Despite an improved understanding of the pathophysiology of these processes and encouraging preclinical trials of multiple agents, most of the clinical trials to prevent ischemia-reperfusion injury have been disappointing. Accordingly, therapies for treating or limiting injuries and damage resulting from hypoxia, ischemia and/or reperfusion remain an active area of investigation.

Clearly, there is a need in the art for new pharmaceutical compositions and methods for treating or preventing ischemic and/or reperfusion injuries, e.g., including those that may be conveniently administered to patients, both in a controlled medical environment e.g., for treatment of disease, as a treatment in the field during an emergency, or in critical care in response to a catastrophic injury or life-threatening medical event. The present invention meets this need by providing pharmaceutical compositions comprising active agents, which are demonstrated herein to protect animals from injury resulting from hypoxic and/or ischemic conditions, as well as other injuries and disease conditions.

BRIEF SUMMARY OF THE INVENTION

The present invention provides compositions and methods useful in treating or preventing a variety of diseases, conditions, and disorders.

In one embodiment, the present invention provides a method for treating or preventing an injury or disease in a subject, comprising providing to said subject a composition comprising a halogen compound and a pharmaceutically acceptable carrier, diluent, or excipient. In certain embodiments, the halogen compound is in a chemically reduced form. In certain embodiments, the halogen compound comprises iodine, bromine, chlorine, fluorine, or astatine. In particular embodiments wherein the halogen compound comprises iodine, said halogen compound is an iodide. In various embodiments, the iodide is sodium iodide, potassium iodide, hydrogen iodide, calcium iodide, or silver iodide. In particular embodiments, the halogen compound is an iodate. In various embodiments, the iodate is sodium iodate, potassium iodate, calcium iodate, or silver iodate. In certain embodiments, the halogen compound comprises bromine. In particular embodiments wherein the halogen compound comprises a bromine, the halogen compound is a bromide. In certain embodiments, the halogen is present in the halogen compound in a reduced form.

In certain embodiments of the present invention, the composition comprises one or more reducing agents or antioxidants. In particular embodiments, the composition is formulated to maintain the halogen or halogen compound present in the composition in a reduced state, e.g., to maintain iodide in its −1 oxidation state. In one embodiment, the composition is a pharmaceutical composition, comprising a reduced form of a halogen compound, e.g., a reduced form of iodine, such as iodide, glutathione, and a pharmaceutically acceptable carrier, diluent, or excipient. In certain embodiments, the glutathione is present in an amount sufficient to maintain the halogen or halogen compound in its reduced state. In certain embodiments of methods and composition of the present invention, at least 90% of the reduced form of halogen or halogen compound in the composition remains in a reduced form for at least one hour, at least one week, at least one month, or at least six months when stored at room temperature. In certain embodiments, at least 90% of the reduced form of halogen or halogen compound in the composition is present in a reduced form for at least one month, at least two months, at least four months, at least six months, or at least one year when stored at about 4° C. In particular embodiments, at least 50%, at least 75%, or at least 90% of the glutathione initially present in the composition is in a reduced form.

In various embodiments of methods of the present invention, the composition is provided to the subject parenterally or orally. In certain embodiments, the composition is provided to the subject intravenously or by infusion.

In certain embodiments, the composition is formulated for oral administration, and the composition comprises a stable reduced form of the halogen compound.

In particular embodiments, the composition is formulated for intravenous administration or administration by infusion, and the composition comprises a stable reduced form of the halogen compound.

In various embodiments, the composition is provided to the subject in an amount sufficient to increase the blood concentration of the halogen at least 100%, at least 200%, at least 300%, at least 400%, or at least 500% for at least some time.

In various embodiments, the disease or injury is selected from any of the following, or is caused by or results from any of the following: ablation therapy, adrenalectomy, aortic aneurysm, aortic root surgery, aortic stenosis, aortic valve disease, arrhythmia, atherosclerosis, atrial flutter, atrial fibrillation, atrial septal defect, arteriovenous malformation, awake brain surgery, bariatric surgery, bone marrow transplant, brachial plexus injuries, bradycardia, brain aneuryism, breast augmentation surgery, breast reduction surgery, burn injury, coronary bypass surgery, coronary artery disease, cardiac ablation, cardiac catheterization, cardiac resynchronization therapy, cardiac surgery, cardiomyopathy, cardiac surgery, cardiovascular diseases, carotid angioplasty and stenting, coarctation of the aorta, congenital heart disease, coronary bypass surgery, coronary artery disease, critical care medicine, chronic obstructive pulmonary disease, elbow replacement surgery, emergency medicine, general internal medicine, general surgery, gastrointestinal bleeding, heart attack, heart transplant, heart valve surgery, hip replacement surgery, hypertrophic cardiomyopathy, hypoxia ischemia encephalopathy, hysterectomy, ileoanal anastomosis (j pouch) surgery, inflammatory bowel disease, ischemic heart disease, ischemia reperfusion injury, irritable bowel syndrome, jaw surgery, kidney transplant, laryngotracheal reconstruction surgery, liver transplant, lung volume reduction surgery, lung transplant, minimally invasive heart surgery, neurosurgery, oral and maxillofacial surgery, orthopedic surgery, pancreas transplant, pancreatitis, partial nephrectomy, pediatric cervical spine surgery, pediatric surgery, pelvic organ prolapse, plastic and reconstructive surgery, pulmonary and critical care medicine, pulmonary atresia, pulmonary vein isolation, rectal prolapse, restrictive cardiomyopathy, retinal detachment, retinopathy of prematurity, robotic surgery, spinal cord injury, spontaneous coronary artery dissection, spontaneous occlusion of the circle of willis, stroke, stroke telemedicine (telestroke), sudden cardiac arrest, stereotactic radiosurgery, surgery, systolic heart failure, chronic heart failure, tachycardia, teare's disease, thoracic aortic aneurysm, thoracic surgery, total elbow arthroplasty, tricuspid valve disease, ulcerative colitis, valve-preserving aortic root repair, vascular and endovascular surgery, vascular medicine, or ventricular tachycardia. In certain embodiments, the injury or disease is selected from, results from or is caused by inflammation, heart attack, coronary bypass surgery, ischemia, gut ischemia, liver ischemia, kidney ischemia, hypoxic-ischemic encephalopathy, stroke, traumatic brain injury, limb ischemia, eye ischemia, sepsis, smoke, burn, reperfusion, or acute lung injury. In certain embodiments, the injury is an infarct caused by a heart attack or a stroke. In certain embodiments, the disease is hypoxic-ischemic encephalopathy. In particular embodiments, the injury is a medical procedure, such as e.g., a cell, tissue or organ transplantation, or results from a medical procedure, such as, e.g., transplant rejection. In certain embodiments, the injury is an autologous or heterologous transplantation, e.g., of cells, tissue or an organ. In certain embodiments, the injury is a coronary bypass surgery, optionally a coronary artery bypass graft (CABG).

Certain embodiments of methods of the present invention comprise providing to the subject a composition comprising a halogen compound and a composition comprising one or more additional active agent. In certain embodiments, a single composition comprises both the halogen compound and the one or more additional active agent, whereas in other embodiments, the halogen and the one or more additional active agent are present in separate compositions. In particular embodiments, compositions of the present invention comprise a halogen compound and/or one or more additional active agents, and a pharmaceutically acceptable carrier, diluent, or excipient. In particular embodiments, compositions of the present invention are pharmaceutical compositions. In particular embodiments, the invention includes a composition comprising a halogen compound, optionally in a reduced form, one or more additional active agent, and a pharmaceutically acceptable carrier, diluent, or excipient. In particular embodiments, the one or more additional active agent comprises a chalcogenide, optionally in a reduced form. In particular embodiments, the chalcogenide comprises sulfide or selenide. In particular embodiments, the sulfide or selenide is a reduced form of sulfide or selenide. In some embodiments, the reduced form of sulfide is present in a stable liquid pharmaceutical composition comprising a pharmaceutically acceptable carrier, diluent, or excipient. In certain embodiments, the composition comprises both a halogen compound and a chalcogenide, wherein the composition is formulated for intravenous or oral administration.

In particular embodiments of methods of the present invention, the composition comprises a carrier. In certain embodiments, the halogen compound is associated with the carrier. In certain embodiments where the composition comprises a halogen compound and one or more additional active agents, the halogen compound and the one or more additional active agent are associated with the carrier. In certain embodiments, the halogen compound and the one or more additional active agent present in the composition are associated with the carrier covalently or non-covalently. In particular embodiments, the carrier is albumin, plasma, serum, alpha-2-macroglobulin, or immunoglobulin, or a polypeptide related to any of these polypeptides.

In a related embodiment, the present invention provides a composition comprising a halogen compound and a carrier, wherein said halogen compound is associated to the carrier. In certain embodiments, the composition further comprises one or more additional active agents. In particular embodiments, the one or more additional active agents are associated with the carrier. In certain embodiments, said halogen compound and/or said one or more additional active agent are associated with the carrier covalently or non-covalently. In certain embodiments, the one or more additional active agent comprises a chalcogenide. In particular embodiments, the chalcogenide comprises sulfide or selenide. In further embodiments, the sulfide or selenide is a reduced form of sulfide or selenide.

In another related embodiments, the present invention includes a composition comprising a stable reduced form of a halogen compound, wherein said pharmaceutical composition is formulated for intravenous administration, administration by infusion, or oral administration. In particular embodiments, the halogen compound comprises iodine, bromine, chlorine, fluorine, or astatine. In certain embodiments, the halogen compound comprises iodine. In particular embodiments, the halogen compound is an iodide, an iodate, an organoiodide, a periodate, or a periodinane. In certain embodiments, the iodide is sodium iodide, potassium iodide, hydrogen iodide, calcium iodide, zinc iodide, or silver iodide. In certain embodiments, the iodate is sodium iodate, potassium iodate, calcium iodate, or silver iodate. In particular embodiments, the halogen compound comprises bromine. In certain embodiments, the halogen compound is a bromide. In particular embodiments, the composition comprises glutathione.

In certain embodiments of methods and composition of the present invention, at least 90% of the halogen compound in the composition is present in a reduced form for at least one hour, at least one week, at least one month, or at least six months when stored at room temperature. In certain embodiments, at least 90% of the halogen compound in the composition is present in a reduced form for at least one month, at least two months, at least four months, at least six months, or at least one year when stored at about 4° C.

In certain embodiments of methods and compositions of the present invention, the composition comprising the halogen compound and/or the composition comprising the additional active agent comprises one or more of a reducing agent, a tonicity agent, a stabilizer, a surfactant, a lycoprotectant, a polyol, an antioxidant, or a preservative.

In related embodiments, the present invention includes a unit dosage form of a composition of the invention, wherein said unit dosage form is formulated for oral administration. In particular embodiments, the unit dosage form is a pill, tablet, caplet or capsule. In certain embodiments, the unit dosage form comprises less than or equal to 150 mg, less than or equal to 125 mg, less than or equal to 100 mg, less than or equal to 75 mg, less than or equal to 50 mg, less than or equal to 25 mg, or less than or equal to 10 mg of the halogen compound. In certain embodiments, the unit dosage form comprises between about 1 mg and about 150 mg (including any interval in this range), between about 1 mg and about 125 mg, between about 1 mg and about 100 mg, between about 1 mg and about 75 mg, between about 1 mg and about 50 mg, between about 1 mg and about 25 mg or between about 1 mg and about 10 mg of the halogen compound. In certain embodiments, the unit dosage form comprises about 150 mg, about 125 mg, about 100 mg, about 75 mg, about 50 mg, about 25 mg or about about 10 mg of the halogen compound. In certain embodiments, the unit dosage form comprises less than or equal to 1000 mg, less than or equal to 800 mg, less than or equal to 700 mg, less than or equal to 500 mg, less than or equal to 250 mg, less than or equal to 200 mg, or less than or equal to 150 mg of the halogen compound. In certain embodiments, the unit dosage form comprises between about 100 mg and about 1000 mg (including any interval in this range), between about 150 mg and about 800 mg, between about 200 mg and about 700 mg, between about 250 mg and about 600 mg, between about 300 mg and about 500 mg, between about 350 mg and about 450 mg or between about 300 mg and about 700 mg of the halogen compound. In certain embodiments, the unit dosage form comprises about 200 mg, about 300 mg, about 400 mg, about 500 mg, about 600 mg, about 700 mg, about 800 mg, about 900 mg, or about about 1000 mg of the halogen compound. In certain embodiments, the unit dosage form comprises or contains an amount of halogen compound and/or chalcogen compound to achieve an effective dose when one or more of the unit dosage form is provided to a subject, e.g., a mammal, such as a human. For example, one or more, two or more, or four or more, unit dosage forms may be provided to the subject in one day to achieve an effective amount. In particular embodiments, the halogen compound comprises iodine, bromine, chlorine, fluorine, or astatine. In certain embodiments, the halogen compound comprises iodine. In certain embodiments, the halogen compound is an iodide, an iodate, an organoiodide, a periodate, or a periodinane. In certain embodiments, the halogen compound is an iodide. In certain embodiments, the iodide is sodium iodide, potassium iodide, hydrogen iodide, calcium iodide, or silver iodide. In certain embodiments, the halogen compound is an iodate. In certain embodiments, the iodate is sodium iodate, potassium iodate, calcium iodate, or silver iodate. In certain embodiments, the halogen compound comprises bromine. In certain embodiments, the halogen compound is a bromide.

In particular embodiments, the unit dosage form further comprises one or more additional active agent. In certain embodiments, the one or more additional active agent comprises a chalcogenide. In certain embodiments, the chalcogenide comprises sulfide or selenide. In certain embodiments, the sulfide or selenide is a reduced form of sulfide or selenide.

The present invention further includes a method of treating or preventing an injury or disease in a subject, comprising providing to said subject any of the unit dosage forms of the present invention. In particular embodiments, the disease or injury is any of those described herein. In certain embodiments, the injury is an infarct caused by a heart attack or a stroke. In certain embodiments, the disease is chronic heart failure, e.g., systolic heart failure. In certain embodiments, the injury is caused by coronary bypass surgery, optionally a coronary artery bypass graft (CABG).

In certain embodiments of any of the methods of the present invention, the method further comprises providing to the subject a composition comprising a goitrogen, a compound that inhibits or impedes thyroid hormone production or activity, or glutathione. In particular embodiment, the one or more additional active agent comprises glutathione. In certain embodiments, at least 50%, at least 75%, or at least 90% of the glutathione provided is in a reduced state.

In certain embodiments, any of the compositions of the present invention further comprises one or more additional active agents. In certain embodiments, the one or more additional active agent comprises a goitrogen, a compound that inhibits or impedes thyroid hormone production or activity, or glutathione. In particular embodiment, the one or more additional active agent comprises glutathione. In certain embodiments, at least 50%, at least 75%, or at least 90% of the glutathione provided is in a reduced state.

In particular embodiments of the methods and compositions of the invention, the goitrogen, compound that inhibits or impedes thyroid hormone production or activity, or glutathione is associated with the carrier.

In certain embodiments, the present invention includes a method for treating or preventing an injury or disease in a subject, comprising providing to said subject a composition comprising a chalcogenide and glutathione, or comprising a halogen compound and glutathione, wherein said composition further comprises a pharmaceutically acceptable carrier, diluent, or excipient. In certain embodiments, the composition further comprises a halogen compound or a chalcogenide, respectively. In certain embodiments, the composition comprises a halogen compound, a chalcogenide, and glutathione. In certain embodiments, the halogen compound comprises iodine, e.g., iodide or iodate. In certain embodiments, the chalcogenide comprises selenide or sulfide, including e.g., reduced forms of either or both sulfide and selenide. In certain embodiments, the disease or injury is any of those described herein. In particular embodiments, the injury or disease is selected from, results from or is caused by inflammation, heart attack, chronic heart failure, coronary bypass surgery, ischemia, gut ischemia, liver ischemia, kidney ischemia, hypoxic-ischemic encephalopathy, stroke, traumatic brain injury, limb ischemia, eye ischemia, sepsis, smoke, burn, reperfusion, or acute lung injury. In one embodiment, the injury is an infarct caused by a heart attack or a stroke. In one embodiment, the injury is caused by coronary bypass surgery, optionally a coronary artery bypass graft (CABG).

In various embodiments of any of the methods of the invention, about 1 pg/kg to about 1 g/kg of chalcogenide, sulfide, and/or selenide is provided to the subject. In certain embodiments, about 10 µg/kg to about 10 mg/kg of chalcogenide, e.g., sulfide or selenide, is provided to the subject. In certain embodiments of any of the methods of the invention, the halogen compound is iodide, iodate, or iodine, and about 10 pg/kg to about 1 g/kg of iodide, iodate, or iodine is provided to the subject. In particular embodiments, about 10 µg/kg to about 10 mg/kg, about 100 µg/kg to about 10 mg/kg, about 1 mg/kg to about 10 mg/kg, about 1 mg/kg to about 5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg of iodide, iodate, or iodine is provided to the subject. In certain embodiments, any of these amounts are provided to the subject within about 24 hours or within about 48 hours, e.g., daily or every other day, for a duration of time, e.g., for one day, two days, three days, four days, five days, six days, one week, two weeks, one month, two months, six months, one year, or longer.

In certain embodiments, the amount of halogen compound, e.g., iodide, iodate, or iodine, provided to the subject, e.g., a mammal or human, is less than or equal to 150 mg, less than or equal to 125 mg, less than or equal to 100 mg, less than or equal to 75 mg, less than or equal to 50 mg, less than or equal to 25 mg, or less than or equal to 10 mg of the halogen compound. In certain embodiments, the amount of halogen compound provided to the subject comprises between about 1 mg and about 150 mg (including any interval in this range), between about 1 mg and about 125 mg, between about 1 mg and about 100 mg, between about 1 mg and about 75 mg, between about 1 mg and about 50 mg, between about 1 mg and about 25 mg or between about 1 mg and about 10 mg of the halogen compound. In certain embodiments, the amount of halogen compound provided to the subject is about 150 mg, about 125 mg, about 100 mg, about 75 mg, about 50 mg, about 25 mg or about 10 mg of the halogen compound. In certain embodiments, the amount of halogen compound provided to the subject is less than or equal to 1000 mg, less than or equal to 800 mg, less than or equal to 700 mg, less than or equal to 500 mg, less than or equal to 250 mg, less than or equal to 200 mg, or less than or equal to 150 mg of the halogen compound. In certain embodiments, the amount of halogen compound provided to the subject comprises between about 100 mg and about 1000 mg (including any interval in this range), between about 150 mg and about 800 mg, between about 200 mg and about 700 mg, between about 250 mg and about 600 mg, between about 300 mg and about 500 mg, between about 350 mg and about 450 mg or between about 300 mg and about 700 mg of the halogen compound. In certain embodiments, the amount of halogen compound provided to the subject is about 200 mg, about 300 mg, about 400 mg, about 500 mg, about 600 mg, about 700 mg, about 800 mg, about 900 mg, or about about 1000 mg of the halogen compound. In certain embodiments, any of these amounts are provided to the subject within about 24 hours or about 48 hours, e.g., daily or every other day, for a duration of time, e.g., for one day, two days, three days, four days, five days, six days, one week, two weeks, one month, two months, six months, one year, or longer.

In various embodiments of any of the methods and composition of the invention, the composition comprises about 1.5 µM to about 500 mM glutathione. In particular embodiments, the composition comprises about 15 mM to about 500 mM glutathione.

In a further embodiment, the present invention comprises a composition comprising a chalcogenide and glutathione, or a halogen compound and glutathione, wherein said composition further comprises a pharmaceutically acceptable carrier, diluent, or excipient. In particular embodiments, the composition further comprises a halogen compound or a chalcogenide, respectively. In certain embodiments, the composition comprises a halogen compound, a chalcogenide, and glutathione. In particular embodiments, the halogen compound comprises iodine, e.g., iodide. In particular embodiments, the chalcogenide comprises selenide or sulfide, e.g., a reduced form of either or both selenide and sulfide. In certain embodiments, glutathione is present in the composition at about 1 mM to about 500 mM. In certain embodiments, the composition is stored in a reduced oxygen or oxygen-free environment prior to and/or while being provided to the subject. In certain embodiments, the composition is stored in said environment under argon or nitrogen prior to being provided to the subject. In certain embodiments, the composition is formulated for parenteral or oral administration. In certain embodiments, the composition is formulated for intravenous administration or administration by infusion.

In another related embodiment, the present invention includes a method for treating or preventing a disease or injury in a subject, comprising inhibiting or preventing a decrease in the ratio of the amount of reduced glutathione to the amount of oxidized glutathione in the subject's bloodstream or at the site of disease or injury. In certain embodiments, the method comprises increasing the ratio of the amount of reduced glutathione to the amount of oxidized glutathione in the subject's bloodstream or at the site of disease or injury. In particular embodiments, the method comprises providing a halogen compound and/or a chalcogenide systemically to the subject prior to, at the time of, or after onset of said disease or injury. In certain embodiments, the halogen compound comprises iodine. In particular embodiments, the halogen compound is an iodide or iodate. In certain embodiments, the chalcogenide comprises sulfur or selenium. In particular embodiments, the chalcogenide comprises selenide. In certain embodiments, the halogen compound and/or the chalcogenide is delivered to the subject orally or intravenously or by infusion. In certain embodiments, the halogen compound and/or the chalcogenide are delivered to the subject at a site remote from said disease or injury. In certain embodiments, the disease or injury is localized within a certain tissue or organ. In certain embodiments, the disease or injury is localized within a cell type, tissue or organ. In certain embodiments, the method is used to treat or prevent sickle cell crisis or sickle cell anemia. In certain embodiments, the method is used to treat or prevent blood attack. In certain embodiments, the method is used to treat or prevent myocardial infarction or cardiogenic shock. In certain embodiments, the method is used to treat or prevent heart attack or chronic heart failure. In certain embodiments, the method is used to treat or prevent contrast-induced nephropathy.

In a further embodiment, the present invention provides a method of preventing, inhibiting, or reducing an immune response in a subject, comprising providing a halogen compound and/or a chalcogenide to the subject. In particular embodiments, the halogen compound comprises iodine. In certain embodiments, the halogen compound is an iodide. In certain embodiments, the chalcogenide comprises sulfur or selenium. In certain embodiments, chalcogenide comprises selenide. In particular embodiments, the halogen compound and/or the chalcogenide is delivered to the subject orally or intravenously or by infusion. In certain embodiments, the halogen compound and/or the chalcogenide are delivered to the subject at a site of inflammation or immune reaction. In certain embodiments, the method is used to treat or prevent graft versus host disease. In certain embodiments, the method is used to inhibit or reduce an immune response during or following cell, tissue or organ transplantation. In particular embodiments of any methods related to cell, tissue or organ transplantation, the cell, tissue or organ is allogeneic or autologous to the transplant recipient. In certain embodiments, the method is used to treat or prevent ischemic or reperfusion injury. In certain embodiments, the method reduces the amount of one or more reactive oxygen species in the subject's bloodstream or at a site of inflammation or immune reaction within the subject.

In certain embodiments, a goitrogen is used instead of or in addition to a chalcogenide or a halogen compound in the compositions and methods of the invention.

or 150 mM GSH (FIG. 5B) over the eight minutes immediately following preparation. The oxidized forms of selenide appear dark in the solutions, with the samples in glutathione clearly showing reduced levels of oxidation at each time point.

Figure 6:
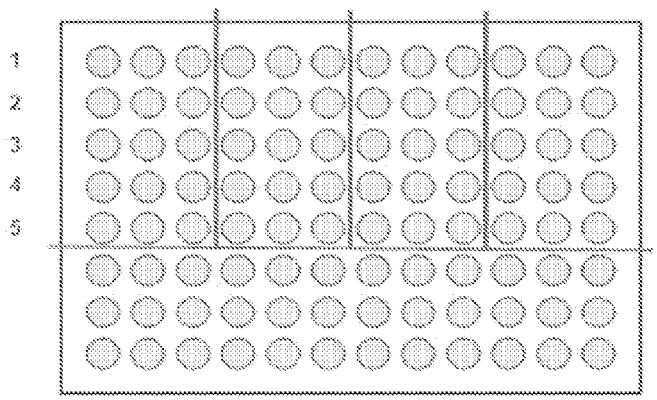

FIG. 6 provides a description of the experimental protocol demonstrating the immunosuppressant effects of selenide and iodide.

FIG. 7 provides a table demonstrating the immunosuppressant properties of iodide and selenide.

Figure 8:
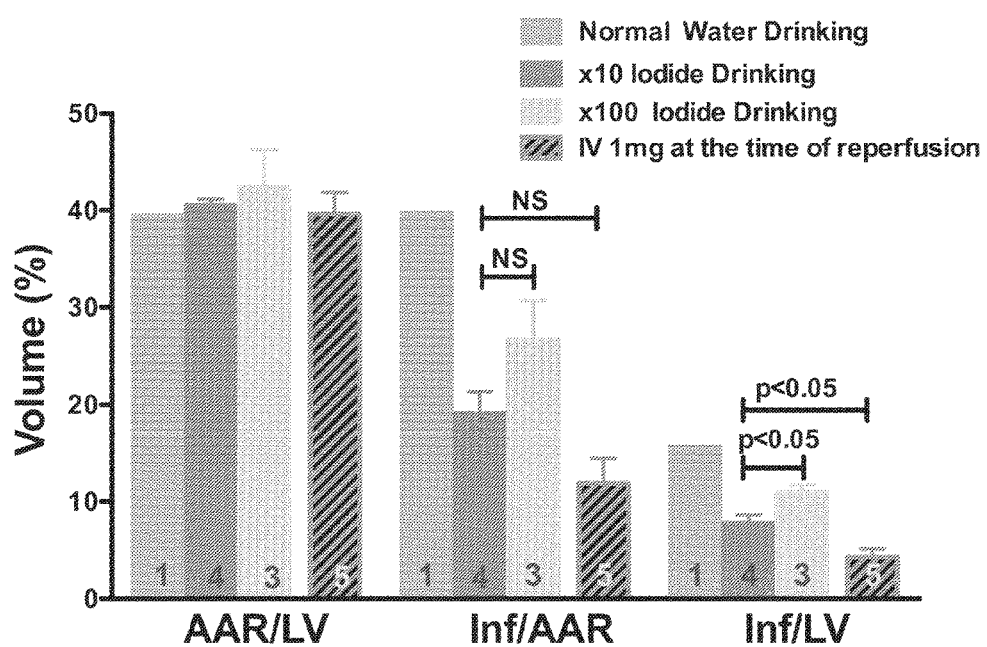

FIG. 8 provides a graph and table demonstrating NaI protection against infarct following ligation-induced ischemia. In the graph, the Inf/AAR and Inf/LV bars represent morphometric analysis of the infarct size (Inf) in relation to the total size of the area at risk (AAR) or left ventricle (LV), respectively, following ligation-induced ischemia initiated after two days of a diet including drinking water containing the indicated amounts of NaI. The AAR/LV bars shows the ratio of the size of the area at risk to the size of the left ventricle after drinking normal water or water containing increasing amounts of NaI (as indicated), and demonstrates that similar sampling was performed on all test subjects. For each of the sets of bars for Inf/AAR, Inf/LV and AAR/LV, the bars from left to right correspond to the bars from top to bottom shown in the legend. The amount of iodide present in the various drinking waters is indicated below the graph.

Figure 9:
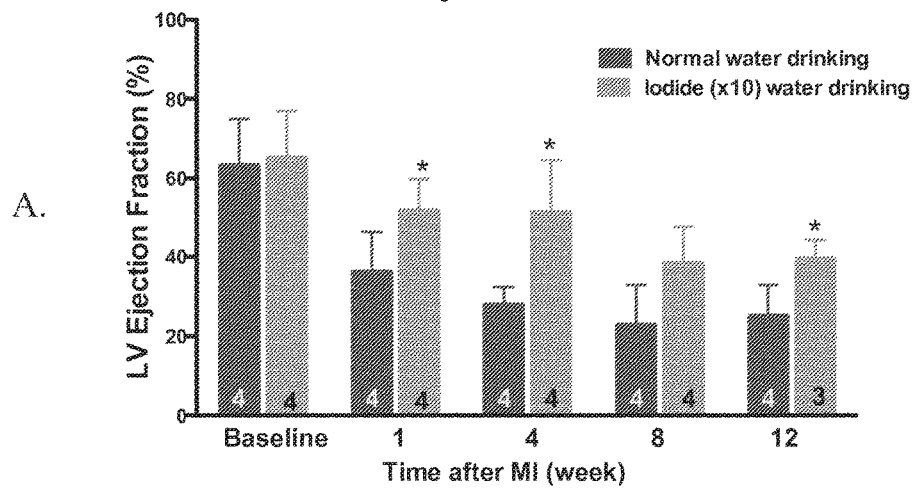
Figure 9:
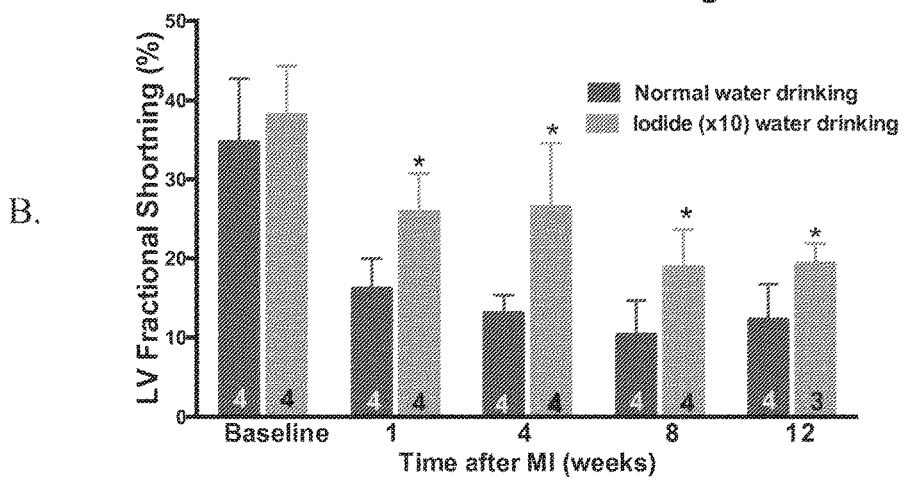

FIG. 9 provides graphs demonstrating NaI protection from chronic heart failure following ligation-induced myocardial infarct. FIG. 9A is a graph showing left ventricle (LV) ejection fraction (%) at baseline and the indicated times following induced myocardial infarct. A diet including drinking water containing 0.77 mg/kg of NaI was initiated just after the ligation procedure was completed. FIG. 9B is a graph showing LV fractional shortening (%) at baseline and the indicated times following induced myocardial infarct. A diet including drinking water containing 0.77 mg/kg of NaI was initiated just after the ligation procedure was completed. For each pair of bars, asterisks indicate a statistically significant difference between mice that received iodide containing (light bars) and normal drinking water (dark bars) ($p<0.05$).

Figure 10:
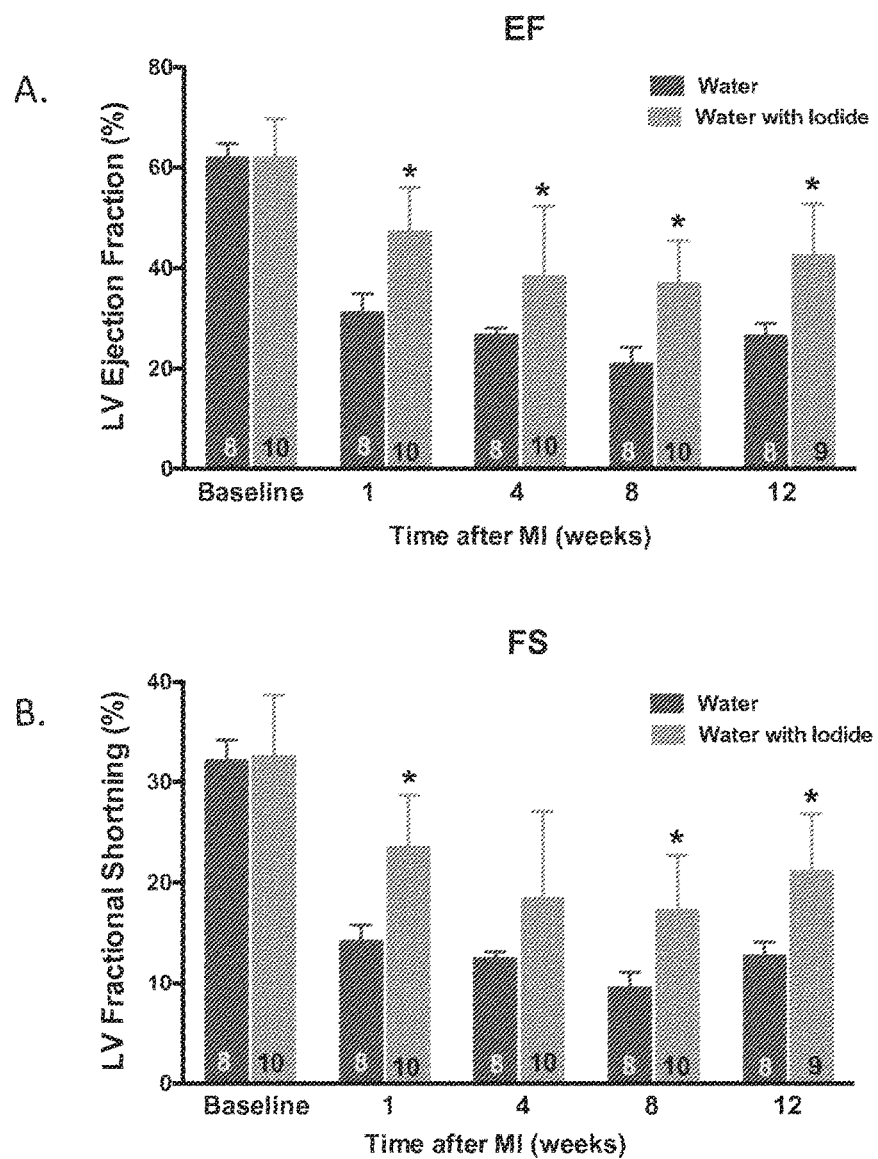

FIG. 10 provides graphs demonstrating NaI protection from chronic heart failure following ligation-induced myocardial infarct. FIG. 10A is a graph showing left ventricle (LV) ejection fraction (EF) (%) at baseline and the indicated times following induced myocardial infarct. A diet including drinking water containing 0.77 mg/kg of NaI was initiated just after the ligation procedure was completed. FIG. 10B is a graph showing LV fractional shortening (FS) (%) at baseline and the indicated times following induced myocardial infarct. A diet including drinking water containing 0.77 mg/kg of NaI was initiated just after the ligation procedure was completed. For each pair of bars, asterisks indicate a statistically significant difference between mice that received iodide containing (light bars) and normal drinking water (dark bars) ($p<0.05$).

Figure 11:
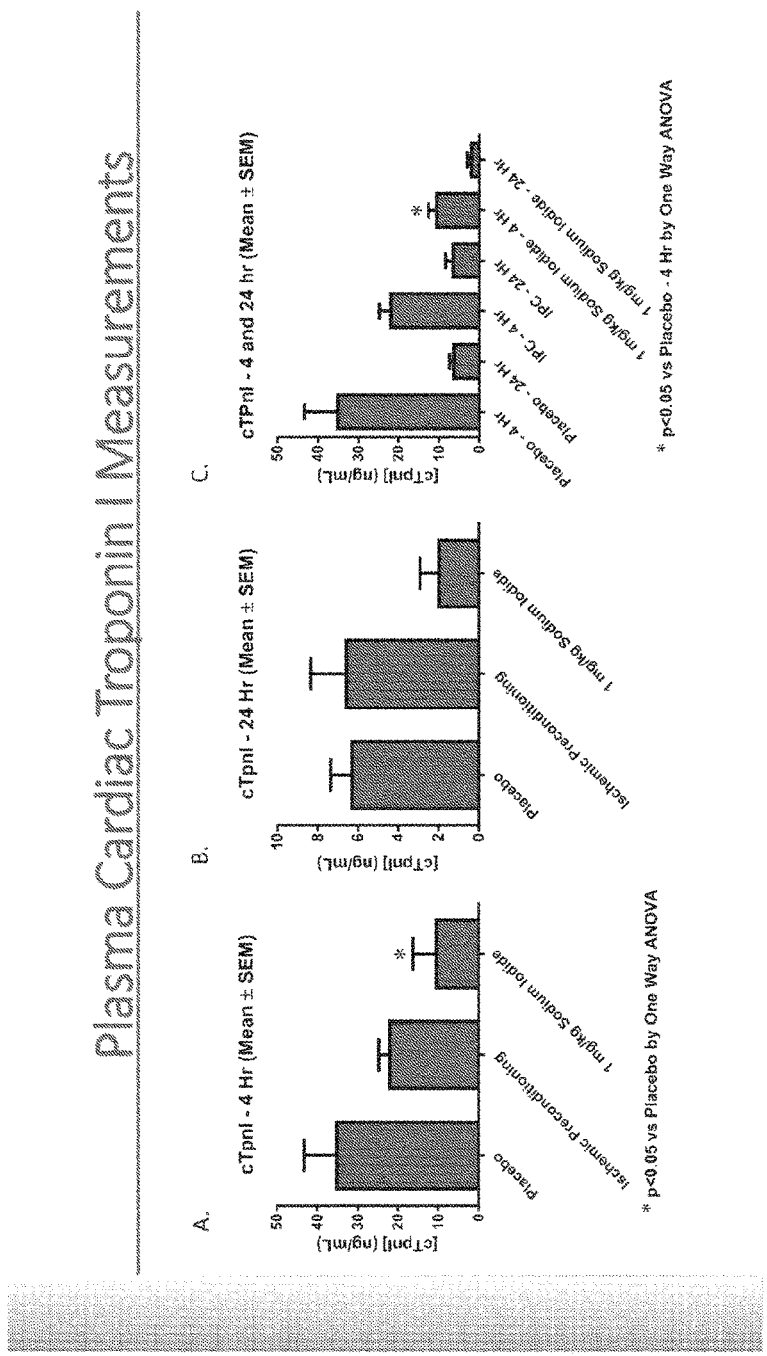

FIG. 11 provides graphs showing plasma cardiac troponin I (cTpnI) levels in the blood of animals treated with placebo, ischemic preconditioning, or 1 mg/kg NaI in a rat model of acute myocardial infarct. FIG. 11A is a graph showing cTpnI levels at 4 hours; FIG. 11B is a graph showing cTpnI levels at 24 hours; and FIG. 11C is a graph showing cTPNI levels at both 4 hours and 24 hours. *$p<0.05$ vs placebo by One Way ANOVA.

Figure 12:
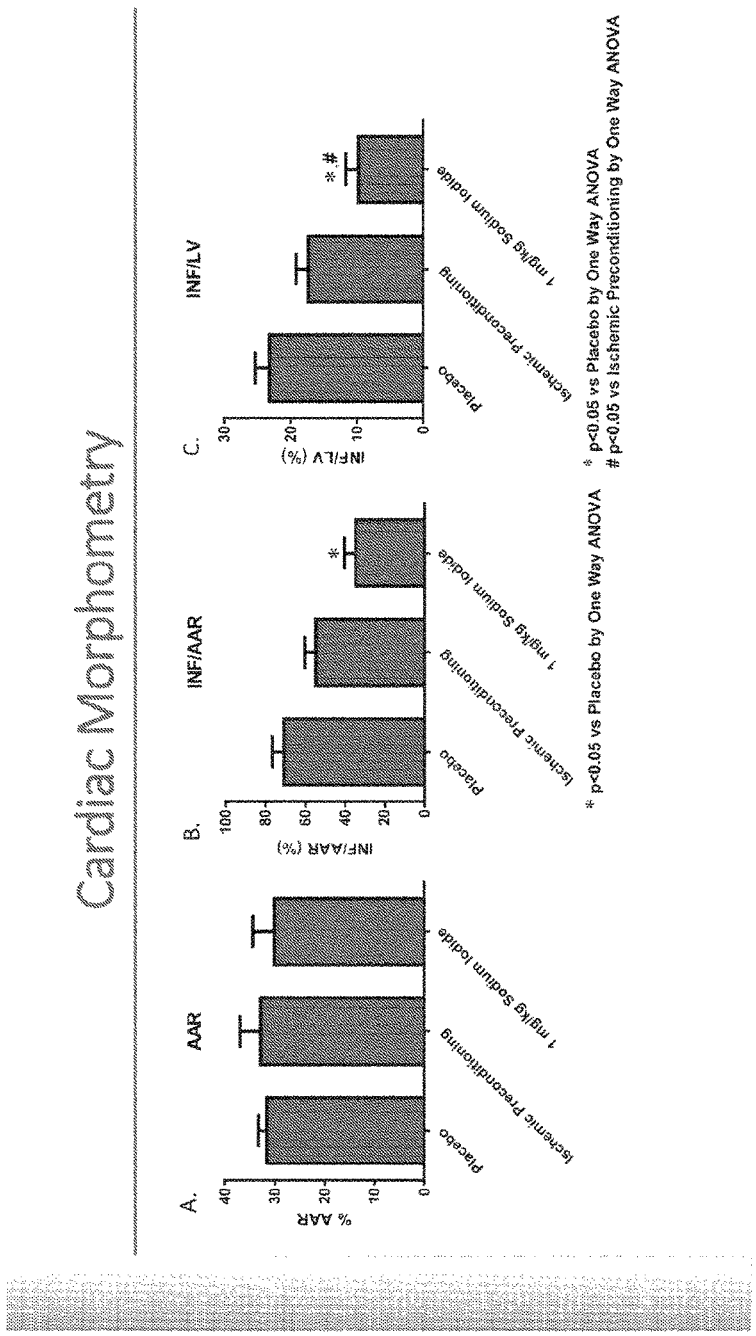

FIG. 12 provides graphs demonstrating successful NaI treatment of acute myocardial infarct. In the graphs, the Inf/AAR and Inf/LV bars represent morphometric analysis of the infarct size (Inf) in relation to the total size of the area at risk (AAR) or the left ventricle (LV), respectively. FIG. 12A shows AAR size in animals treated with placebo, ischemic preconditioning, or 1 mg/kg NaI; FIG. 12B shows % Inf/AAR in animals treated with placebo, ischemic preconditioning, or 1 mg/kg NaI; and FIG. 12C shows % Inf/LV in animals treated with placebo, ischemic preconditioning, or 1 mg/kg NaI. *$p<0.05$ vs placebo by One Way ANOVA; and #$p<0.05$ vs ischemic preconditioning by One Way ANOVA.

DETAILED DESCRIPTION OF THE INVENTION

The present invention is based, in part, on the surprising and unexpected finding that halogen compounds, such as iodides, may be used to treat or prevent diseases or injuries, including, e.g., those associated with hypoxia, ischemia or reperfusion, formation of reactive oxygen species, immune or inflammatory responses, or increased metabolic rate, including, e.g., chronic heart failure. As described in the accompanying Examples, treatment with a halogen compound before, during, or after ischemic assault, such as heart attack, protects against resulting tissue damage. In addition, the accompanying Examples demonstrate that treatment with a halogen improves the symptoms of chronic heart failure, e.g., following a heart attack. Accordingly, the present invention provides new methods of treating and preventing a variety of diseases, conditions, and injuries, including those associated with or resulting from hypoxia, ischemia and/or reperfusion, which comprise providing to a subject at risk of such disease, condition, or injury a composition comprising a halogen compound, such as an iodide. In certain embodiments, the composition may be provided to the subject prior to, concurrent with, or following the disease, condition, or injury. In addition, the present invention provides new compositions (e.g., pharmaceutical compositions) comprising a halogen compound. In certain embodiments, the composition comprises the halogen compound in a stable, reduced form, such as, e.g., an iodide. In particular embodiments, the composition is formulated for intravenous administration, administration by infusion, or oral administration. The methods of the present invention are particularly advantageous, because many halogen compounds are known to be safe for use in mammals, so the present invention provides new and safe ways of treating and preventing a number of diseases, conditions and injuries.

In addition, the present invention includes compositions, e.g., pharmaceutical compositions, comprising a stable, reduced form of a halogen compound, e.g., an iodide. These compositions may be formulated to maintain a halogen compound in a reduced form suitable for administration to a subject and, thus, constitute new and improved pharmaceutical products for treating and preventing a host of diseases, conditions and injuries, which have a shelf-life suitable for distribution and storage prior to use. In addition to a halogen compound, compositions of the present invention may further comprise one or more additional active agent, such as, e.g., a chalcogenide, which may also be in a stable, reduced form. Pharmaceutical compositions of the invention may be formulated for intravenous administration, infusion, or oral administration, in particular embodiments.

The present invention also includes unit dosage forms of a composition comprising an effective amount of a halogen compound, which are useful, inter alia, in treating a variety of diseases, conditions, and injuries. In various embodiments, the composition may be formulated for intravenous administration, administration by infusion, oral administration and/or formulated to maintain the halogen compound in a reduced form during storage. In particular embodiments, the unit dosage forms comprise or constitute pre-measured effective amounts of a halogen compound, which are advantageous for delivering an appropriate effective amount of a halogen compound to a subject, particularly during emergency intervention at site of injury or during transfer of a subject. In certain embodiments, the composition is a liquid composition, whereas in other embodiments, the composition is a solid or semi-solid composition. For example, the composition may be a liquid composition suitable for intravenous administration or administration by infusion, or the composition may be a solid or semi-solid composition, such as a pill, tablet, or capsule, suitable for oral administration.

Furthermore, the present invention includes methods and compositions related to the use of a halogen compound in combination with one or more additional active agents for the treatment or prevention of any of the diseases, conditions or injuries described herein, including those associated with or resulting from ischemia, hypoxia, or reperfusion. These methods include providing to a subject a composition comprising a halogen compound in combination with an additional composition comprising the one or more additional active agent, as well as methods that include providing to the subject a single composition comprising both the halogen compound and the one or more additional active agent. The present invention contemplates the use of a wide variety of additional active agents, including, e.g., chalcogenides, such as sulfides and selenides, as well as other agents. In particular embodiments, the composition comprises a halogen compound and another active agent used to treat or prevent chronic heart failure. The compositions may be formulated for a variety of different routes of administration, including but not limited to, intravenous administration, administration by infusion, or oral administration.

In certain embodiments, the present invention includes compositions that comprise a carrier, wherein a halogen compound is associated with the carrier. Additional active agents, such as chalcogenides may also be associated with the carrier. In one embodiment, the carrier is albumin or a related polypeptide, plasma, serum, alpha-2-macroglobulin, or immunoglobulin.

The present invention is also based, in part, on the surprising and unexpected finding that glutathione stabilizes or prevents oxidation of chalcogenides, including selenide. Accordingly, the present invention includes compositions (e.g., pharmaceutical compositions) comprising glutathione and a chalcogenide (such as selenide), optionally in combination with a halogen compound (such as iodide), which may be used to treat or prevent diseases or injuries, including, e.g., those associated with hypoxia, ischemia or reperfusion. In particular embodiments, the composition is formulated for intravenous administration, administration by infusion, or oral administration. The compositions of the present invention are particularly advantageous, because the glutathione inhibits oxidation of the chalcogenide, thus making the composition more stable are extending its shelf life.

The present invention also includes unit dosage forms of a composition comprising an effective amount of a chalcogenide and glutathione, which are useful, inter alia, in treating a variety of diseases, conditions, and injuries. The composition may further comprise an effective amount of a halogen compound. In particular embodiments, the unit dosage forms comprise or constitute a pre-measured effective amount of a chalcogenide, e.g., selenide or sulfide, which is advantageous for delivering an appropriate effective amount of a chalcogenide to a subject, particularly during emergency intervention at site of injury or during transfer of a subject. In certain embodiments, the composition is a liquid composition, whereas in other embodiments, the composition is a solid or semi-solid composition. For example, the composition may be a liquid composition suitable for intravenous administration or administration by infusion, or the composition may be a solid or semi-solid composition, such as a pill, tablet, or capsule, suitable for oral administration. The present invention is also based, in part, on the finding that glutathione stabilizes or prevents oxidation of halogens, including iodine compounds, e.g., iodide and iodate. Accordingly, the present invention includes compositions (e.g., pharmaceutical compositions) comprising glutathione and a halogen compound (such as an iodine compound, e.g., iodide or iodate), optionally in combination with another active agent, e.g., a chalcogenide compound (such as sulfide or selenide), which may be used to treat or prevent diseases or injuries, including, e.g., those associated with hypoxia, ischemia or reperfusion. In particular embodiments, the another active agent is one used to treat or prevent chronic heart failure. In certain embodiments, the composition comprises a halogen compound, glutathione, and another active agent used to treat or prevent heart failure. In particular embodiments, the composition is formulated for intravenous administration, administration by infusion, or oral administration. The compositions of the present invention are particularly advantageous, because the glutathione inhibits oxidation of the halogen compounds (and also the chalcogenide, if present), thus making the composition more stable are extending its shelf life.

The present invention also includes unit dosage forms of a composition comprising an effective amount of a halogen compound and glutathione, which are useful, inter alia, in treating a variety of diseases, conditions, and injuries. The composition may further comprise an effective amount of a chalcogenide and/or another active agent used to treat chronic heart failure. In particular embodiments, the unit dosage forms comprise or constitute a pre-measured effective amount of a halogen compound, e.g., an iodine compound, such as iodide or iodate, which is advantageous for delivering an appropriate effective amount of a halogen compound to a subject, particularly during emergency intervention at site of injury or during transfer of a subject. In certain embodiments, the composition is a liquid composition, whereas in other embodiments, the composition is a solid or semi-solid composition. For example, the composition may be a liquid composition suitable for intravenous administration or administration by infusion, or the composition may be a solid or semi-solid composition, such as a pill, tablet, or capsule, suitable for oral administration.

The present invention also includes unit dosage forms of a composition comprising an effective amount of a halogen compound and another active agent used to treat or prevent chronic heart failure, which are useful, inter alia, in treating or preventing chronic heart failure, e.g., following heart attack. The composition may further comprise an effective amount of a chalcogenide and/or glutathione. In particular embodiments, the unit dosage forms comprise or constitute a pre-measured effective amount of a halogen compound, e.g., iodide, and other active agent that is advantageous for delivering an appropriate effective amount of the halogen compound and other active agent to a subject, e.g., a subject suffering from chronic heart failure, or following heart attack. In certain embodiments, the composition is a liquid composition, whereas in other embodiments, the composition is a solid or semi-solid composition. For example, the composition may be a liquid composition suitable for intravenous administration or administration by infusion, or the composition may be a solid or semi-solid composition, such as a pill, tablet, or capsule, suitable for oral administration.

The present invention is also based, in part, on the discovery that selenide, iodide and other compounds that inhibit thyroid hormone production, activity, or uptake, including, e.g., goitrogens, impede or inhibit peroxide formation at the site of injury or disease, thus preventing the harmful effects of peroxide and, thus, preventing, inhibiting, or reducing said injury or disease. Accordingly, the present invention includes methods for treating or preventing any of the injuries and diseases described herein in a subject by providing to the subject a goitrogen, or an active agent that inhibits or impedes the formation of peroxide at the site of injury or disease. In particular embodiments, such active agent is iodide or selenide.

Without wishing to be bound by any particular theory, it is believed that the inhibition of thyroid hormone production by iodine is due, at least in part, to the Wolff Chaikoff effect. The Wolff-Chaikoff effect is a reduction in thyroid hormone levels caused by ingestion of a large amount of iodine. It is considered to be an autoregulatory phenomenon that inhibits organification (oxidation of iodide) in the thyroid gland, the formation of thyroid hormones inside the thyroid follicle, and the release of thyroid hormones into the bloodstream. This becomes evident secondary to elevated levels of circulating iodide. The Wolff-Chaikoff effect lasts several days (around 10 days), after which it is followed by resumption of normal organification of iodine and normal thyroid peroxidase function, which is believed to occur because of decreased inorganic iodine concentration secondary to down-regulation of sodium-iodide symporter (NIS) on the basolateral membrane of the thyroid follicular cell. By impeding thyroid hormone production, activity, or levels at the site of injury or disease, it is thought that metabolic activity is reduced, or hypermetabolic activity is inhibited, resulting in reduced damage to the injured or diseased tissue. While it is unknown how high iodide levels impede thyroid peroxidase to produce $H_2O_2$, without wishing to be bound to any particular theory, it is hypothesized that iodide donates electrons to hydrogen peroxide to make water, which has been incorrectly interpreted as inhibition of thyroperoxidase.

The present invention is also directed to the use of iodide or other elemental reducing agents (ERAs), such as sulfide or selenide, to treat or prevent any of the diseases, disorder, conditions, or injuries described herein. In addition, the present invention is also directed, in part, to methods of using halogen compounds and/or chalcogenides to inhibit, prevent or reduce an immune response in a subject. As described herein, halogen compounds, e.g., iodide, and chalcogenides, e.g., selenide, can inhibit or reduce reactive oxygen species. Accordingly, they may be used to reduce metabolic activity and stress, as well as inflammation and undesirable immune responses, including, e.g., those resulting from reactive oxygen species.

Compositions of the present invention, including stable compositions comprising a reduced form of halogen compound and/or a reduced form of a chalcogenide, may be used in any of the various methods of the present invention.

Definitions and Abbreviations

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

As used herein, the following terms have the meanings ascribed to them unless specified otherwise.

The term "including" is used to mean "including but not limited to." "Including" and "including but not limited to" are used interchangeably.

The words "a" and "an" denote one or more, unless specifically noted.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is as "including, but not limited to".

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7, 1.8, etc.) an amount or level described herein.

A "composition" can comprise an active agent, e.g., a halogen compound and/or a chalcogenide, and a carrier, inert or active, e.g., a pharmaceutically acceptable carrier, diluent or excipient. A composition may be a pharmaceutical composition. In particular embodiments, the compositions are sterile, substantially free of endotoxins or non-toxic to recipients at the dosage or concentration employed.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent or emulsifier which has been approved by the United States Food and Drug Administration as being acceptable for use in humans or domestic animals.

The term "biological matter" refers to any living biological material, including cells, tissues, organs, and/or organisms, and any combination thereof. It is contemplated that the methods of the present invention may be practiced on a part of an organism (such as in cells, in tissue, and/or in one or more organs), whether that part remains within the organism or is removed from the organism, or on the whole organism. Moreover, it is contemplated in the context of cells and tissues that homogenous and heterogeneous cell populations may be the subject of embodiments of the invention. The term "in vivo biological matter" refers to biological matter that is in vivo, i.e., still within or attached to an organism. Moreover, the term "biological matter" will be understood as synonymous with the term "biological material." In certain embodiments, it is contemplated that one or more cells, tissues, or organs is separate from an organism. The term "isolated" can be used to describe such biological matter. It is contemplated that the methods of the present invention may be practiced on in vivo and/or isolated biological matter.

The terms "mammal" and "subject" includes human and non-human mammals, such as, e.g., a human, mouse, rat, rabbit, monkey, cow, hog, sheep, horse, dog, and cat.

"Pharmaceutically acceptable salts" include sulfate, citrate, acetate, oxalate, chloride, bromide, iodide, nitrate, bisulfate, phosphate, acid phosphate, lsomcotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dimtrobenzoate, hydroxybenzoate, methoxybenzoate, methylbenzoate, o-acetoxybenzoate, naphthalene-2-benzoate, isobutyrate, phenylbutyrate, alpha-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, mcotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts. The term "pharmaceutically acceptable salt" also refers to a salt of an antagonist of the present invention having an acidic functional group, such as a carboxylic acid functional group, and a base. Suitable bases include, but are not limited to, hydroxides of alkali metals such as sodium, potassium, and lithium, hydroxides of alkaline earth metal such as calcium and magnesium, hydroxides of other metals, such as aluminum and zinc, ammonia, and organic amines, such as unsubstituted or hydroxy-substituted mono-, di-, or tri-alkylamines, dicyclohexylamine, tributylamine, pyridine, N-methyl, N-ethylamine, diethylamine, triethylamine, mono-, bis-, or tris-(2-OH-lower alkylamines), such as mono-, bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine, N-methyl-D-glucamine, and amino acids such as arginine, lysine, and the like. The term "pharmaceutically acceptable salt" also includes a hydrate of a compound of the invention.

The terms "tissue" and "organ" are used according to their ordinary and plain meanings Though tissue is composed of cells, it will be understood that the term "tissue" refers to an aggregate of similar cells forming a definite kind of structural material. Moreover, an organ is a particular type of tissue. In certain embodiments, the tissue or organ is "isolated," meaning that it is not located within an organism.

The terms "hypoxia" and "hypoxic" refer to an environment with levels of oxygen below normal. Hypoxia occurs when the normal physiologic levels of oxygen are not supplied to a cell, tissue, or organ. "Normoxia" refers to normal physiologic levels of oxygen for the particular cell type, cell state or tissue in question. "Anoxia" is the absence of oxygen. "Hypoxic conditions" are those leading to cellular, organ or organismal hypoxia. These conditions depend on cell type, and on the specific architecture or position of a cell within a tissue or organ, as well as the metabolic status of the cell. For purposes of the present invention, hypoxic conditions include conditions in which oxygen concentration is at or less than normal atmospheric conditions, that is less that 20.8, 20, 19, 18, 17, 16, 15, 14, 13, 12, 11, 10, 9, 8, 7, 6, 5, 4, 3, 2, 1, 0.5, 0%. Alternatively, these numbers could represent the percent of atmosphere at 1 atmosphere of pressure (101.3 kPa). "Anoxia" is the absence of oxygen. An oxygen concentration of zero percent defines anoxic conditions. Thus, hypoxic conditions include anoxic conditions, although in some embodiments, hypoxic conditions of not less than 0.5% are implemented. As used herein, "normoxic conditions" constitute oxygen concentrations of around 20.8% or higher.

The term "buffer" as used herein denotes a pharmaceutically acceptable excipient, which stabilizes the pH of a pharmaceutical preparation. Suitable buffers are well known in the art. Suitable pharmaceutically acceptable buffers include but are not limited to acetate-buffers, histidine-buffers, citrate-buffers, succinate-buffers, tris-buffers and phosphate-buffers. In certain embodiments, the concentration of the buffer is from about 0.01 mM to about 1000 mM, about 0.1 mM to bout 1000 mM, about 0.1 mM to about 500 mM, about 0.1 to about 200 mM, about 0.1 to about 100 mM, about 1 mM to about 1000 mM, about 1 mM to about 500 mM, about 1 mM to about 200 mM, about 1 mM to about 100 mM, about 1 mM to about 50 mM, about 2 mM to about 60 mM, about 4 mM to about 60 mM, or about 4 mM to about 40 mM, about 5 mM to about 20 mM, or about 5 mM to about 25 mM.

Pharmaceutically acceptable "cryoprotectants" are known in the art and include without limitation, e.g., sucrose, trehalose, and glycerol. Pharmaceutically acceptable cryoprotectants provide stability protection of compositions, or one or more active ingredients therein, from the effects of freezing and/or lyophilization.

The term "tonicity agent" or "tonicity modifier" as used herein denotes pharmaceutically acceptable agents used to modulate the tonicity of a composition. Suitable tonicity agents include, but are not limited to, sodium chloride, sorbitol, trehalose, potassium chloride, glycerin and any component from the group of amino acids, sugars, as defined herein as well as combinations thereof. In certain embodiments, tonicity agents may be used in an amount of about 1 mM to about 1000 mM, about 1 mM to about 500 mM, about 5 mM to about 500 mM, about 10 mM to about 450 mM, about 20 mM to about 400 mM, about 50 mM to about 300 mM, about 100 mM to about 200 mM, or about 125 mM to about 175 mM. In certain embodiments, a tonicity agent comprises an amino acid present in a composition at about 5 mM to about 500 mM.

The term "stabilizer" indicates a pharmaceutical acceptable excipient, which protects the active pharmaceutical ingredient(s) or agents(s) and/or the composition from chemical and/or physical degradation during manufacturing, storage and application. Stabilizers include, but are not limited to, sugars, amino acids, polyols, surfactants, antioxidants, preservatives, cyclodextrines, e.g. hydroxypropyl-β-cyclodextrine, sulfobutylethyl-β-cyclodextrin, β-cyclodextrin, polyethyleneglycols, e.g. PEG 3000, PEG 3350, PEG 4000, PEG 6000, albumin, e.g. human serum albumin (HSA), bovine serum albumin (BSA), salts, e.g. sodium chloride, magnesium chloride, calcium chloride, and chelators, e.g. EDTA. Stabilizers may be present in the composition in an amount of about 0.1 mM to about 1000 mM, about 1 mM to about 500 mM, about 10 to about 300 mM, or about 100 mM to about 300 mM.

As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants may be used as wetting, emulsifying, solubilizing, and dispersing agents for pharmaceutical compositions and preparations of biological materials. In some embodiments of the compositions described herein, the amount of surfactant is described as a percentage expressed in weight/volume percent (w/v %). Suitable pharmaceutically acceptable surfactants include, but are not limited to, the group of polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), or sodium dodecyl sulphate (SDS). Polyoxyethylenesorbitan-fatty acid esters include polysorbate 20, (sold under the trademark Tween 20™) and polysorbate 80 (sold under the trademark Tween 80™). Polyethylene-polypropylene copolymers include those sold under the names Pluronic® F68 or Poloxamer 188™. Polyoxyethylene alkyl ethers include those sold under the trademark Brij™ Alkylphenolpolyoxyethylene ethers include those sold under the tradename Triton-X. Polysorbate 20 (Tween 20™) and polysorbate 80 (Tween 80™) are generally used in a concentration range of about 0.001% w/v to about 1% w/v or about 0.002% w/v to about 0.1% w/v of the total volume of the composition, or alternatively of about 0.003% w/v to about 0.007% w/v. In some embodiments, Tween 80™ is used at about 0.003% w/v, about 0.004% w/v, about 0.0045% w/v, about 0.005% w/v, about 0.0055% w/v, about 0.006% w/v or about 0.007% w/v. In some embodiments, Tween 80™ is used at about 0.005% w/v. In this aspect, "w/v" intends the weight of surfactant per total volume of the composition.

A "lyoprotectant" refers to a pharmaceutically acceptable substance that stabilizes a protein, nucleic acid or other active pharmaceutical ingredient(s) or agent(s) during lyophilization. Examples of lyoprotectants include, without limitation, sucrose, trehalose or mannitol.

A "polyol" refers to an alcohol containing multiple hydroxyl groups, or a sugar alcohol. A sugar alcohol is a hydrogenated form of carbohydrate, whose carbonyl group (aldehyde or ketone, reducing sugar) has been reduced to a primary or secondary hydroxyl group (hence the alcohol). Sugar alcohols have the general formula $H(HCHO)_{n+1}H$, whereas sugars have $H(HCHO)_nHCO$.

An "antioxidant" refers to a molecule capable of slowing or preventing the oxidation of other molecules. Antioxidants are often reducing agents, chelating agents and oxygen scavengers such as thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

A "preservative" is a natural or synthetic chemical that is added to products such as foods, pharmaceutical compositions, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Examples of antimicrobial preservatives include benzalkonium chloride, benzoic acid, chlorhexidine, glycerin, phenol, potassium sorbate, thimerosal, sulfites (sulfur dioxide, sodium bisulfite, potassium hydrogen sulfite, etc.) and disodium EDTA. Other preservatives include those commonly used in parenteral protein compositions such as benzyl alcohol, phenol, m-cresol, chlorobutanol or methylparaben.

As used in the specification and appended claims, unless specified to the contrary, the following terms have the meaning indicated:

"Mammal" includes humans and both domestic animals such as laboratory animals and household pets, (e.g., cats, dogs, swine, cattle, sheep, goats, horses, and rabbits), and non-domestic animals such as wildlife and the like.

"Optional" or "optionally" means that the subsequently described event of circumstances may or may not occur, and that the description includes instances where said event or circumstance occurs and instances in which it does not.

"Pharmaceutical composition" refers to a formulation of a compound and a medium generally accepted in the art for the delivery of the biologically active compound to mammals, e.g., humans. Such a medium may include any pharmaceutically acceptable carriers, diluents or excipients therefore.

"Sulfide" refers to sulfur in its −2 valence state, e.g., either as $H_2S$ or as a salt thereof (e.g., NaHS, Na2S, etc.).

"Selenide" refers to selenium in its −2 valence state, e.g., either as $H_2Se$ or as a salt thereof (e.g., NaHSe, $Na_2Se$, etc.).

"Iodide" and "a reduced form of iodide" both refer to iodide, which has a −1 valence state (e.g., NaI). "A reduced form of iodine" includes iodide.

"Chalcogenide" or "chalcogenide compounds" refers to compounds containing a chalcogen element, i.e., those in Group 6 of the periodic table, but excluding oxides. These elements are sulfur (S), selenium (Se), tellurium (Te) and polonium (Po). Specific chalcogenides and salts thereof include, but are not limited to: $H_2S$, $Na_2S$, NaHS, $K_2S$, KHS, $Rb_2S$, $CS_2S$, $(NH_4)_2S$, $(NH_4)HS$, BeS, MgS, CaS, SrS, BaS, $H_2Se$, $Na_2Se$, NaHSe, $K_2Se$, KHSe, $Rb_2Se$, CS2Se, $(NH4)_2Se$, $(NH_4)HSe$, BeSe, MgSe, CaSe, SrSe, PoSe and BaSe.

As used herein, "oxidation product" refers to products that result from oxidation of a compound, e.g., a chalcogenide or halide compound, including, e.g., sulfite, sulfate, thiosulfate, polysulfides, dithionate, polythionate, elemental sulfur, selenite, selenate, thioselenate, polyselenides, and elemental selenium. Such oxidation products could occur as a result of processing, manufacturing or storage (e.g., by oxidation).

A used herein, "goitrogen" refers to a substance that inhibits the production of thyroid hormone by the body. While the mechanism is not entirely understood, it is believed that certain goitrogens suppress the function of the thyroid gland by interfering with iodine uptake or organification (synthesis of thyroid hormone), which can, as a result, cause an enlargement of the thyroid, i.e., a goiter, whereas other goitrogens may exert their effect through other mechanisms. Chemicals that have been shown to have goitrogenic effects include:

sulfadimethoxine, propylthiouracil, potassium perchlorate, and iopanoic acid;

some oxazolidines such as goitrin;

thiocyanate, e.g., thiocyanate overload in Central Africa, especially if also in conjunction with selenium deficiency. Reliance on cassava as a carbohydrate provides a source of thiocyanate in some areas;

ions such as thiocyanate and perchlorate, which decrease iodide uptake by competitive inhibition and, as a consequence of reduced thyroxine and triiodothyronine secretion by the gland, cause, at low doses, an increased release of thyrotropin (by reduced negative feedback), which then stimulates the gland;

amiodarone, which inhibits peripheral conversion of thyroxine to triiodothyronine; also interferes with thyroid hormone action;

lithium inhibits thyroid hormone release;

methimazole; and phenobarbitone, phenytoin, carbamazepine, rifampin induce metabolic degradation of triiodothyronine ($T_3$) and thyroxine ($T_4$).

"Therapeutically effective amount" refers to that amount of a compound or composition of the invention that, when administered to a biological material, e.g., a mammal, preferably a human, is sufficient to effect treatment, as defined below, of a disease, injury, or condition in the biological material, e.g., mammal, preferably a human. The amount of a compound or composition of the invention which constitutes a "therapeutically effective amount" will vary depending on the compound or composition, the disease, injury or condition and its severity, the manner of administration, and the age of the biological material, e.g., mammal, to be treated, but can be determined routinely by one of ordinary skill in the art having regard to his own knowledge and to this disclosure.

"Treating" or "treatment" as used herein covers the treatment of the disease, injury, or condition of interest, e.g., tissue injury, in a biological material, e.g., mammal, preferably a human, having the disease or condition of interest, and includes: (i) preventing or inhibiting the disease, injury, or condition from occurring in a biological material, e.g., mammal, in particular, when such mammal is predisposed to the condition but has not yet been diagnosed as having it; (ii) inhibiting the disease, injury, or condition, i.e., arresting its development; (iii) relieving the disease, injury, or condition, i.e., causing regression of the disease or condition; or (iv) relieving the symptoms resulting from the disease, injury, or condition. As used herein, the terms "disease," "disorder," and "condition" may be used interchangeably. As used herein, the term "injury" includes unintentional injuries and intentional injuries, including injuries that occur, "at the hand of man," including injuries associated with medical procedures, such as surgeries and transplantations.

"Chronic heart failure" (CHF), also referred to as congestive heart failure (CHF) or congestive cardiac failure (CCF), occurs when the heart is unable to pump sufficiently to maintain blood flow to meet the needs of the body. Common causes of CHF include coronary artery disease including a previous myocardial infarction (heart attack), high blood pressure, atrial fibrillation, valvular heart disease, and cardiomyopathy. These cause heart failure by changing either the structure or the functioning of the heart. The two main types of heart failure are: (1) heart failure due to left ventricular dysfunction, wherein the ability of the left ventricle to contract is affected, which is also referred to as systolic heart failure; and (2) heart failure with normal ejection fraction, wherein the heart's ability to relax is affected, which is also referred to as diastolic heart failure.

Halogen Compounds

The present invention relates to halogen compounds, said compounds comprising any element included in Group 17 of the periodic table. Any form of halogen compound may be used according to the present invention, including, e.g., hydrogen halides, metal halides, interhalogen compounds, organohalogen compounds, and polyhalogenated compounds. In some embodiments, a halogen compound refers to any compound containing Fluorine, Chlorine, Bromine, Iodine, Astatine, or Ununseptium. In particular embodiments, the present invention relates to halogen compounds in a reduced form, e.g., iodide.

Fluorine (F), the lightest halogen, is the non-metal element with atomic number 9. Under standard pressure and temperature it exists as a diatomic gas $F_2$. Fluorine is the most chemically reactive element, reacting with all other elements except oxygen, helium, neon, and krypton. It is also the most electronegative element, thus attracting electrons more strongly than all other elements. There are 11 fluorine isotopes with known half-lives, said isotopes having mass numbers ranging from 15 to 25. Natural Fluorine, however, consists of one stable isotope, $^{19}F$.

Chlorine (Cl), the second lightest halogen, is the non-metal element with atomic number 17. Under standard pressure and temperature it exists as a diatomic gas $F_2$. Chlorine is the element with the highest electron affinity, and the third highest electronegativity. There are 16 chlorine isotopes with known half-lives, said isotopes having mass numbers ranging from 31 to 46. Naturally occurring chlorine is a mixture of two stable isotope $^{35}Cl$ and $^{37}Cl$, existing in natural abundance ratios of approximately 3:1.

Bromine (Br), the third lightest halogen, is the non-metal element with atomic number 35. Under standard pressure and temperature it exists as a diatomic liquid $Br_2$. There are 26 bromine isotopes with know half-lives, said isotopes having mass numbers ranging from 68 to 94. Naturally occurring bromine is a mixture of two stable isotope $^{79}Cl$ and $^{81}Cl$, existing in natural abundance ratios of approximately 1:1.

Iodine (I), the second heaviest natural halogen, is the non-metal element with atomic number 53. Under standard pressure and temperature it exists as a solid diatomic $I_2$ molecule. There are 34 iodine isotopes with known half-lives, said isotopes having mass numbers ranging from 108 to 144. Natural iodine, however, consists of one stable isotope, $^{127}I$.

Astatine, the heaviest natural halogen, is a highly radioactive the non-metal element with atomic number 85. It decays so rapidly (longest half-life less than 12 hours) that its properties are not known with great certainty. It is debated if astatine exists as a diatomic $At_2$ molecule, as this form has never actually been observed. Astatine can react with hydrogen to form hydrogen astatide, and it is predicted to react with metals such as sodium to form salts. There are 37 known astatine isotopes, all of which are radioactive, with very short half-lives. Said isotopes have mass numbers ranging from 207 to 221. No stable isotopes of astatine exist.

In various embodiments, compositions and methods of the present invention comprise one or more halogen compounds, such as various forms of iodine or bromine.

In one embodiment, the present invention relates to a halogen compound containing iodine. In particular embodiments, the halogen compound is a reduced form of iodine, such as iodide. Certain embodiments may comprise an iodine-containing halogen compound that is an iodide, iodate, organoiodide, periodate, or periodinane.

In some embodiments, said halogen compound is an iodide comprising one or more compounds from the non-limiting list of Aluminium iodide, Aluminium monoiodide, Ammonium iodide, Antimony triiodide, Arsenic diiodide, Arsenic triiodide, Barium iodide, Beryllium iodide, Bismuth (III) iodide, Boron triiodide, Cadmium iodide, Caesium iodide, Calcium iodide, Candocuronium iodide, Carbon tetraiodide, Cobalt(II) iodide, Coccinite, Copper(I) iodide, DiOC6, Diphosphorus tetraiodide, Dithiazanine iodide, Echothiophate, Einsteinium(III) iodide, Eschenmoser's salt, Ethylenediamine dihydroiodide, Gallium(III) iodide, Gel-Green, GelRed, Germanium iodide, Gold monoiodide, Gold triiodide, Hydrogen iodide, Iodine oxide, Iodomethylzinc iodide, Iodosilane, Iron(II) iodide, Lead(II) iodide, Lithium iodide, Magnesium iodide, Manganese(II) iodide, Mercury (I) iodide, Mercury(II) iodide, Nickel(II) iodide, Nitrogen triiodide, Palladium(II) iodide, Phosphorus triiodide, Polyiodide, Potassium iodide, Potassium tetraiodomercurate(II), Propidium iodide, Rubidium iodide, Rubidium silver iodide, Samarium(II) iodide, Silicon tetraiodide, Silver iodide, Sodium iodide, Strontium iodide, Tellurium iodide, Tellurium tetraiodide, Terbium(III) iodide, Tetraethylammonium iodide, Thallium triiodide, Thallium(I) iodide, Thorium(IV) iodide, Tibezonium iodide, Tiemonium iodide, Tin(II) iodide, Tin(IV) iodide, Titanium tetraiodide, Triiodide, Trimethylsilyl iodide, Trimethylsulfoxonium iodide, Uranium pentaiodide, Uranium tetraiodide, Uranium triiodide, Vanadium(III) iodide, Zinc iodide, and Zirconium(IV) iodide.

In particular embodiments, said halogen compound is an iodide comprising sodium iodide, potassium iodide, hydrogen iodide, calcium iodide, or silver iodide.

In some embodiments, said halogen compound is an iodate comprising one or more compounds from the non-limiting list of Calcium iodate, Iodic acid, Potassium iodate, Seeligerite, Silver iodate, and Sodium iodate.

In particular embodiments, said halogen compound is an iodate comprising sodium iodate, potassium iodate, calcium iodate, or silver iodate.

In some embodiments, said halogen compound is an organoiodide comprising one or more compounds from the non-limiting list of $^{25}$I-NBF, $^{25}$I-NBMD, $^{25}$I-NBOH, $^{25}$I-NBOMe, 2C-I, 5, 5-I-R91150, Acetrizoic acid, Adipiodone, Adosterol, Altropane, AM-1241, AM-2233, AM-630, AM-679 (cannabinoid), AM-694, AM251, Amiodarone, Benziodarone, Bromoiodomethane, Budiodarone, Butyl iodide, Carbon tetraiodide, Chiniofon, Chloroiodomethane, Clioquinol, Diatrizoic acid, Diiodohydroxypropane, Diiodohydroxyquinoline, Diiodomethane, 2,5-Dimethoxy-4-iodo-amphetamine, Domiodol, Erythrosine, Ethyl iodide, Ethyl iodoacetate, Fialuridine, Fluoroiodomethane, Haloprogin, Herapathite, IAEDANS, Ibacitabine, IDNNA, Idoxifene, Idoxuridine, Iniparib, Iobenguane, Iobenzamic acid, Iobitridol, Iocarmic acid, Iocetamic acid, Iodamide, Iodixanol, Iodoacetamide, Iodoacetic acid, Para-Iodoamphetamine, Iodobenzamide, Iodobenzene, 2-Iodobenzoic acid, 19-Iodocholesterol, Iodocyanopindolol, Iodoform, 1-Iodomorphine, Iodophenol, Iodophenpropit, 4-Iodopropofol, Iodopropynyl butylcarbamate, Iodotrifluoroethylene, Iodoxamic acid, 2-Iodoxybenzoic acid, Iofetamine (1231), Ioflupane (1231), Ioglicic acid, Ioglycamic acid, Iomazenil, Iomeprol, Iopamidol, Iopanoic acid, Iopentol, Iopromide, Iopydol, Iotrolan, Iotroxic acid, Ioversol, Ioxaglic acid, Ioxilan, Ipodate sodium, Isopropyl iodide, Methiodal, Methyl iodide, Metrizamide, Metrizoic acid, Pentafluoroethyl iodide, Plakohypaphorine, N-Propyl iodide, Propyliodone, Rafoxanide, Rose bengal, RTI-121, RTI-229, RTI-353, RTI-55, SB-258, 585, Sodium acetrizoate, Tiratricol, Trifluoroiodomethane, and Tyropanoic acid.

In particular embodiments, said halogen compound is an organoiodide. Organoiodine compounds are organic compounds that contain one or more carbon-iodine bonds. Almost all organoiodine compounds feature iodide connected to one carbon center. These are usually classified as derivatives of I$^-$. Some organoiodine compounds feature iodine in higher oxidation states. Organoiodine compounds, often used as disinfectants or pesticides, include, e.g., iodoform ($CHI_3$), methylene iodide ($CH_2I_2$), and methyl iodide ($CH_3I$). In particular embodiment, the organoiodide is a polyiodoorganic compound. Polyiodoorganic compounds are sometimes employed as X-ray contrast agents, in fluoroscopy, a type of medical imaging. A variety of such polyiodoorganic compounds are available commercially; many are derivatives of 1,3,5-triiodobenzene and contain about 50% by weight iodine. In certain embodiments, the agent is soluble in water, non-toxic and/or readily excreted. A representative reagent is Ioversol, which has water-solubilizing diol substituents. Other organoiodine compounds include but are not limited to the two thyroid hormones thyroxine ("$T_4$") and triiodothyronine ("$T_3$"). Marine natural products are rich sources of organoiodine compounds, including the recently discovered plakohypaphorines from the sponge Plakortis simplex.

The present invention also includes the use of compounds, e.g., drug compounds, into which an iodine is incorporate. For example, an iodine may be incorporated into existing drugs such as N-acetyl cysteine, standard pain relievers, and non-steroidal anti-inflammatory drugs, such as, e.g., aspirin, ibuprofen and naproxen. Most NSAIDs act as nonselective inhibitors of the enzyme cyclooxygenase (COX), inhibiting both the cyclooxygenase-1 (COX-1) and cyclooxygenase-2 (COX-2) isoenzymes.

In certain embodiments, said halogen compound is a polyiodide. The polyiodides are a class of polyhalogen anions composed of entirely iodine atoms. The most common and simplest member is the triiodide ion, $I_3^-$. Other known, larger polyiodides include $[I_4]^{2-}$, $[I_5]^-$, $[I_7]^-$, $[I_8]^{2-}$, $[I_9]^-$, $[I_{10}]^{2-}$, $[I_{10}]^{4-}$, $[I_{11}]^-$, $[I_{12}]^{2-}$, $[I_{13}]^{-3}$, $[I_{16}]^{-2}$, $[I_{22}]^{-4}$, $[I_{26}]^{3-}$, $[I_{26}]^{4-}$, $[I_{28}]^{4-}$ and $[I_{29}]^{3-}$. One example of a polyiodide is Lugol's iodine, also called Lugol's solution. Lugol's solution is commercially available in different potencies of 1%, 2%, or 5% Iodine. The 5% solution consists of 5% (wt/v) iodine ($I_2$) and 10% (wt/v) potassium iodide (KI) mixed in distilled water and has a total iodine content of 130 mg/mL. Potassium iodide renders the elementary iodine soluble in water through the formation of the triiodide ($I^{-3}$) ion. Other names for Lugol's solution are $I_2KI$ (iodine-potassium iodide); Markodine, Strong solution (Systemic); and Aqueous Iodine Solution BCP. Examples of polyiodides, including their ions and counter-cations are shown in Table 1.

TABLE 1

Polyiodides

| Anion | Counter-cation |
|---|---|
| $[I_3]^-$ | $Cs^+$ |
| $[I_4]^{2-}$ | $[Cu(NH_3)_4]^{2+}$ |
| $[I_5]^-$ | $[EtMe_3N]^+$ |
|  | $[EtMePh_2N]^+$ |
| $[I_7]^-$ | $[Ag(18aneS_6)]^+$ |
| $[I_8]^{2-}$ | $[Ni(phen)_3]^{2+}$ |
| $[I_9]^-$ | $[Me_2{}^iPrPhN]^+$ |
|  | $[Me_4N]^+$ |
| $[I_{10}]^{2-}$ | $[Cd(12\text{-crown-}4)_2]^{2+}$ |
| $[I_{11}]^{3-}$ | $[(16aneS_4)PdIPd(16aneS_4)]^{3+}$ |
| $[I_{12}]^{2-}$ | $[Ag_2(15aneS_5)_2]^{2+}$ |
|  | $[Cu(Dafone)_3]^{2+}$ |
| $[I_{13}]^{3-}$ | $[Me_2Ph_2N]^+$ |
| $[I_{16}]^{2-}$ | $[Me_2Ph_2N]^+$ |
|  | $[{}^iPrMe_2PhN]^+$ |
| $[I_{22}]^{4-}$ | $[MePh_3P]^+$ |
| $[I_{26}]^{3-}$ | $[Me_3S]^+$ |
| $[I_{26}]^{4-}$ | $DMFc^+$ |
| $[I_{29}]^{3-}$ | $Cp_2Fe$ |
| $[I_{22}]^{4-}$ | $[MePh_3P]^+$ |
| $[I_{26}]^{3-}$ | $[Me_3S]^+$ |
| $[I_{26}]^{4-}$ | $DMFc^+$ |
| $[I_{29}]^{3-}$ | $Cp_2Fe$ |
| $[I_{22}]^{4-}$ | $[MePh_3P]^+$ |
| $[I_{26}]^{3-}$ | $[Me_3S]^+$ |
| $[I_{26}]^{4-}$ | $DMFc^+$ |

In one embodiment, the halogen compound is a tincture of iodine solutions, which comprises or consists of elemental iodine, and iodide salts dissolved in water and alcohol.

In some embodiments, said halogen compound is a periodate comprising one or more compounds from the non-limiting list of Dess-Martin periodinane, 1, 2-Iodoxybenzoic acid, Periodic acid, Potassium periodate, and Sodium periodate.

In particular embodiments, said halogen compound is a periodate comprising sodium periodate, potassium periodate, calcium periodate, or silver periodate.

In particular embodiments, said halogen compound is a periodinane. Periodinanes are chemical compounds containing hypervalent iodine. In some embodiments, said halogen compound is a periodinane comprising one or more compounds from the non-limiting list of (Bis(trifluoroacetoxy)iodo)benzene, Dess-Martin periodinane, Iodobenzene dichloride, Iodosobenzene, and 2-Iodoxybenzoic acid.

In one embodiment, the halogen compound is an oil-infused iodide or iodine oil infusion.

In one embodiment, the present invention relates to a halogen compound containing bromine. Certain embodiments may comprise a bromine-containing halogen compound that is a bromide, bromate, organobromide, or a perbromate.

In some embodiments, said halogen compound is a bromide comprising one or more compounds from the non-limiting list of Aclidinium bromide, Aluminium bromide, Ammonium bromide, ANNINE-6plus, Antimony tribromide, Arsenic tribromide, Barium bromide, Benzododecinium bromide, Beryllium bromide, Bibenzonium bromide, Bismuth tribromide, Boron tribromide, Bromargyrite, Bromo(tetrahydrothiophene)gold(I), Bromopentaamminecobalt(III) bromide, Bromopentacarbonylrhenium(I), Cadmium bromide, Caesium bromide, Caesium cadmium bromide, Calcium bromide, Cerium(III) bromide, Cetrimonium bromide, Chromium(III) bromide, Cimetropium bromide, Clidinium bromide, Cobalt(II) bromide, Copper(I) bromide, Copper(II) bromide, Cyanogen bromide, Demecarium bromide, Ditellurium bromide, DODAB, Domiphen bromide, EEthidium bromide, Fazadinium bromide, Fentonium, Gallium(III) bromide, Gold(I) bromide, Gold(III) bromide, Hexafluronium bromide, Hydrobromic acid, Hydrogen bromide, Indium(I) bromide, Indium(III) bromide, Iodine monobromide, Iron(II) bromide, Iron(III) bromide, Lanthanum(III) bromide, Lead(II) bromide, Lithium bromide, Magnesium bromide, Manganese(II) bromide, Mercury(I) bromide, Mercury(II) bromide, Morphine methylbromide, Nickel(II) bromide, Niobium bromide, Niobium(V) bromide, Nitrogen tribromide, Nitrosyl bromide, Otilonium bromide, Oxitropium bromide, Oxyphenonium bromide, Palladium(II) bromide, Pancuronium bromide, Phosphorus heptabromide, Phosphorus pentabromide, Phosphorus tribromide, Pifithrin, Pipecuronium bromide, Platinum(II) bromide, Platinum(IV) bromide, Polonium dibromide, Potassium bromide, Propantheline bromide, Radium bromide, Rubidium bromide, Silicon tetrabromide, Silver bromide, Sodium bromide, Strontium bromide, TTantalum(V) bromide, Tellurium tetrabromide, Terbium(III) bromide, Tetrabromoauric acid, Tetrabromomethane, Thallium(I) bromide, Timepidium bromide, Tin(II) bromide, Tin(IV) bromide, Titanium tetrabromide, Tribromosilane, Triphenylcyclopropenium bromide, Tungsten(V) bromide, Tungsten(VI) oxytetrabromide, Uranium pentabromide, Uranium tetrabromide, Vanadium(III) bromide, Ytterbium(III) bromide, Yttrium(III) bromide, Zinc bromide, and Zirconium(IV) bromide.

In particular embodiments, said halogen compound is a bromide comprising sodium bromide, potassium bromide, hydrogen bromide, calcium bromide, or silver bromide.

In some embodiments, said halogen compound is a bromate comprising one or more compounds from the non-limiting list of Bromic acid, Calcium bromate, Potassium bromate, Silver bromate, Sodium bromate, and Strontium bromate.

In some embodiments, said halogen compound is an organobromide comprising one or more compounds from the non-limiting list of 2-Bromobutyric acid, 25B-NBOMe, 2C-B, 2C-B-BZP, 2C-B-FLY, 2CB-Ind, 2CBCB-NBOMe, 2CBFly-NBOMe, 66-Br-APB, Acecarbromal, Ageliferin, Allyl bromide, AM-087, Ambroxol, Arbidol, AS-8112, BCDMH, Benzbromarone, Benzyl bromide, Bibrocathol, Brallobarbital, Bretazenil, Bretylium, Bretylium for the treatment of ventricular fibrillation, Brimonidine, Brivudine, Brodifacoum, Brodimoprim, Brofaromine, Bromacil, Bromadiolone, Bromadoline, Bromantane, Bromazepam, Bromazine, Bromethalin, Bromfenac, Bromhexine, Brominated flame retardant, Bromisoval, 2-Bromo-1-chloropropane, 4-Bromo-3,5-dimethoxyamphetamine, 2-Bromo-4,5-methylenedioxyamphetamine, Bromo-DragonFLY, Bromoacetic acid, Bromoacetone, Bromoacetylalprenololmenthane, 8-Bromoadenosine 3',5'-cyclic monophosphate, Para-Bromoamphetamine, 4-Bromoaniline, Bromoanisole, Bromobenzene, Bromobimane, 1-Bromobutane, 2-Bromobutane, Bromochlorodifluoromethane, Bromochloromethane, Bromochlorosalicylanilide, Bromocresol green, Bromocresol purple, Bromocriptine, Bromocyclohexane, Bromodeoxyuridine, Bromodichloromethane, Bromodifluoroacetyl chloride, Bromodifluoromethane, Bromodiphenylmethane, B cont.Bromoethane, Bromofluoromethane, Bromoform, 3-Bromofuran, 8-Bromoguanosine 3',5'-cyclic monophosphate, 1-Bromohexane, 2-Bromohexane, Bromoiodomethane, Bromomethane, 4-Bromo-N-methylcathinone, Bromopentane, Bromophenol blue, Bromadol, 2-Bromopropane, Bromopyruvic acid, N-Bromosuccinimide, Bromotrifluoromethane, 5-Bromouracil, 5-Bromouridine, Bromoxynil, Bromperidol, Brompheniramine, Bromsulphthalein, Bronidox, Bronopol, Brophebarbital, Bropirimine, Brotizolam, Broxaterol, Broxyquinoline, Butallylonal, Tert-Butyl bromide, C-8813, Carbromal, Chlorfenapyr, Ciclotizolam, Convolutindole A, DBDMH, DBNPA, Decabromodiphenyl ether, Deltamethrin, Desformylflustrabromine, Dexbrompheniramine, Diarylpyrimidines, 1,2-Dibromo-3-chloropropane, 1,4-Dibromobenzene, Dibromochloromethane, Dibromodifluoromethane, 1,1-Dibromoethane, 1,2-Dibromoethane, Dibromofluoromethane, Dibromomethane, 1,2-Dibromopropane, 1,3-Dibromopropane, Dibromotetrafluoroethane, Dibromotyrosine, Dibromopropamidine, Difethialone, 2,5-Dimethoxy-4-bromoamphetamine, DS-1 (drug), Ebrotidine, Embramine, Eosin, Eosin B, Eosin Y, Ethyl bromoacetate, Etravirine, FL3 (flavagline), Flubromazolam, Gidazepam, H-89, Halofuginone, Halomon, Halothane, Haloxazolam, Hexabromocyclododecane, Ibrolipim, Imidazenil, Isobromindione, JWH-249, JWH-424, KF-26777, Lonafarnib, Mebroqualone, Merbromin, Meta-DOB, Metaclazepam, Mitobronitol, Mucobromic acid, Narcobarbital, Nelotanserin, Neltenexine, NGD-4715, Nicergoline, 0-806, Octabromodiphenyl ether, Organobromine compound, P7C3, Pamabrom, PEAQX, Pentabromodiphenyl ether, Phenacyl bromide, Phenazepam, 2-Phenylethylbromide, Phloxine, Pinaverium, Pindobind, Pipobroman, PNU-282,987, Polybrominated biphenyl, Polybrominated diphenyl ethers, Propallylonal, Propargyl bromide, N-Propyl bromide, Remoxipride, Romifidine, RTI-51, SB-357,134, Sigmodal, SSR-180,711, Stampidine, Surinabant, Surugatoxin, TCB-2, Tetrabromobisphenol A, Tetrabromoethane, Tetrabromoethylene, Tetrabromomethane, TH-302, Tilbroquinol, Tralomethrin, 2,4,6-Tribromoanisole, and Tribromofluoromethane.

In some embodiments, said halogen compound is a perbromate, said perbromate comprising sodium perbromate, potassium perbromate, hydrogen perbromate, or silver perbromate.

Particular embodiments of the present invention relate to a reduced form of a halogen compound. Many acceptable means of reduction of halogen compounds are possible and known to one skilled in the art. Examples of reduced forms of halide compounds include, e.g., iodide and bromide, wherein the halogen has a valency of −1. Non-limiting examples of reduction methods include chemical reduction with electropositive elemental metals (such as lithium, sodium, magnesium, iron, zinc, and aluminum, e.g.), hydride transfer reagents (such as $NaBH_4$ and $LiAlH_4$, e/g), or the use of hydrogen gas with a palladium, platinum, or nickel catalyst.

A particular embodiment of the present invention relates to the administration of a halogen compound of the type described herein to a mammalian subject, said compounds administered in a composition, concentration or formulation that is not significantly toxic to said mammals, e.g., a pharmaceutical composition. In particular embodiments, a halogen compound known to be toxic to a mammalian subject is excluded from the present invention. Thus, in particular embodiments, potassium iodide is excluded from the present invention. It is further contemplated that some embodiments may comprise the administration of more than one of said halogen compounds to said mammal, either simultaneously or separately, such that the combination of said compounds that are not individually significantly toxic are also not significantly toxic when combined.

Other compounds comprising a halogen compound or halogen element may also be used according to methods of and/or included in compositions of the present invention. In some embodiments, said halogen compound is a commercially available substance. In certain embodiments, said commercially available substances may include radiological contrast agents, topical iodine preparations, solutions, or drugs. In certain embodiments, said commercially available substance comprises iodine, and may be selected from the non-limiting list of Diatrizoate, Ipanoic acid, Ipodate, Iothalamate, Metrizamide, Diatrozide, Diiodohydroxyquinolone, Iodine tincture, Povidone iodine, Iodochlorohydroxyquinolone, Iodoform gauze, Saturated potassium iodide (SSKI), Lugol solution, Iodinated glycerol, Echothiopate iodide, Hydriodic acid syrup, Calcium iodide, Amiodarone, Expectorants, Vitamins containing iodine, Iodochlorohydroxyquinolone, Diiodohydroxyquinolone, Potassium iodide, Benziodarone, Isopropamide iodide, levothyroxine, and Erythrosine. In certain embodiments, said commercially available substance comprises bromine, and may be selected from the non-limiting list of Alphagen (brimonidine), Atrovent (Ipratropium), Celexa (citalopram), Combivent (ipratropium bromide), Enablex (darifenacin), Guaifenex DM (dextromethorphan), Razadyne (galantamine), and Spiriva (tiotropium).

Certain compositions and methods of the present invention comprise a halogen compound, in combination with glutathione and/or a goitrogen. As discussed herein, glutathione can stabilize halogen compounds in a reduced form, and goitrogens can inhibit production of thyroid hormone.

Other Active Agents

The present invention further includes the use of other active agents, alone or in combination with a halogen compound, to treat or prevent any of the diseases, conditions or injuries described herein. A variety of agents effective in treating or preventing any of these diseases, conditions or injuries have been described or are known in the art, and any of these agents or other agents may be used. In addition, other agents may be used in combination with a halogen compound according to the methods of the present invention.

In certain embodiments, an active agent is a chalcogenide or salt thereof. It has been shown that treatment with a chalcogenide induces stasis of biological matter and protects biological matter from hypoxic and ischemic injury. In these studies, it was demonstrated that sulfide can reduce metabolism and protect mice and rats from hypoxic injuries (PCT Publication No. WO2005/041655). Compounds containing a chalcogen element, i.e., those in Group 6 of the periodic table, but excluding oxides, are commonly termed "chalcogenides" or "chalcogenide compounds." These elements are sulfur (S), selenium (Se), tellurium (Te) and polonium (Po). Common chalcogenides contain one or more of S, Se, and Te, in addition to other elements. Specific chalcogenides and salts thereof include, but are not limited to: $H_2S$, $Na_2S$, NaHS, $K_2S$, KHS, $Rb_2S$, $CS_2S$, $(NH_4)_2S$, $(NH_4)HS$, BeS, MgS, CaS, SrS, BaS, $H_2Se$, $Na_2Se$, NaHSe, $K_2Se$, KHSe, $Rb_2Se$, $CS_2Se$, $(NH_4)_2Se$, $(NH_4)HSe$, BeSe, MgSe, CaSe, SrSe, PoSe and BaSe. A variety of chalcogenides are described in WO2005/041656, WO2005/041655 and WO2006/113914.

In certain embodiments, an active agent is an oxygen antagonist. The term "oxygen antagonist" refers to a substance that competes with oxygen insofar as it used by a biological matter that requires oxygen for it to be alive ("oxygen-utilizing biological matter"). Oxygen is typically used or needed for various cellular processes that create the biological matter's primary source of readily utilizable energy. An oxygen antagonist effectively reduces or eliminates the amount of oxygen that is available to the oxygen-utilizing biological matter, and/or the amount of oxygen that can be used by the oxygen-utilizing biological matter. Thus, in some embodiments, an oxygen antagonist inhibits or reduces the amount of cellular respiration occurring in the cells, for instance, by binding sites on cytochrome c oxidase that would otherwise bind to oxygen. One example of an oxygen antagonist is carbon monoxide. A variety of oxygen antagonists are described in WO2005/041656, WO2005/041655 and WO2006/113914.

In additional embodiments, an active agent is a stasis-inducing compound, such as rotenone. Additional stasis-inducing compounds are described, e.g., in US2010/0021387.

In certain embodiments, an active agent is an elemental reducing agent (ERA), such as iodide, sulfide or selenide.

In other embodiments, an active agent is a HIF modulating compound, a variety of which are described in US2009/0011051. The transcription factor HIF (hypoxia inducible factor) system is a key regulator of responses to hypoxia, occupying a central position in oxygen homeostasis in a wide range of organisms. A large number of transcriptional targets have been identified, with critical roles in angiogenesis, erythropoiesis, energy metabolism, inflammation, vasomotor function, and apoptotic/proliferative responses. The system is essential for normal development, and plays a key role in pathophysiological responses to ischaemia/hypoxia. HIF is also important in cancer, in which it is commonly upregulated, has major effects on tumor growth and angiogenesis. The HIF DNA binding complex consists of a heterodimer of $\alpha$ and $\beta$ subunits. Regulation by oxygen occurs through hydroxylation of the $\alpha$-subunits, typically of one or more proline residues, which are then rapidly destroyed by the proteasome in oxygenated cells. This involves binding of HIF$\alpha$-subunits by the von Hippel-Lindau tumor suppressor protein (pVHL or VHL), with pVHL acting as the, or part of the, recognition component for a ubiquitin ligase that promotes ubiquitin dependent proteolysis through interaction with a specific sequence or sequences in HIF $\alpha$-subunits. In hypoxia, this process is suppressed, thereby stabilizing HIF$\alpha$ and permitting transcriptional activation via the HIF $\alpha/\beta$ heterodimer. Certain compounds shown to affect metabolic activity also act to stabilize HIF, thereby implicating such compounds as preventative and treatment regimes for hypoxia, ischemia, stasis, and/or any other condition or state associated with HIF stabilization, such as hemorrhagic shock. Any of these compounds may be used according to the present invention.

In other embodiments, an active agent is a polychalcogenide. Representative polychalcogenides are described in WO2009/003061.

In further embodiments, an active agent is a polysulfide compound, examples of which are described in WO2010/045582.

Another active agent that can be used, e.g., in combination with a halogen compound, is nitric oxide.

Certain compositions and methods of the present invention comprise a chalcogenide, in combination with glutathione and/or a goitrogen. As discussed herein, glutathione can stabilize chalcogenides in a reduced form, and goitrogens can inhibit production of thyroid hormone.

In certain embodiments, methods of the present invention include providing to a subject in need thereof any of the following agents or compounds, alone or in combination, including but not limited to any of the combinations shown below:

a halogen compound;
a chalcogenide;
a goitrogen or other compound that reduces or inhibits thyroid hormone production, activity or uptake;
a halogen compound and a chalcogenide;
a chalcogenide and glutathione;
a halogen compound and glutathione; and
a halogen compound, a chalcogenide, and glutathione.

In certain embodiments, a halogen compound is administered or coformulated with an active agent used to treat CHF, e.g., CHF due to left ventricular dysfunction, such as an angiotensin converting enzyme (ACE) inhibitor, a beta blocker, an aldosterone antagonist, an angiotension receptor blocker, or hydralazine with a nitrate. In additional embodiments, the another active agent is an anticoagulant, an antiplatelet therapy, an angiotensin II receptor blocker, a calcium channel blocker, a diuretic, a vasodilator, or a statin.

Non-limiting examples of angiotensin converting enzyme inhibitors that may be used according to the present invention include: include: captopril (Capoten®), enalapril (Vasotec®), lisinopril (Prinivil®, Zestril®), benazepril hydrochloride (Lotensin®), fosinopril sodium (Monopril®), ramipril (Altace®), quinapril hydrochloride (Accupril®), perindopril erbumine (Aceon®), trandolapril (Mavik®), and moexipril hydrochloride (Univasc®).

Non-limiting examples of nonselective beta blockers that may be used according to the present invention include: alpurinol, bucindolol, carteolol, carvedilol (has additional $\alpha$-blocking activity), labetalol (has additional $\alpha$-blocking activity), nadolol, oxprenolol (has intrinsic sympathomimetic activity), penbutolol (has intrinsic sympathomimetic activity), pindolol (has intrinsic sympathomimetic activity), propranolol, sotalol, timolol, and eucommia bark (herb).

Non-limiting examples of $\beta_1$-selective beta blockers that may be used according to the present invention (also known as cardioselective) include: acebutolol (has intrinsic sympathomimetic activity), atenolol, betaxolol, bisoprolol, beliprolol, esmolol, metoprolol, and nebivolol (also increases nitric oxide release for vasodilation).

Non-limiting examples of $\beta_2$-selective agents that may be used according to the present invention include: butaxamine (weak $\alpha$-adrenergic agonist activity).

Non-limiting examples of beta blockers specifically indicated for chronic heart failure include: carvedilol, sustained-release metoprolol, bisoprolol, and nebivolol.

Non-limiting examples of angiotensin II blockers include: candesartan (Atacand®), eprosartan (Teveten®), irbesartan (Avapro®), losartan (Cozaar®), telmisartan (Micardis®) and valsartan (Diovan®).

In certain embodiments, methods of the present invention include providing to a subject in need, e.g., a subject diagnosed with or at risk for chronic heart failure, thereof any of the following agents or compounds, alone or in combination, including but not limited to any of the combinations shown below:

a halogen compound;
a halogen compound and glutathione;
a halogen compound and another active agent used to treat chronic heart failure; and
a halogen compound, another active agent used to treat chronic heart failure, and glutathione.

When used in combination, the two or more agents may be provided to the subject in the same or in different compositions. In addition, when three or more agents are provided to a subject, two may be in one composition, and the third in a separate composition. The compositions may be administered concurrently, during overlapping time periods, or during different time periods.

Compositions and Unit Dosage Forms

The present invention also includes compositions comprising a halogen compound, such as, e.g., an iodide or bromide. In particular embodiments, the composition further comprises one or more additional active agents, including any of those described herein. In certain embodiments, compositions of the present invention are pharmaceutical compositions. In particular embodiments, compositions of the present invention further comprise a pharmaceutically acceptable carrier, diluent, or excipient, such as, e.g., a buffer. In certain embodiments, compositions of the present invention are pharmaceutical compositions comprising a halogen compound and glutathione. Particular compositions comprise a halogen compound, e.g an iodide, and another compound used to treat or prevent chronic heart failure. Additional compositions of the invention comprise glutathione, in combination with a chalcogenide and/or a halogen compound. In certain embodiments, a composition comprises glutathione, a chalcogenide, and a halogen compound. In particular embodiments, a composition of the invention comprises glutathione and selenide. In particular embodiments, a composition of the invention comprises glutathione and sulfide. In certain embodiments, a composition of the present invention comprises iodide (or iodate), selenide and glutathione. In certain embodiments, a composition of the present invention comprises iodide (or iodate), sulfide and glutathione. In particular embodiments, at least a portion of the selenide or sulfide is in reduced form, and the glutathione inhibits the oxidation of the chalcogenide in the composition. The reduced form of chalcogenide may be any of those described herein. In particular embodiments, at least a portion of the iodide or iodate is in reduced form, and the glutathione inhibits the oxidation of the halogen compound in the composition. The reduced form of halogen compound may be any of those described herein.

In certain embodiments, the present invention includes compositions comprising a halogen compound, e.g., a reduced form of a halogen compound. In related embodiments, the invention includes compositions comprising a halogen compound, e.g., a reduced form of a halogen compound and one or more additional active agents, e.g., a chalcogenide, such as a reduced form of a chalcogenide, or an active agent used to treat chronic heart failure. In certain embodiments, the composition further comprises glutathione. The invention further includes methods that involve providing to a subject a composition comprising a reduced form of a halogen compound, alone or in combination with providing to the subject a composition comprising one or more additional active agent, such as, e.g., a reduced form of a chalcogenide. In particular embodiments, a reduced form of a chalcogenide comprises a chalcogen, e.g., sulfur or selenium, in a −2 valence state. In particular embodiments, a single composition comprises both the halogen compound and the one or more additional active agent or an active agent used to treat chronic heart failure. In certain embodiments of any of the compositions of the invention, the halogen compound is a reduced form of a halogen compound, which comprises a halogen in a −1 valence state, e.g., an iodide or bromide, such as sodium iodide. In certain embodiments of any of the compositions described herein, the composition further comprises glutathione or another reducing agent.

In particular embodiments, the compositions are formulated to maintain the halogen and/or chalcogenide in a reduced form when stored over a period of time. Thus, the compositions may be stable compositions of reduced forms of halogen compounds and/or reduced forms of chalcogenides, or salts or precursors thereof, whose effectiveness as a therapeutic may normally be compromised during manufacture and storage, as a result of oxidation reactions that produce oxidation products. The compositions of the present invention have increased shelf-life, are easily and reproducibly manufactured, are designed for standard routes of administration, and are, therefore, advantageous in the treatment and prevention of a number of diseases, conditions and injuries. The present invention contemplates their use in methods of protecting biological tissue from disease or injury, particularly ischemic, hypoxic or reperfusion injury, as well as methods of treating or preventing injury or disease in a subject.

In certain embodiments, a stable composition comprising a chalcogenide and/or a halogen compound comprises glutathione.

In additional embodiments, a composition comprises a goitrogen or an active agent that inhibits or reduces thyroid hormone production, activity or uptake, alone or in combination with another active agent, such as a chalcogenide and/or halogen compound.

In certain embodiments of the compositions, a composition is considered stable, i.e., a stable composition, if at least 90% of the halogen compound or the chalcogenide (if present in the composition), or both the halogen compound and the chalcogenide (if both present in the composition), in the composition is present in reduced form for at least one hour either when stored at room temperature, 4° C., 25° C., 40° C. or 50° C. In related embodiments, a composition is considered stable if at least 70%, at least 80%, at least 91%, at least 92%, at least 93%, at least 94%, at least 95%, at least 96%, at least 97%, at least 98%, or at least 99% of the halogen compound, the chalcogenide, or both the halogen compound and the chalcogenide, in the composition is present in reduced form for at least one hour either when stored at room temperature or when stored at 4° C. In certain embodiments of the stable compositions, at least 90% of the halogen compound, the chalcogenide, or both the halogen compound and the chalcogenide, in said composition is present in said reduced form for at least one day, at least one week, at least one month, at least two months, at least four months, at least six months, or at least one year, either when stored at room temperature or when stored at 4° C., 25° C., 40° C. or 50° C. In related embodiments, at least 70%, at least 80%, at least 91%, at least 92%, at least 93%, at least 94%, at least 95%, at least 96%, at least 97%, at least 98%, or at least 99% of the halogen compound, the chalcogenide, or both the halogen compound and the chalcogenide, in the stable composition is present in said reduced form for at least one day, at least one week, at least one month, at least two months, at least four months, at least six months, or at least one year, either when stored at room temperature or when stored at 4° C. In particular embodiments, at least 98% of the halogen compound, the chalcogenide, or both the halogen compound and the chalcogenide, in the stable composition is present in said reduced form for at least one month or at least six months when stored at 4° C. In related embodiments, at least 70%, at least 80%, at least 91%, at least 92%, at least 93%, at least 94%, at least 95%, at least 96%, at least 97%, at least 98%, or at least 99% of the halogen compound, the chalcogenide, or both the halogen compound and the chalcogenide, in the stable composition is present in said reduced form for at least one day, at least one week, at least one month, at least two months, at least four months, at least six months, or at least one year, either when stored at room temperature or when stored at room temperature or 25° C. In particular embodiments, at least 98% of the halogen compound, the chalcogenide, or both the halogen compound and the chalcogenide, in the stable composition is present in said reduced form for at least one month or at least six months when stored at room temperature or 25° C. In related embodiments, at least 70%, at least 80%, at least 91%, at least 92%, at least 93%, at least 94%, at least 95%, at least 96%, at least 97%, at least 98%, or at least 99% of the halogen compound, the chalcogenide, or both the halogen compound and the chalcogenide, in the stable composition is present in said reduced form for at least one day, at least one week, at least one month, at least two months, at least four months, at least six months, or at least one year, either when stored at room temperature or when stored at 40° C. or 50° C. In particular embodiments, at least 98% of the halogen compound, the chalcogenide, or both the halogen compound and the chalcogenide, in the stable composition is present in said reduced form for at least one month or at least six months when stored at 40° C. or 50° C. In various embodiments, the composition is a liquid pharmaceutical composition, while in other embodiments, the composition is a solid or powder, or is dried, lyophilized, or freeze-dried.

In particular embodiments, the present invention relates to a stable liquid composition comprising iodide, wherein the stable liquid composition comprises less than 1% of any of the following oxidation products of iodide (−1 oxidation state): hypoiodite (+1 oxidation state), iodite (+3 oxidation state), iodate (+5 oxidation state), or periodate (+7 oxidation state). In particular embodiments, the stable liquid composition comprising iodide comprises less than 1% iodine ($I_2$).

In certain embodiments, a reduced form of a halogen compound comprises a halogen in a −1 valence state. In particular embodiments, a reduced form of a chalcogenide comprises a chalcogen e.g., sulfur or selenium, in a −2 valence state. In particular embodiments, the reduced form of a halogen is a reduced form of the halogen, iodine, such as iodide. In particular embodiments, the reduced form of a halogen compound is NaI, KI, HI, CaI or AgI. In particular embodiments, the reduced form of a chalcogenide is $H_2Se$, $Na_2Se$, NaHSe, HSe—, $H_2S$, NaHS, $Na_2S$, or HS—.

In particular embodiments, any of the compositions described herein comprise a pharmaceutically acceptable carrier, diluent or excipient. Further, any of the compositions may comprise one or more of a buffer, a reducing agent, a tonicity agent, a stabilizer, a surfactant, a lycoprotectant, a polyol, an antioxidant, or a preservative. In particular embodiments, any of the composition described herein comprise glutathione.

In particular embodiments, compositions may comprise one or more solvents. In particular embodiments, the solvent is water. In particular embodiments, the solvent is a phosphate-buffered saline.

Compositions of the present invention and methods of the present invention may include a halogen compound and/or a chalcogenide compound, or salt or precursor thereof, in any desired concentration. The concentration may be readily optimized, e.g., depending upon the type of injury or disease being treated and the route of administration, so as to deliver an effective amount in a convenient manner and over an appropriate time-frame.

In some embodiments, the concentration of halogen compound or salt or precursor thereof present in a composition of the present invention is about 0.0001 mM to about 100 M, about 0.0005 mM to about 50 M, about 0.001 mM to about 10 M, about 0.001 mM to about 5 M, about 0.001 mM to about 1 M, about 0.005 mM to about 10 M, about 0.005 mM to about 5 M, about 0.005 mM to about 1 M, about 0.005 mM to about 0.5 M, about 0.01 mM to about 10 M, about 0.01 mM to about 5 M, about 0.01 mM to about 2 M, about 0.1 mM to about 1 M, about 0.1 mM to about 0.5 M, about 0.5 mM to about 5 M, about 0.5 mM to about 2 M, about 0.5 mM to about 1 M, about 0.5 mM to about 0.5 M, about 1 mM to about 5 M, about 1 mM to about 2 M, about 1 mM to about 1 M, about 1 mM to about 0.5 M, about 5 mM to about 5 M, about 5 mM to about 2 M, about 5 mM to about 1 M, about 5 mM to about 0.5 M, about 5 mM to about 0.25 M, about 10 mM to about 1 M, about 10 mM to about 0.5 M, about 10 mM to about 0.25 M, or about 10 mM, about 50 mM about 100 mM, or about 200 mM.

In some embodiments, the concentration of chalcogenide or chalcogenide compound or salt or precursor thereof is about 0.001 mM to about 5,000 mM, about 1 mM to about 1000 mM, about 10 mM to about 500 mM, about 50 mM to about 500 mM, about 75 mM to about 250 mM, or about 95 mM to 150 mM.

In particular embodiments, a composition comprises selenide at a concentration of about 0.1 mM to about 1000 mM, about 1 mM to about 1000 mM, about 5 mM to about 1000 mM, about 10 mM to about 1000 mM, about 10 mM to about 750 mM, about 50 mM to about 500 mM, about 100 mM to about 500 mM, about 10 mM to about 500 mM, 1 mM to about 500 mM, or about 10 mM to about 250 mM.

In particular embodiments, a composition comprises sulfide at a concentration of about 0.1 mM to about 1000 mM, about 1 mM to about 1000 mM, about 5 mM to about 1000 mM, about 10 mM to about 1000 mM, about 10 mM to about 750 mM, about 50 mM to about 500 mM, about 100 mM to about 500 mM, about 10 mM to about 500 mM, 1 mM to about 500 mM, or about 10 mM to about 250 mM.

In certain embodiments, the concentration of the reduced form of halogen compound and/or chalcogenide, e.g., selenide or sulfide, in a composition of the present invention is about, at least about, or at most about 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mM or M or more or any range derivable therein (at standard temperature and pressure (STP)).

As used herein, the term "%" when used without qualification (as with w/v, v/v, or w/w) means % weight-in-volume for solutions of solids in s (w/v), % weight-in-volume for solutions of gases in s (w/v), % volume-in-volume for solutions of s in s (v/v) and weight-in-weight for mixtures of solids and semisolids (w/w) (Remington's Pharmaceutical Sciences (2005); 21st Edition, Troy, David B. Ed. Lippincott, Williams and Wilkins).

In one embodiment, a composition comprises selenide or sulfide measured at 80%-100% (w/v). In one embodiment, a composition comprises selenide or sulfide measured at 90%-100% (w/v). In one embodiment, a composition comprises selenide or sulfide measured at 95%-100% (w/v). In one embodiment, a composition comprises sulfide measured at 98%-100% (w/v).

In certain embodiments, a composition comprises glutathione at a concentration of about 1.5 µM to about 10 M, about 15 µM to about 1 M, about 150 µM to about 1 M, about 1.5 mM to about 10 mM to about 500 mM, about 10 mM to about 250 mM, or about 100 mM, about 120 mM, about 150 mM, about 170 mM, or about 200 mM.

In certain embodiments, a composition comprises a goitrogen or a compound that inhibits or impedes thyroid hormone production, activity or uptake at a concentration of about 0.1 µM to about 100 M, about 1.5 µM to about 10 M, about 15 µM to about 1 M, about 150 µM to about 1 M, about 1 mM to about 1 M, about 10 mM to about 500 mM, about 10 mM to about 250 mM, or about 100 mM, about 120 mM, about 150 mM, about 170 mM, or about 200 mM.

In certain embodiments, a composition of the invention comprises a chalcogenide and glutathione, and optionally a halogen compound or salt or precursor thereof, wherein the concentration of the chalcogenide is about 1 mM to about 1 M, about 10 mM to about 500 mM, or about 10 mM to about 100 mM, the concentration of glutathione is about 100 µM to about 1 M, about 1 mM to about 1 M, or about 10 mM to about 500 mM, and, if present, the concentration of halogen compound is about 0.01 mM to about 5 M, about 1 mM to about 0.5 M, or about 10 mM to about 250 mM. In certain embodiments, the halogen compound is present in the composition. In particular embodiments, the halogen compound is an iodide or iodate, and the chalcogenide comprises selenium or sulfur. In certain embodiments, a composition of the invention comprises a halogen compound or salt or precursor thereof and glutathione, and optionally a chalcogenide, wherein the concentration of the halogen compound is about 0.01 mM to about 5 M, about 1 mM to about 0.5 M, or about 10 mM to about 250 mM, the concentration of glutathione is about 100 µM to about 1 M, about 1 mM to about 1 M, or about 10 mM to about 500 mM, and, if present, the concentration of halogen compound is about about 1 mM to about 1 M, about 10 mM to about 500 mM, or about 10 mM to about 100 mM. In certain embodiments, the chalcogenide is present in the composition. In particular embodiments, the halogen compound is an iodide or iodate, and the chalcogenide comprises selenium or sulfur. In particular embodiments of any of these compositions, the composition is formulated for oral delivery, or is an oral dosage form, the halogen compound (when present) comprises iodine (e.g., iodide or iodate), and the chalcogenide (when present) comprises selenium. In certain embodiments, the chalcogenide is selenide or selenide. In particular embodiments, the composition is formulated for intravenous administration, and the halogen compound (if present) is iodide or iodate, and the chalcogenide (if present) is in a reduced form, e.g., selenide or sulfide. In one embodiment, the composition comprises selenide, iodide and glutathione, each within any of the concentration ranges or at a concentration described herein.

In particular embodiments, the pH of a composition of the present invention is in the range of (3.0-12.0), while in other embodiments, the pH is in the range of (5.0-9.0). The pH of the pharmaceutical composition may be adjusted to a physiologically compatible range. For example, in one embodiment, the pH of the stable composition is in the range of 6.5-8.5. In other embodiments, the compositions of the present invention have a pH in the range of 7.5-8.5 or 7.4-9.0.

In particular embodiments, oxygen is present in a composition of the present invention at a concentration in the range of 0 µM$^{-5}$ µM or 0 µM$^{-1}$ µM or 0 µM$^{-0.1}$ µM or 0 µM-0.01 µM. In particular embodiments, oxygen is present in the composition at a concentration of less than 3 µM, less than 1 µM, less than 0.1 µM, less than 0.01 µM, or less than 0.001 µM.

In certain embodiments, the compositions of the present invention may further comprise a limited amount of oxidation products. Oxidation products that may be present in various embodiments of the present invention include, but are not limited to, iodine, iodate, bromine, bromate, selenite, thioselenate, polyselenides, elemental selenium, selenate, sulfite, sulfate, thiosulfate, polysulfides, dithionate, polythionate, and elemental sulfur. In various embodiments, one or more of these oxidation products is present in a composition in an amount less than 10%, less than 5.0%, less than 2.0%, less than 1.0%, less than 0.5%, less than 0.2%, less than 0.1%, less than 0.05%, or less than 0.01% (w/v) of the total halogen compound and/or chalcogenide in the composition.

In one embodiment, a composition has an osmolarity in the range of 200-400 mOsmol/L. NaCl may be used as an excipient to adjust osmolality.

In certain embodiments, isotonicity of the compositions is desirable as it results in reduced pain upon administration and minimizes potential hemolytic effects associated with hypertonic or hypotonic compositions. Thus, the compositions of the invention not only have increased storage stability, but also have the added benefit of substantially reduced pain upon administration when compared with formulations using other more traditional buffer systems consisting of an acid and a salt form of the acid.

Stable liquid compositions comprising reduced forms of chalcogenides, including sulfide or selenide, and methods of manufacturing the same, have been described, e.g., in PCT Application Publication No. WO2008/043081, U.S. Provisional Application No. 61/659,311, and PCT Application Publication No. WO2013/188528. Any of these composition may be used to treat or prevent any of the diseases, disorders or injuries described herein Compositions of the invention comprising a reduced form of a chalcogenide and further comprising glutathione may be prepared by one of skill in the art in a similar manner, e.g., by preparing a composition comprising the reduced form of chalcogenide and adding the glutathione. Similarly, compositions comprising a reduced form of a chalcogenide and a reduced form of a halogen compound may be prepared by one of skill in the art in a similar manner, e.g., by preparing a composition comprising the reduced form of chalcogenide and combining it with a reduced form of a halogen compound or with a composition comprising a reduced form of a halogen compound.

WO2008/043081 describes compositions comprising a stable liquid pharmaceutical chalcogenide or chalcogenide compound or salt or precursor thereof in a pharmaceutically acceptable carrier, wherein the concentration, pH and oxidation products of said chalcogenide or chalcogenide compound or salt remain within a range of acceptance criteria after storage of said liquid pharmaceutical composition. In various embodiments, the chalcogenide compound or chalcogenide salt is selected from the group consisting of: $H_2S$, $Na_2S$, NaHS, $K_2S$, KHS, $Rb_2S$, $Cs_2S$, $(NH_4)_2S$, $(NH_4)HS$, BeS, MgS, CaS, SrS, and BaS. In other embodiments, the chalcogenide compound or chalcogenide salt is selected from the group consisting of: $H_2Se$, $Na_2Se$, NaHSe, $K_2Se$, KHSe, $Rb_2Se$, $Cs_2Se$, $(NH_4)_2Se$, $(NH_4)HSe$, BeSe, MgSe, CaSe, SrSe, PoSe and BaSe. According to the present invention, said compositions may further comprise a halogen compound, e.g., iodide, glutathione, or a goitrogen.

In particular embodiments of stable liquid or aqueous compositions, the chalcogenide compound or chalcogenide salt is sulfide and has a concentration in the range of 95 mM to 150 mM.

In particular embodiments wherein said chalcogenide compound or chalcogenide salt is sulfide, said sulfide is present in amounts ranging from about 80% to about 100%, about 90% to 100%, or about 95% to 100% by w/v.

In particular embodiments, the liquid is sodium hydroxide.

In certain embodiments, the composition has a pH in the range of 6.5 to 8.5. In one embodiment, the composition has an oxygen content of less than or equal to 5 µM.

In one embodiment, the composition further comprises one or more oxidation products selected from polysulfide, sulfite, sulfate and thiosulfate. The oxidation products may be sulfate in the range of (0%-1.0%), or sulfite in the range of (0%-1.0%), or polysulfide in the range of (0%-1%) or thiosulfate in the range of (0%—1.0%).

The storage period may be about 3 months at a range of (23°–27°) or 6 months at a range of (23°–27°). In one embodiment, the composition has an osmolarity in the range of 250-330 mOsmol/L. It may be isotonic or near isotonic.

In certain embodiments, a composition is a sterile, stable aqueous pharmaceutical composition comprising a solution of deoxygenated water and sodium sulfide nonahydrate, wherein the sodium sulfide nonahydrate produces $Na_2S$, $H_2S$ and $HS^-$, wherein the concentration of $H_2S$ is in the range of 1.0 mg/mL to 4.0 mg/mL; wherein the solution is adjusted to a pH in the range of 7.5 to 8.5 by adding HCl to the solution; wherein the solution has an osmolarity in the range of 250-330 mOsmol/L; wherein the solution further comprises sulfide oxidation products selected from the group consisting of polysulfide, sulfite, sulfate and thiosulfate; wherein the oxidation products comprise sulfate in the range of (0%-1.0%), sulfite in the range of (0%-1.0%), polysulfide in the range of (0%-1%) or thiosulfate in the range of (0%-1.0%); wherein the solution is isotonic or near isotonic; and, wherein the solution is stable for at least four months. In particular embodiments, the composition has an oxygen content in the range of 0 µM to 5 µM, 0 µM to 3 µM, 0.01 µM to 1 µM, or 0.001 µM to 1 µM. In certain embodiments, the composition further comprises a halogen compound, such as, e.g., an iodide or a bromide, such as sodium iodide. Such a composition may further comprise glutathione or a goitrogen or other agent that impedes or inhibits thyroid hormone production, activity or uptake.

In certain embodiments, the composition is a sterile, stable pharmaceutical composition comprising: a solution of deoxygenated water and $Na_2S$, wherein the $Na_2S$ produces $HS^-$, wherein the solution has a pH in the range of 7.8 to 8.2; wherein the solution has an osmolarity in the range of 250-330 mOsmol/L; wherein the solution further comprises sulfide oxidation products selected from the group consisting of polysulfide, sulfite, sulfate and thiosulfate; wherein the oxidation products comprise sulfate in the range of (0%-1.0%), sulfite in the range of (0%-1.0%), polysulfide in the range of (0%-1%) or thiosulfate in the range of (0%-1.0%); wherein the solution is stable for at least four months; and, wherein the solution is isotonic or near isotonic. In certain embodiments, the composition further comprises a halogen compound, such as, e.g., an iodide or a bromide, such as sodium iodide. Such a composition may further comprise glutathione (or another compound that inhibits or impedes thyroid hormone production or activity or a goitrogen).

In certain embodiments, the composition is a sterile, stable, liquid pharmaceutical composition made by the steps, in any suitable order, comprising: making a solution of $Na_2S$ by rinsing $Na_2S.9H_2O$ crystals with deoxygenated, distilled and deionized water; bubbling $N_2$, a mixture of $N_2/CO_2$, or a mixture of $N_2/H_2S$ through the solution generating the $Na_2S$ that produces HS, and, adjusting the pH of the solution to a pH in the range of 7.5 to 8.5 by adding HCl to the solution; wherein said solution has an osmolarity in the range of 250-330 mOsmol/L; wherein said solution further comprises sulfide oxidation products selected from the group consisting of polysulfide, sulfite, sulfate and thiosulfate; wherein the oxidation products comprise sulfate in the range of (0%-1.0%), sulfite in the range of (0%-1.0%), polysulfide in the range of (0%-1%) or thiosulfate in the range of (0%-1.0%); and, wherein said composition is isotonic or near isotonic. In certain embodiments, the composition further comprises a halogen compound, such as, e.g., an iodide or a bromide, such as sodium iodide. Such a composition may further comprise glutathione or a goitrogen or other agent that impedes or inhibits thyroid hormone production, activity or uptake.

In various embodiments of the above compositions comprising a chalcogenide, the concentration of $HS^-$ is in the range of 1 mM to 250 mM, 10 mM to 200 mM or 95 mM to 150 mM. In one embodiment of the above compositions comprising a chalcogenide, the concentration of $HS^-$ is in the range of 1 mM to 250 mM, 10 mM to 200 mM or 95 mM to 150 mM. In one embodiment of the above compositions comprising a chalcogenide, the concentration of $HS^-$ is in the range of 1 mM to 250 mM, 10 mM to 200 mM or 95 mM to 150 mM.

The present invention further includes kits comprising composition(s) of the present invention. In certain embodiments, such kits comprise one or more containers to store the composition(s) of the present invention. In one embodiment, a composition is stored in the container under an inert or noble gas, and the container is a sealed and has an oxygen impermeable light-protective container (e.g., an amber vial). In certain embodiments, a kit comprises a composition comprising a halogen compound, e.g., a reduced form of iodine, such as iodided, and a composition comprising an active agent used to treat chronic heart failure.

In certain embodiments, a composition is packaged in an impermeable container. "Impermeable container" refers to containers that provide a barrier to the passage of gas molecules. Impermeable containers are known to those skilled in the art and include, but are not limited to, "i.v. bags" or syringes comprising a gas impermeable construction material, or a sealed glass vial. In particular embodiments, the composition may be packaged into an impermeable container containing an inert atmosphere, an inert gas, or a noble gas. Noble gas refers to helium (He), neon (Ne), argon (Ar), krypton (Kr), xenon (Xe), and radon (Rn). Inert gas refers to nitrogen (N2). The term "inert atmosphere" refers to a nitrogen or argon atmosphere in a container. In particular embodiments, the container comprises a reduced oxygen or oxygen-free environment. A "reduced oxygen environment" is an environment having an oxygen concentration of less than 100 parts per million. The composition may be packaged in a light-protective vial or container, e.g., amber vials. In one embodiment, the composition is sealed and stored in a glass ampoule.

In some embodiments, compositions of the present invention comprise one or more excipients included to prevent oxidation of the halogen compound and/or chalcogenide during storage, where storage is in the range of one to twelve months or longer. In some embodiments, storage is in the range of one to six months. In some embodiments, storage is in the range of three to six months. In some embodiments, storage is in the range of four to five months. Embodiments of the present invention may use a single excipient or a combination of excipients. There are many suitable excipients. Examples include chelators, pH modifying agents, reducing agents, antioxidants, spin-trap agents and preservatives.

In one embodiment, compositions of the present invention may optionally contain chelators or chelating agents. Chelating agents yielding soluble metal complexes are also called sequestering agents. A chelating agent typically has at least two functional groups that donate a pair of electrons to the metal, such as —O—, —NH$_2$ or —COO—. Examples of naturally-occurring chelators include carbohydrates, including polysaccharides, organic acids with more than one coordination group, lipids, steroids, amino acids and related compounds, peptides, phosphates, nucleotides, tetrapyrrole, ferrioxamines, ionophores, such as gramicidin, monensin, valinomycin, and phenolics. Examples of synthetic chelators include, but are not limited to, Diethylenetriaminepentaacetic acid (DTPA), Diethylenetriaminepentaacetic acid pentasodium salt (DTPA5), CaDTPAH, dimercaprol (BAL), deferoxamine, desferal, 2,2'-Bipyridyl Dimercaptopropano-lEthylenediaminetetraacetic acid, Ethylenedioxy-diethyl-ene-dinitrilo-tetraacetic acid (EDTA), CaNa2ethylenediaminetetraacetic acid, Ethylene glycol-bis-(2-aminoethyl)-N,N,N',N'-tetraacetic acid (EGTA), ionophores, Nitrilotriacetic acid (NTA), ortho-Phenanthroline, Salicylic acid, succimer (meso-2,3-dimercaptosuccinic acid, (DMSA), Triethanolamine (TEA), N-(2-Hydroxyethyl)ethylenediamine-N,N',N'-triacetic acid Trisodium salt (HEDTA), Nitrilotriacetic acid (NTA). In one embodiment, the synthetic chelator is DTPA. In certain embodiments, the concentration of DTPA is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M or any range derivable therein. In one embodiment, the DTPA is in the range of 0.1 mM to 50 mM. In one embodiment, the synthetic chelator consists of DTPA5. In certain embodiments, the concentration of DTPA5 is in the range of (0.0001%-0.1%) (w/v). In another embodiment, DTPA5 is in the range of (0%-1.0%) (w/v). In one embodiment, DTPA5 is in the range of (0% to 0.01%) (w/v). In one embodiment, the synthetic chelator is CaDTPA. In certain embodiments, the concentration of CaDTPA is in the range of (0.0001%-0.1%) (w/v). In one embodiment, CaDTPA is in the range of (0% to 0.01%) (w/v). In another embodiment, CaDTPA is in the range of (0%-1.0%) (w/v). In one embodiment, the synthetic chelator is deferoxamine. In certain embodiments, the concentration of deferoxamine is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein. In one embodiment, the deferoxamine is in the range of 0.1 mM to 10 mM. In one embodiment, the synthetic chelator is EDTA. In certain embodiments, the concentration of EDTA is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein. In a certain embodiment, EDTA is in the range of 0%-1% (w/v). In another embodiment, EDTA is in the range of 0.0001%-0.1% (w/v). In another embodiment, EDTA is in the range of 0%-1.0% (w/v). In one embodiment, EDTA is in the range of 0% to 0.01% (w/v).

Compositions of the present invention may further comprise one or more pH modifying agents. pH modifying agents, include, but are not limited to, inorganic salts, such as zinc carbonate, magnesium carbonate, calcium carbonate, magnesium hydroxide, calcium hydrogen phosphate, calcium acetate, calcium hydroxide, calcium lactate, calcium maleate, calcium oleate, calcium oxalate, calcium phosphate, magnesium acetate, magnesium hydrogen phosphate, magnesium phosphate, magnesium lactate, magnesium maleate, magnesium oleate, magnesium oxalate, sodium chloride, sodium carbonate, sodium bicarbonate, potassium hydroxide, potassium phosphate, sodium bicarbonate, thioglycolic acid, zinc acetate, zinc hydrogen phosphate, zinc phosphate, zinc lactate, zinc maleate, zinc oleate, zinc oxalate, and combinations thereof. Other pH modifying agents include, e.g., acetic acid, fumaric acid, malic acid, nitric acid, phosphoric acid, propionic acid, sulfuric acid, tartaric acid, carbon dioxide, carbonic acid, N-methyl-D-glucamine, 4-(2-hydroxyethyl)-morpholine, Tromethamine, Orotic acid, and hydrochloric acid. In one embodiment, the pH modifying agent is sodium hydroxide.

A pH modifying agent may serve as a buffering agent when it is added to an already acidic or basic solution, which it then modifies and maintains at a new pH (see: The United States Pharmacopeia-National Formulary 29th Edition, (2006) Rockville, Md.; Stahl, P. Wermuth, C. ed. Handbook of Pharmaceutical Salts Properties, Selection and Use. Wiley (2002)).

In certain embodiments, compositions of the present invention include one more excipients that are reducing agents, such as, e.g., glutathione (see: U.S. Pat. No. 6,586, 404), tris(2-carboxyethyl)phosphine hydrochloride (TSEP), I-cysteine, cysteine or methionine. In one embodiment, the reducing agent is glutathione (see: Vincent et al., Endocrine Reviews (2004) 25:612-628), dithiothreitol (DTT) (Weir et al., Respir and Physiol Biol; (2002) 132:121-30) or dithioerythritol (DTE). In certain embodiments, the concentration of glutathione is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M or more or any range derivable therein. In certain embodiments, the concentration of dithiothreitol (DTT), which present at about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or 1 M, or any range derivable therein. In certain embodiments, the reducing agent is dithioerythritol (DTE), is about, at least about, or at most about 0, 0.001, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 mM or M, or any range derivable therein.

Compositions of the present invention may optionally comprise a free radical scavenger or antioxidant. Examples of free radical scavengers or antioxidants include, but are not limited to, ascorbic acid (vitamin C), D-alpha tocopherol acetate, DL-alpha-tocopherol (vitamin E), melatonin, sodium bisulfite, sodium sulfite, sodium metabisulfite, Trolox (6-hydroxy-2,5,7,8-tetramethyl chroman-2-carboxylic acid), Tris(2-Carboxyethyl)phosphine Hydrochloride (TCEP), melatonin, dithionite, pyrosulfite, cysteine, potassium disulfite, sodium thioglycolate, thioethylene glycol, L-threoascobic acid, acetylsalicylic acid, salicylic acid, lecithin, ascorbyl palmitate, butylated hydroxyanidole, ascorbic acid, butylated hydroxyanisole, butylated hydroxyquinone, butylhydroxyanisol, hydroxycomarin, butylated hydroxytoluene, cephalm, ethyl gallate, propyl gallate, octyl gallate, lauryl gallate, propylhydroxybenzoate, trihydroxybutylrophenone, dimethylphenol, lecithin, ethanolamine, meglumine and combinations thereof (see US 2005/0106214). In one embodiment, the antioxidant agent is a spin-trap agent. Examples of spin-trap agents include, but are not limited to, N-t-butyl-phenylnitrone (PBN) (see: Kotake, Y., Antioxid Redox Signal (1999) 481), 4-Hydroxy-2,2,6,6-tetramethyl-piperidine-1-oxyl (TEMPOL) (Gariboldi, M. B., et al. (2000), Free Radic. Biol. Med. 29:633; Miura, Y., et al. J. Radiat. Res. (Tokyo) (2000) 41:103; Mota-Filipe, H., et al. (1999), Shock 12:255R: 22-41; S: 39-26 2,2,6,6-tetramethylpiperidine-N-oxyl (TEMPO) (see: Lapchak, et al., Stroke (2001) 32:147-53); (disodium-[(tert-butylimino)methyl] benzene-1,3-disulfonate N-oxide (NXY-059) (see: Lapchak et al., CNS Drug Rev (2003) 9:253-62). In some embodiments, the spin-trap agent is TEMPO, which is present in the range of 0 mg/kg-1,000 mg/kg. In some embodiments, the spin-trap agent is TEMPO and is present in the range of 100 mg/kg-1,000 mg/kg. In another embodiment, the spin-trap agent is TEMPO and is present in the range of 0 mg/kg-100 mg/kg.

Composition of the present invention may optionally comprise a preservative. As used herein, the term "preservative" is intended to mean a compound used to prevent the growth of microorganisms. Such compounds by way of example and without limitation, include benzalkonium chloride, benzethonium chloride, benzoic acid, benzyl alcohol, butylated hydroxyanisole (BHA), cetrimonium bromide, cetylpyridinium chloride, chlorobutanol, chlorocresol, cresol, methylparaben sodium, phenol, pheenoxyethanol, phenylethyl alcohol, phenylmercuric acetate, phenylmercuric nitrate, phenylmercuric acetate, thimerosal, metacresol, myristylgamma picolinium chloride, potassium benzoate, potassium sorbate, sodium benzoate, sodium propionate, sorbic acid, thioglycerol, thimerosal, thymol, and methyl, ethyl, propyl or butyl parabens and others known to those of ordinary skill in the art. Such preservatives are used in stable compositions at typical concentrations in accordance with acceptable pharmaceutical practices, such as described. (see: The United States Pharmacopeia—National Formulary 29th Edition, (2006) Rockville, Md.; Remington's Pharmaceutical Sciences (2005) 21st Edition, Troy, D B, Ed. Lippincott, Williams and Wilkins). In a certain embodiment, the preservative is benzyl alcohol and is present in the range of 0%-1.0% (w/v). In one embodiment, the preservative is benzyl alcohol and is present in the range of 0%-0.5% (w/v). In one embodiment, the preservative is phenol in the range of 0%-0.5% (w/v). In a certain embodiment, the preservative is methyl paraben in the range of (0.0%-0.25% (w/v). In a certain embodiment, the preservative is ethyl paraben in the range of 0%-0.25% (w/v). In a certain embodiment, the preservative is propyl paraben in the range of 0%-0.25% (w/v). In a certain embodiment, the preservative is butyl paraben, in the range of 0%-0.4% (w/v). In a certain embodiment, the preservative is benzalkonium chloride in the range of 0%-0.02% (w/v).

In particular embodiments, any of the compositions of the present invention comprise may comprise both a reduced form of a halogen compound and a reduced form of a chalcogenide. In addition, a composition may comprise two or more halogen compounds and/or two or more chalcogenides.

The present invention also includes unit dosage forms of compositions of the present invention. In certain embodiments, the unit dosage form comprises or consists of an effective amount of a halogen compound for treating or preventing a disease, condition, or injury, including any of those described herein, in a subject in need thereof. In certain embodiments, the unit dosage form comprises or consists of an effective amount of a chalcogenide for treating or preventing a disease, condition, or injury, including any of those described herein, in a subject in need thereof. In certain embodiments, a unit dosage form further comprises glutathione in an amount effective to maintain the chalcogenide and/or halogen compound in a reduced form under any of the conditions described herein. In particular embodiments, the unit dosage form is formulated for intravenous administration, administration by infusion, or oral administration. In certain embodiments, as used herein, the term "prevention" includes inhibiting or impeding the onset or progression of a disease or injury, or reducing the amount of injury or damage caused by a disease or injury.

In particular embodiments, a unit dosage form comprising a halogen compound, such as an iodide or NaI, comprises or consists of about 0.005 mg to about 5000 mg, about 0.05 to about 1000 mg, about 0.5 mg to about 100 mg, about 1 mg to about 100 mg, about 2.5 mg to about 100 mg, about 0.5 mg to about 50 mg, about 1 mg to about 50 mg, about 2.5 mg to about 50 mg, about 5 mg to about 50 mg, about 10 mg to about 50 mg, or about 1 mg, about 2 mg, about 5 mg, about 10 mg, or about 15 mg. In related embodiments, the unit dosage form comprises less than or equal to 150 mg, less than or equal to 125 mg, less than or equal to 100 mg, less than or equal to 75 mg, less than or equal to 50 mg, less than or equal to 25 mg, or less than or equal to 10 mg of the halogen compound. In certain embodiments, the unit dosage form comprises between about 1 mg and about 150 mg (including any interval in this range), between about 1 mg and about 125 mg, between about 1 mg and about 100 mg, between about 1 mg and about 75 mg, between about 1 mg and about 50 mg, between about 1 mg and about 25 mg or between about 1 mg and about 10 mg of the halogen compound. In certain embodiments, the unit dosage form comprises about 150 mg, about 125 mg, about 100 mg, about 75 mg, about 50 mg, about 25 mg or about about 10 mg of the halogen compound. In certain embodiments, the unit dosage form comprises less than or equal to 1000 mg, less than or equal to 800 mg, less than or equal to 700 mg, less than or equal to 500 mg, less than or equal to 250 mg, less than or equal to 200 mg, or less than or equal to 150 mg of the halogen compound. In certain embodiments, the unit dosage form comprises between about 100 mg and about 1000 mg (including any interval in this range), between about 150 mg and about 800 mg, between about 200 mg and about 700 mg, between about 250 mg and about 600 mg, between about 300 mg and about 500 mg, between about 350 mg and about 450 mg or between about 300 mg and about 700 mg of the halogen compound. In certain embodiments, the unit dosage form comprises about 200 mg, about 300 mg, about 400 mg, about 500 mg, about 600 mg, about 700 mg, about 800 mg, about 900 mg, or about about 1000 mg of the halogen compound.

In some embodiments, including, e.g., embodiments where the unit dosage form is formulated as a liquid, e.g., for intravenous administration or administration by infusion, the concentration of halogen compound or salt or precursor thereof present in a unit dosage form of the present invention is about 0.0001 mM to about 100 M, about 0.0005 mM to about 50 M, about 0.001 mM to about 10 M, about 0.001 mM to about 5 M, about 0.001 mM to about 1 M, about 0.005 mM to about 10 M, about 0.005 mM to about 5 M, about 0.005 mM to about 1 M about 0.005 mM to about 0.5 M, about 0.01 mM to about 10 M, about 0.01 mM to about 5 M, about 0.01 mM to about 2 M, about 0.1 mM to about 1 M, about 0.1 mM to about 0.5 M, about 0.5 mM to about 5 M, about 0.5 mM to about 2 M, about 0.5 mM to about 1

M, about 0.5 mM to about 0.5 M, about 1 mM to about 5 M, about 1 mM to about 2 M, about 1 mM to about 1 M, about 1 mM to about 0.5 M, about 5 mM to about 5 M, about 5 mM to about 2 M about 5 mM to about 1 M, about 5 mM to about 0.5 M, about 5 mM to about 0.25 M, about 10 mM to about 1 M, about 10 mM to about 0.5 M, about 10 mM to about 0.25 M, or about 10 mM, about 50 mM about 100 mM, or about 200 mM. The unit dosage form may further comprise one or more pharmaceutically acceptable diluents, excipients or carriers.

In certain embodiment, the unit dosage form comprises iodine, e.g., NaI, and the effective amount is greater than or equal to about 150 µg, greater than or equal to about 300 µg, greater than or equal to about 500 µg, greater than or equal to about 1 mg, greater than or equal to about 2 mg, greater than or equal to about 5 mg, greater than or equal to about 10 mg, greater than or equal to about 15 mg, or greater than or equal to about 20 mg. In certain embodiments, the effective amount is 150 µg to 1000 mg, 300 µg to 1000 mg, 500 µg to 1000 mg, 1 mg to 1000 mg, 2 mg to 1000 mg, 5 mg to 1000 mg, 10 mg to 1000 mg, 150 µg to 100 mg, 300 µg to 100 mg, 500 µg to 100 mg, 1 mg to 100 mg, 2 mg to 100 mg, 5 mg to 100 mg, or 10 mg to 100 mg. In certain embodiments, the effective amount is 150 µg to 50 mg, 300 µg to 20 mg, 500 µg to 10 mg, 1 mg to 20 mg, 1 mg to 10 mg, or about 5 mg, about 10 mg, about 15 mg, or about 20 mg. In other embodiments, the effective amount is between about 1 mg and about 150 mg (including any interval in this range), between about 1 mg and about 125 mg, between about 1 mg and about 100 mg, between about 1 mg and about 75 mg, between about 1 mg and about 50 mg, between about 1 mg and about 25 mg or between about 1 mg and about 10 mg of the halogen compound. In certain embodiments, the effective amount is about 150 mg, about 125 mg, about 100 mg, about 75 mg, about 50 mg, about 25 mg or about about 10 mg of the halogen compound. In certain embodiments, the effective amount comprises less than or equal to 1000 mg, less than or equal to 800 mg, less than or equal to 700 mg, less than or equal to 500 mg, less than or equal to 250 mg, less than or equal to 200 mg, or less than or equal to 150 mg of the halogen compound. In certain embodiments, the effective amount is between about 100 mg and about 1000 mg (including any interval in this range), between about 150 mg and about 800 mg, between about 200 mg and about 700 mg, between about 250 mg and about 600 mg, between about 300 mg and about 500 mg, between about 350 mg and about 450 mg or between about 300 mg and about 700 mg of the halogen compound. In certain embodiments, the effective amount is about 200 mg, about 300 mg, about 400 mg, about 500 mg, about 600 mg, about 700 mg, about 800 mg, about 900 mg, or about about 1000 mg of the halogen compound. In particular embodiments, the effective amount is the amount per day.

In certain embodiments, a unit dosage form comprises or consists of an effective amount of a chalcogenide for treating or preventing a disease, condition, or injury, including any of those described herein, in a subject in need thereof. In particular embodiments, a unit dosage form of a chalcogenide comprises about 0.005 mg to about 5000 mg, about 0.05 mg to about 5000 mg, about 0.1 mg to about 5000 mg, about 0.005 mg to about 2000 mg, about 0.05 mg to about 2000 mg, about 0.1 mg to about 2000 mg, about 0.5 mg to about 2000 mg, about 1 mg to about 1000 mg, about 2 mg to about 500 mg, about 5 mg to about 500 mg, about 10 mg to about 100 mg, about 10 mg, about 20 mg, about 50 mg, about 60 mg, about 70 mg, about 80 mg, about 100 mg, or about 150 mg.

In certain embodiments, the unit dosage form comprises or consists of an effective amount of both a halogen compound and a chalcogenide, wherein the halogen compound and chalcogenide are present in the unit dosage form in an amount useful for treating or preventing a disease, condition, or injury, including any of those described herein, in a subject in need thereof. It is understood that the effective amount of each of the halogen compound and chalcogenide may be different when they are used in combination as compared to when they are used individually.

In certain embodiments, the unit dosage form comprises or consists of an effective amount of both a halogen compound and an active agent used to treat chronic heart failure, wherein the halogen compound and the active agent are present in the unit dosage form in an amount useful for treating or preventing a disease, condition, or injury, such as chronic heart failure, in a subject in need thereof. It is understood that the effective amount of each of the halogen compound and chalcogenide may be different when they are used in combination as compared to when they are used individually.

In certain embodiments, the unit dosage form comprises or consists of an effective amount of a composition comprising both a chalcogenide and glutathione, a composition comprising both a halogen compound and glutathione, or a composition comprising all of a halogen compound, a chalcogenide, and glutathione, wherein the halogen compound (if present) and chalcogenide (if present) are present in the composition in an amount useful for treating or preventing a disease, condition, or injury, including any of those described herein, in a subject in need thereof. The glutathione may be present in an amount sufficient to inhibit oxidation of the chalcogenide and/or halogen compound. It is understood that the effective amount of each of the halogen compound and chalcogenide may be different when they are used in combination as compared to when they are used individually. In certain embodiments, the composition comprises about 15 mM to about 500 mM glutathione or about 10 mM to about 500 mM glutathione.

In certain embodiments, a composition of the invention may be formulated in a dosage form suitable for oral or parenteral administration. In addition, in particular embodiments, a composition of the invention may be in the form of an immediate or modified release formulation. For example, formulations of the halogen compound and/or chalcogenide can be used to provide controlled release, in which the release of the compound(s) is controlled and regulated to allow less frequency of dosing or to improve the pharmacokinetic or toxicity profile of a given active agent.

In general the amount of the active compound present in a composition or unit dosage form depends inter alia on the specific compound and formulation, the age and condition of the subject, and the injury, condition, or disease being treated or prevented, the route of administration and the dosage frequency.

The dosage frequency also depends on the injury, condition or disease being treated or prevented, the amount or concentration of the compound, the specific composition used, the route of administration and may incorporate subject-specific variation including, but not limited to age, weight, gender, or overall health. For example, an oral composition may be administered prior to surgery to prevent ischemia/reperfusion injury during or post-surgery, in which case it may be administered one or more times prior to surgery, optionally in either an immediate or modified or controlled release formulation. In other situations, for example, an oral or intravenous composition may be administered following injury or the occurrence of a medical condition (e.g., stroke or heart attack), in which case it may be advantageous to use an immediate release formulation to achieve a relatively fast onset of treatment or prevention of ischemia/reperfusion injury at the site of injury or medical condition.

In certain embodiments, a unit dosage form suitable for oral administration is in the form of a pill, drenches (aqueous or non-aqueous solutions or suspensions), boluses, powders, granules, polymer release formulations, pastes for application to the tongue tablet, caplet or a capsule. A pill is a small, round, solid pharmaceutical oral dosage form that was in use before the advent of tablets and capsules. In colloquial usage, tablets, capsules, and caplets are still often referred to as "pills" collectively. In certain embodiments, pills are made by mixing the active ingredients with an excipient such as glucose syrup in a mortar and pestle to form a paste, then divided into suitable sizes, and often coated with sugar to make them more palatable.

A tablet is a pharmaceutical dosage form that comprises a mixture of active substances and excipients, usually in powder form, pressed or compacted from a powder into a solid dose. The excipients can include diluents, binders or granulating agents, glidants (flow aids) and lubricants to ensure efficient tabletting; disintegrants to promote tablet break-up in the digestive tract; sweeteners or flavours to enhance taste; and pigments to make the tablets visually attractive, etc. A polymer coating is often applied to make the tablet smoother and easier to swallow, to control the release rate of the active ingredient, or to make it more stable. Sizes of tablets to be swallowed typically range from a few millimeters to about a centimeter. Some tablets are in the shape of capsules, and are called "caplets".

Capsules may be in the form of hard-shelled capsules, which are normally used for dry, powdered ingredients or miniature pellets, or soft-shelled capsules, which are primarily used for oils and for active ingredients that are dissolved or suspended in oil. In certain embodiments, capsules are made from aqueous solutions of gelling agents such as gelatin or plant polysaccharides. Other ingredients can be added to the gelling agent solution, such as plasticizers such as glycerin and/or sorbitol to decrease the capsule's hardness, coloring agents, preservatives, disintegrants, lubricants and surface treatment.

Dosage levels of a halogen compound and/or chalcogenide present in a composition described herein may be varied as so to obtain an amount of the halogen compound and/or chalcogenide that is effective to achieved the desired therapeutic effect for a particular subject, halogen compound, chalcogenide, and mode of administration, without being toxic to the subject.

In certain embodiments, a unit dosage form of a composition of the invention formulated for oral delivery, e.g., a pill, tablet, caplet, or capsule, comprises or consists of about 0.005 mg to about 5000 mg, about 0.05 to about 1000 mg, about 0.5 to about 500 mg, about 0.5 to about 250 mg, about 0.5 mg to about 100 mg, about 1 mg to about 500 mg, about 1 to about 250 mg, about 1 mg to about 125 mg, about 1 mg to about 120 mg, about 1 to about 100 mg, about 2.5 mg to about 250 mg, about 2.5 to about 100 mg, about 0.5 mg to about 50 mg, about 1 mg to about 50 mg, about 2.5 mg to about 50 mg, about 5 mg to about 50 mg, about 10 mg to about 50 mg, about 1 to about 15 mg, about 1 to about 10 mg, or about 1 mg, about 2 mg, about 5 mg, about 10 mg, or about 15 mg of a halogen compound, such as an iodide or NaI. The unit dosage form may further comprise a pharmaceutically acceptable carrier, excipient or diluent.

In particular embodiments, a unit dosage form of a composition of the invention formulated for oral delivery, e.g., a pill, tablet, caplet, or capsule, comprises or consists of less than 150 mg, less than 140 mg, less than 130 mg, less than 120 mg, less than 110 mg, less than 100 mg, less than 90 mg, less than 80 mg, less than 70 mg, less than 60 mg, less than 50 mg, less than 40 mg, less than 30 mg, less than 20 mg, less than 10 mg, or less than 5 mg of a halogen compound, such as an iodide or NaI. The unit dosage form may further comprise a pharmaceutically acceptable carrier, excipient or diluent.

In certain embodiments, a unit dosage form may comprise a chalcogenide, alone or in combination with another active agent, such as a halogen compound. In specifically embodiments, the chalcogenide, e.g., sulfide or selenide, is present in the unit dosage form in the amount of about 0.005 mg to about 5000 mg, about 0.05 mg to about 5000 mg, about 0.1 mg to about 5000 mg, about 0.005 mg to about 2000 mg, about 0.05 mg to about 2000 mg, about 0.1 mg to about 2000 mg, about 0.5 mg to about 2000 mg, about 1 mg to about 1000 mg, about 2 mg to about 500 mg, about 5 mg to about 500 mg, about 10 mg to about 100 mg, about 10 mg, about 20 mg, about 50 mg, about 60 mg, about 70 mg, about 80 mg, about 100 mg, or about 150 mg.

In particular embodiments of unit dosage forms suitable for oral administration, the unit dosage form comprises both a halogen compound and a chalcogenide. In certain embodiments, both the halogen compound and the chalcogenide, e.g., sulfide or selenide, are in a reduced form. In one embodiment, the unit dosage form comprises a solid outer layer comprising the halogen compound, e.g., iodine, surrounding or encapsulating an inner region comprising a liquid solution comprising the chalcogenide. In particular embodiments, the unit dosage form comprises a solid outer layer encapsulating an inner liquid region comprising the halogen compound and the chalcogenide. In certain embodiments, the encapsulated chalcogenide is protected from oxidation by the solid outer layer. In certain embodiments, the active agents are comingled at the molecular level.

In particular embodiments of unit dosage forms suitable for oral administration, the unit dosage form comprises both glutathione and a chalcogenide. In certain embodiments, the chalcogenide, e.g., sulfide or selenide, is in a reduced form. In certain embodiments, the unit dosage form further comprises a halogen compound. In certain embodiments, the agents are comingled at the molecular level.

In particular embodiments of unit dosage forms suitable for oral administration, the unit dosage form comprises both glutathione and a halogen compound. In certain embodiments, the halogen compound, e.g., iodine, is in a reduced form, e.g., iodide or iodate. In certain embodiments, the unit dosage form further comprises a chalcogenide compound. In certain embodiments, the agents are comingled at the molecular level.

In various embodiments, compositions and unit dosage forms of the invention may be formulated in any different manner suitable for a desired delivery route. Typically, formulations include all physiologically acceptable compositions. Such formulations may include a halogen compound, alone or in combination with another active agent, such as a chalcogenide, in combination with any physiologically acceptable carrier, diluent or excipient. Such formulations may include a chalcogenide, alone or in combination with another active agent, such as a halogen compound, in combination with any physiologically acceptable carrier, diluent or excipient. Halogen compounds and/or chalcogenides may be formulated for administration with any biologically acceptable medium, including but not limited to water, buffered saline, polyol, or mixtures thereof. "Biologically acceptable medium" includes any and all solvents, dispersion media, and the like that may be appropriate for the desired route of administration of the pharmaceutical composition. Suitable biologically acceptable media and their formulations are described, for example, in the most recent Remington's Pharmaceutical Sciences (Remington's Pharmaceutical Sciences. Mack Publishing Company, Easton, Pa., USA 1985).

Formulations, and unit dosages forms thereof, may contain suitable physiologically acceptable carriers comprising excipients and/or auxiliaries that facilitate processing of the halogen compound and/or other active agent into preparations that can be used pharmaceutically. Formulations, and unit dosage forms thereof, may also include agents that increase or otherwise affect the bioavailability of the halogen compound and/or other active agent. As used herein, "bioavailability" refers to the effect, availability and persistence of the active agent(s) after being administered to a subject.

Pharmaceutically acceptable carriers can be any pharmaceutically acceptable material, composition, or vehicle, including but not limited to a liquid or solid filler, diluent, excipient, solvent or encapsulating material, involved in carrying or transporting the subject agonists to an organ, or portion of the body. Each carrier must be compatible with the other ingredients of the formulation and not injurious to the subject. Some examples of materials which can serve as pharmaceutically acceptable carriers include but are not limited to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

Formulations can also include wetting agents; emulsifiers and lubricants such as sodium lauryl sulfate and magnesium stearate; coloring agents; release agents; coating agents; sweetening, flavoring, and/or perfuming agents; preservatives; and antioxidants. Formulations may also incorporate buffering agents and/or salts to aid absorption or stabilize the halogen compound and/or chalcogenide. Other additives, such as chelating agents, enzymatic inhibitors, and the like, which would facilitate the biological activity of the pharmaceutical composition may also be incorporated in the formulation.

The formulations may be presented in a unit dosage form and may be prepared by any methods known in the art. The amount of halogen compound that can be combined with a carrier to produce a single dosage form will generally be that amount of the halogen compound that produces a therapeutic effect.

Formulations suitable for oral administration may be in the form of a solid (capsules, cachets, pills, tablets, lozenges, powders, dragees, granules); or as a solution or a suspension in an aqueous or non-aqueous liquid; or as an oil-in-water or water-in-oil liquid emulsion; or as an elixir or syrup; or as pastilles (using an inert base, such as gelatin and glycerin, or sucrose and acacia); and/or as mouth rinses or washes and the like; or as a bolus, electuary or paste.

Solid formulations may have pharmaceutically acceptable carriers and extenders including but not limited to sodium citrate or dicalcium phosphate; starches; lactose; sucrose; glucose; mannitol; and/or silicic acid. Solid formulations can include additional components including but not limited to binders such as carboxymethylcellulose, alginates, gelatin, polyvinyl pyrrolidone, sucrose and/or acacia; humectants such as glycerol; disintegrating agents such as agar-agar, calcium carbonate, potato or tapioca starch, alginic acid, certain silicates, and sodium carbonate; solution retarding agents such as paraffin; absorption accelerators such as quaternary ammonium compounds; wetting agents such as cetyl alcohol and glycerol monostearate; absorbents such as kaolin and bentonite clay; lubricants such a talc, calcium stearate, magnesium stearate, solid polyethylene glycols, sodium lauryl sulfate, and mixtures thereof; and coloring agents. The formulation may also include buffering agents, particularly when the halogen compound and/or chalcogenide is in the form of a capsule, tablet or pill.

Solid formulations may also include fillers for soft and hard-filled gelatin capsules using excipients such as lactose or milk sugars, as well as high molecular weight polyethylene glycols and the like.

Solid formulations of compositions described herein, such as dragees, capsules, pills and granules, may optionally be scored or prepared with coatings and shells, such as enteric coatings and other coatings. Solid dosage forms may also be formulated so as to provide slow or controlled release of the agent agent(s). Thus, solid formulations could include any material that could provide a desired release profile of the active agent(s), including but not limited to hydroxypropylmethyl cellulose in varying proportions, or other polymer matrices, liposomes and/or microspheres. Formulations of may also be formulated by including an embedding agent. Examples of embedding agents which can be used include but are not limited to polymeric substances and waxes. The halogen compound and/or chalcogenide may also be in microencapsulated form, if appropriate, with one or more of the above-described excipients.

Liquid dosage formulations for oral administration of the halogen compound and/or chalcogenide may include pharmaceutically acceptable emulsions, microemulsions, solutions, suspensions, syrups and elixirs. In addition to the halogen compound and/or chalcogenide, the liquid dosage formulations may contain inert diluents commonly used in the art, including but not limited to water or other solvents; solubilizing agents and emulsifiers, such as ethyl alcohol, isopropyl alcohol, ethyl carbonate, ethyl acetate, benzyl alcohol, benzyl benzoate, propylene glycol, 1,3-butylene glycol; oils (in particular, cottonseed, groundnut, corn, germ, olive, castor and sesame oils); glycerol; tetrahydrofuryl alcohol; polyethylene glycols; and fatty acid esters of sorbitan, and mixtures thereof.

The present invention further includes stable liquid pharmaceutical compositions formulated for parenteral administration, e.g., intravenous administration or administration by infusion. In certain embodiments, the stable liquid pharmaceutical compositions comprise a reduced form of a chalcogenide and/or a reduced form of a halogen compound. In particular embodiments, the composition further comprises glutathione. In other embodiments, a stable liquid pharmaceutical compositions formulated for parenteral administration comprises a goitrogen or a compound that inhibits or impedes thyroid hormone synthesis, activity or uptake. In particular embodiments, a stable liquid pharmaceutical compositions formulated for parenteral administration comprises a chalcogenide, e.g., selenide, and glutathione. In particular embodiments, a stable liquid pharmaceutical compositions formulated for parenteral administration comprises a halogen compound, e.g., iodide, and glutathione. In particular embodiments, a stable liquid pharmaceutical compositions formulated for parenteral administration comprises selenide, iodide, and glutathione. The selenide, iodide and glutathione may be present at a concentration described herein, or in amount sufficient or appropriate to deliver an amount described herein to a subject. The concentration of each active agent in the composition may be readily determined based on the desired amount of each active agent to be delivered to a subject in need thereof.

In particular embodiments, a composition of the invention comprises a chalcogenide, a halogen compound, and glutathione. In certain embodiments, the chalcogenide is sulfide or selenide (or a reduced form thereof), and the halogen compound is iodide or iodate. In particular embodiments, the chalcogenide is selenide. In particular embodiments, the halogen compound is iodide. Thus, in one embodiment, a composition of the present invention comprises selenide, iodide and glutathione. The composition may be formulation for intravenous administration or administration by infusion. The composition may be formulated as a stable composition for intravenous administration or administration by infusion. In particular embodiments, the composition comprises selenide at a concentration of about 1 mM to about 1 M or about 10 mM to about 500 mM, iodide at a concentration of about 1 mM to about 1M or about 10 mM to about 500 mM, and glutathione at a concentration of about 1 mM to about 500 mM or about 10 mM to about 500 mM. In particular embodiments, the composition is contained within an oxygen-impermeable container, and may be under nitrogen or argon gas. In particular embodiments, the amount of composition present in the container is a unit dosage amount comprising or consisting of a suitable dosage amount for administration to a subject in need thereof.

Formulations of halogen compound and/or chalcogenides for parenteral administration may comprise a halogen compound and/or a chalcogenide in combination with one or more pharmaceutically acceptable isotonic aqueous or non-aqueous solutions, dispersions, suspensions or emulsions, or powders which may be reconstituted into sterile injectable solutions or dispersions just prior to use. Parenteral formulations may contain antioxidants; buffers or solutes which render the formulation isotonic with the blood of the intended subject; bacteriostats; suspending; or thickening agents.

Injectable depot formulations comprising a halogen compound and/or a chalcogenide can be made by forming microencapsulated matrices of the halogen compound and/or chalcogenides in biodegradable polymers. Examples of biodegradable polymers include, but are not limited to polylactide-polyglycolide, poly(orthoesters) and poly(anhydrides). The ratio of active agent to polymer and the nature of the particular polymer employed can affect the rate of active agent release. Depot injectable formulations can also be prepared by entrapping the drug in liposomes or microemulsions.

The present invention further includes kits comprising compositions or unit dosage forms of the present invention. In certain embodiments, such kits comprise one or more containers to store the compositions of the present invention. In one embodiment, the composition is stored in the container under an inert or noble gas, and the container is a sealed and has an oxygen impermeable light-protective container (e.g., an amber vial).

In particular embodiments, a composition of the present invention comprises a carrier. In certain embodiments, the halogen compound is associated with the carrier, and in other embodiments, both the halogen compound and one or more additional active agents present in the composition are also associated with the carrier. The halogen compound and one or more additional active agents may be associated covalently or non-covalently. In certain embodiments, the carrier is a biocompatible carrier, which may be, e.g., biodegradable or inert. In certain embodiments, the carrier is a polypeptide, such as, e.g., an albumin, e.g., human albumin. Examples of other carriers that may be used according to the present invention include, but are not limited to plasma, serum, alpha-2-macroglobulin, and immunoglobulin.

Methods of Preparing Compositions

Compositions comprising halogen compounds, including reduced forms of halogen compounds, such as iodide and bromide, may be prepared by any means known and available. In certain embodiments, a halogen compound is dissolved in water or a suitable buffer, such as a NaCl buffer.

Certain chalcogenide compounds (e.g., hydrogen sulfide, hydrogen selenide), are not stable in the presence of oxygen due to their ability to react chemically with oxygen, leading to their oxidation and chemical transformation. Accordingly, oxygen may be removed from solutions used in these methods, using methods known in the art, including, but not limited to, application of negative pressure (vacuum degassing) to the or solution, or contacting the solution with a reagent which causes oxygen to be bound or "chelated", effectively removing it from solution. In general, methods of preparing compositions used according to the present invention may include limiting oxygen content in each aspect of manufacturing and storage.

WO2008/043081 describes methods of preparing stable, liquid compositions comprising chalcogenides or salts thereof, including those comprising reduced forms of chalcogenides.

U.S. Provisional Application No. 61/159,311 also describes methods of preparing a composition comprising a reduced form of a chalcogenide, e.g., a chalcogenide comprising selenium or sulfur is the −2 valence state, e.g., selenide or sulfide.

In particular embodiments of any of the methods of producing a stable composition described herein, the reduced form of the chalcogenide is in the minus 2 oxidation or valence state. In certain embodiments, the reduced form of the chalcogenide is $H_2Se$, $Na_2Se$, NaHSe, or HSe— anion.

In one embodiment, a composition comprising a reduced form of a chalcogenide is produced as follows: admixing a chalcogen, or an acid of a chalcogen, and a reducing agent in a reduced oxygen environment under conditions and for a time period sufficient to allow oxidation of a majority of the reducing agent and reduction of a majority of the chalcogen. In certain embodiments, the conditions include a temperature of about room temperature. In particular embodiments, the time period is about one hour, about two hours, about three hours, or overnight, e.g., about 12 hours. In particular embodiments, the time period is finished or ends when the admixture solution appears visibly clear or bubbling (due to hydrogen generation from the borohydride reacting with water) ceases or is no longer observed.

In particular embodiments, the chalcogen is sulfur or selenium, and the reduced form of a chalcogenide comprises sulfur or selenium in the −2 oxidation state. In certain embodiments, the acid of a chalcogen is selenous acid or sodium selenite or elemental selenium, and the reduced form of a chalcogenide comprises sulfur or selenium in the −2 oxidation state.

In particular embodiments, the reducing agent has a reduction potential)(E° less than or equal to about 0.4 V. In one embodiment, the reducing agent is sodium borohydride ($NaBH_4$). In certain embodiments, the molar ratio of the reducing agent to the chalcogen, or the acid of a chalcogen, is about 5:1 to about 0.5:1, or about 3:1 to about 1:1. In one embodiment, the molar ratio of the reducing agent to the chalcogen, or the acid of a chalcogen, is about 2:1.

In particular embodiments, the reducing agent is sodium borohydride, said chalcogen is sulfur or selenium, and said acid of a chalcogen is selenious acid. In one particular embodiment, the reducing agent is sodium borohydride, the chalcogen is selenium, and the molar ratio of sodium borohydride to selenium is about 2:1. In particular embodiments, the selenium is present in an amount of about 1 mM to about 10 M, or about 1 mM to 1M (79 mg/L to 79 g/L). In particular embodiments, the sodium borohydride is present in a 1M solution in water.

In certain embodiment, the method is performed in a reduced oxygen or oxygen-free environment. In certain embodiments, the method is performed under an inert or noble gas. In certain embodiments, the method is performed under nitrogen. For example, the nitrogen may be perfused into said reduced oxygen environment. In certain embodiments, the nitrogen is perfused at a rate of about 100 cc/min. In particular embodiments, the reduced oxygen environment is a container having an oxygen-free environment. In particular embodiments, the container is a syringe, i.v. bag, tube or a vial. In certain embodiments, the container comprises a closable port of entry or a resealable port. In one embodiment, the container is a sealable tube comprising a rubber septum, e.g., a Hungate tube.

In particular embodiments of this method, the perfusion of nitrogen into and out of the container, e.g., tube, occurs via two needles that pass through the septum of the container, wherein one of the two needles is used as the port to bring nitrogen into the tube, and wherein the second of the two needles is used to take nitrogen out of the tube.

In particular embodiments, the method further includes heating the admixture after said time period. In particular embodiments, the heating is continued until any observed bubbling ceases. The methods may also include cooling the admixture after the heating. Cooling may be performed, e.g., by placing the admixture on ice. In certain embodiments, cooling is continued until sodium borate precipitates from the admixture solution.

These methods may also further comprise centrifuging the admixture solution to separate a supernatant from the precipitated sodium borate, and removing said supernatant, wherein the supernatant comprises said stable composition comprising said reduced chalcogenide.

In particular embodiments, the methods comprise acidifying the admixture with an acid, wherein said acid is reducing and not volatile, and bubbling hydrogen selenide gas or hydrogen sulfide gas through a solution, wherein the solution has a pH greater than 3.9. Without wishing to be bound to any particular theory, it is believed that if a non volatile acid (e.g. phosphorus acid) is added to a solution of reduced chalcogenide that may have unwanted non volatile compounds in the solution, it will lower the pH to a value less than the pK for the chalcogenide, thus producing a gas form (e.g. $H_2S$ or $H_2Se$). The gas form is able to be blown out of the solution by passing nitrogen through the mixture and carried to a second solution that has a pH above the pK rendering the chalcogenide into an ionic form that is no longer a gas (i.e. trapping the chalcogenide).

In certain embodiment, the acid is phosphorous acid and said solution is phosphate buffered saline (PBS). This permits the hydrogen selenide or hydrogen sulfide gas to be trapped in a vessel.

In another embodiments, the present invention includes another method of producing a composition comprising a reduced form of a chalcogenide, the method comprising admixing elemental selenium (Se) or sulfur (S) and sodium hydride in a solution comprising mineral oil or tetrahydrofuran (THF), thereby producing a stable composition comprising sodium hydroselenide or sodium sulfide. In certain embodiments, the method also comprises adding water to the admixture solution, thereby removing sodium hydride. In particular embodiments wherein the solution comprises mineral oil, the method further comprises removing the aqueous phase of the admixture solution, wherein the reduced chalcogenide is present in the aqueous phase. In particular embodiments wherein the solution comprises THF, the method further comprises removing said THF by boiling said admixture solution at about 70° C.

In various embodiments, methods of preparing compositions of the present invention further include adjusting the pH of the composition. In certain embodiments, the pH is adjusted by the addition of one or more of hydrogen chloride, carbon dioxide, nitrogen, or hydrogen sulfide. In another embodiment, the pH is adjusted by dissolving nitrogen, carbon dioxide, hydrogen selenide, or hydrogen sulfide into the composition or any combination thereof.

In certain embodiments, once produced, in various embodiments, a composition is stored in an impermeable container, e.g., an oxygen impermeable container. This is particularly desirable to prevent oxidation of the reduced form of halogen compound or chalcogenide. Impermeable containers are known to those skilled in the art and include, but are not limited to, "i.v. bags" comprising a gas impermeable construction material, or a sealed glass vial. In particular embodiments, the impermeable container comprises an oxygen impermeable material having an oxygen transmission coefficient less than $10^{-10}$ [$cm^3$(STP)/cm/($cm^2$+s+Pa)], wherein STP=standard temperature and pressure (25 degrees centigrade and pressure 1 atmosphere); PA=pascals, and s=second. For example, the walls of the container may comprise a layer of an oxygen impermeable polymer. Exemplary oxygen impermeable polymers include but are not limited to: silicon rubber, natural rubber, low density poly ethylene (LDPE), polystyrene (PS), polyethylene (PE), polycarbonate (PC), polyvinyl acetate (PVAc), amorphous polyethylene terephthalate (APET), polyvinly chloride (PVC), nylon 6 (Ny6), polyvinyl fluoride (PVF), polyvinylidene chloride (PVdC), polyacetonitrile (PAN), ethylene vinyl alcohol (EVOH), and polyvinyl alcohol (PVA). In certain embodiments, the oxygen transmission coefficient of said polymer is less than $10^{-10}$ [$cm^3$(STP)/cm/($cm^2$+s+Pa)]. In particular embodiments, the walls of the container comprise multiple layers of one or more oxygen impermeable polymers.

In additional embodiments, the container comprises one or more resealable or closable ports of entry. In certain embodiments, the container comprises two or more resealable or closable ports of entry. As noted, in specific embodiments, the container is a bottle, a bag, a tube, a vial, or a syringe. In certain embodiments, the container is an intravenous bag or a syringe. In particular embodiments, the container is a sealable tube comprising a rubber septum, e.g., a Hungate tube.

In related embodiments, the device further comprises a delivery means coupled to the container through a resealable or closable port of entry. In particular embodiments, the delivery means is configured to intravenously deliver a solution from the container to a subject in need thereof. For example, the delivery means may be a needle or a cannula. In certain embodiments, the delivery means comprises a reduced oxygen or oxygen-free environment or is present under a reduced oxygen or oxygen-free environment.

In particular embodiments of storage or delivery devices of the present invention, the compound is a halogen compound or a chalcogenide. In certain embodiments, the compound is a reduced form of a halogen compound or a chalcogenide, e.g., an iodide, a bromide, NaI, KI, HI, CaI, AGI, $H_2Se$, $Na_2Se$, NaHSe, or HSe— anion or others described herein. In certain embodiments, the device comprises a composition of the present invention.

To prevent exposure to air in the gas-tight storage container, an inert or noble gas, such as nitrogen or argon, may be introduced into a container containing a composition of the present invention prior to closure.

In other related embodiments, compositions are stored in a light-resistant or a light-protective container or vial, such as an amber vial. The composition may be packaged in a glass vial. It may be filled to a slight over-pressure in an inert atmosphere, e.g., nitrogen, to prevent/slow oxidative breakdown of the composition, and may be contained in a form such that ingress of light is prevented, thereby preventing photochemical degradation of the composition. This may be achieved using an amber vial. Additional container systems that permit a solution to be stored in an oxygen-free environment are known, as many intravenous solutions are sensitive to oxygen. For example, a glass container that is purged of oxygen during the filling and sealing process may be used. In another embodiment, flexible plastic containers are available that may be enclosed in an overwrap to seal against oxygen. Basically, any container that prevents oxygen from interacting with the stable composition may be used (see, e.g., U.S. Pat. No. 6,458,758). In one embodiment, the container includes one or more oxygen scavenger. For example, the oxygen scavenging composition can be applied as a coating or lining upon the inside surface of the product supporting or retaining means to function as a barrier to oxygen permeation (see, e.g., U.S. Pat. No. 5,492,742).

In particular embodiments, a container or vial may comprise a unit dosage of a composition of the present invention. In certain embodiments, the unit dosage form comprises or consists of an effective amount of the composition to treat or prevent a disease, condition, or injury, including any of those described herein, in a subject.

In particular embodiments, the present invention includes a container, such as a saline bag, that includes a premixed liquid composition of a halogen compound, e.g., an iodide or bromide, wherein the amount of premixed liquid composition constitutes a dosage useful in treating or preventing a disease, condition, or injury, including any of those described herein, in a subject in need thereof, and one or more pharmaceutically acceptable carriers, diluents, or excipient. In particular embodiments, the liquid composition is sterile.

In particular embodiments, the present invention includes a container, such as a vial, that includes a dry composition of a halogen compound, e.g., an iodide or bromide, wherein the amount of dry composition constitutes a dosage useful in treating or preventing a disease, condition, or injury, including any of those described herein, in a subject in need thereof. The dry composition may be reconstituted, e.g., with a pharmaceutically acceptable carrier, diluent, or excipient, e.g., sterile water, prior to delivery to a subject in need thereof.

In certain embodiments, compositions comprising a halogen compound and an active agent used for the treatment of chronic heart failure may be prepared by admixing a reduced form of a halogen compound, e.g., iodide, and the active agent used for the treatment of chronic heart failure. In certain embodiments, one or more pharmaceutically acceptable excipients, diluents or carriers are also admixed.

Methods of Using Halogen Compounds and Other Compositions

In certain embodiments, a composition of the present invention is used to treat or prevent an injury or a disease in a biological material, e.g., a subject, e.g., a mammal, such as a human. In particular embodiments, a composition of the present invention is used to treat a subject (or biological material) prior to, during, or after exposure to an ischemic or hypoxic condition, or reperfusion. Biological material may be treated in vivo, ex vivo, or in vitro. In specific embodiments, a composition of the invention is used to treat or prevent injury caused by a heart attack or infarct resulting from a heart attack or stroke. In specific embodiments, a composition of the invention is used to treat or prevent injury caused by a cell, tissue, or organ transplant. A variety of diseases, injuries, and conditions are described herein, all of which may be treated by a composition of the present invention, e.g., a composition comprising a halogen compound such as iodide, or a composition comprising a chalcogenide such as sulfide or selenide. In particular embodiments, the composition is a stable formulation formulated to maintain the halogen compound or chalcogenide in its reduced state.

In certain embodiments, the present invention includes methods of treating or preventing a disease or injury in a biological material in need thereof, comprising providing to the biological material an effective amount of a composition of the present invention. In particular embodiments, the composition comprises an effective amount of one or more halides and/or one or more chalcogenides, and optionally one or more additional active agents, including any of those described herein. In particular embodiments, the halide or halogen compound comprises iodine, e.g., iodide or iodate. In particular embodiments, the chalcogenide comprises sulfur or selenium, e.g., sulfide or selenide. In particular embodiments, the composition also comprises glutathione or another reducing agent.

In one embodiment, compositions of the present invention are used to treat subjects who have undergone, are undergoing, or who are susceptible to a disease, injury, trauma or critical care treatment. Thus, the present invention includes a method of treating or preventing a disease, injury, or trauma, including an injury related to critical care treatment, in a subject in need thereof, comprising providing to the subject an effective amount of a composition of the present invention. In particular embodiments, the composition comprises an effective amount of one or more halides and/or one or more chalcogenides, and optionally one or more additional active agents, including any of those described herein. In particular embodiments, the injury may be caused by external insults, such as burns, wounds, amputations, gunshot wounds, or surgical trauma, abdominal surgery, prostate surgery; internal insults, such as septic shock, stroke or cardiac arrest, heart attack, chronic heart failure, e.g., that result in the acute reduction in circulation; or reductions in circulation due to non-invasive stress, such as exposure to cold or radiation. On a cellular level, injury often results in exposure of cells, tissues and/or organs to hypoxia, thereby resulting in induction of programmed cell death, or "apoptosis." In particular embodiments, injury results from reperfusion of oxygen into cells, a tissue, an organ, or a mammal following a hypoxic or ischemic event. In particular embodiments, compositions and methods of the present invention, including those related to either or both halide and/or chalcogenides, are used to treat or prevent surgical adhesion, e.g., abdominal, pelvic, and heart surgical adhesions. In certain embodiments, an adhesion is a band of scar tissue that binds two parts of tissue or organs together. The adhesion may develop when the body's repair mechanisms respond to tissue disturbance, e.g., surgery, infection, trauma or radiation. Although adhesions can occur anywhere, common locations are within the abdomen, pelvis and heart. In certain embodiments, compositions and methods of the present invention, including those related to either or both halide and/or chalcogenides, are used to treat or prevent injury associated with stem cell engraftment, and/or to promote stem cell engraftment or reduce stem cell rejection, e.g., of allogeneic or autologous stem cells introduced to a subject.

In one embodiment, the present invention contemplates contacting cells, tissues, organs, limbs, and even whole organisms, with an effective amount of a composition of the present invention as a way of protecting them from a detrimental effect of injury or disease. The present invention also contemplates methods for inducing tissue regeneration and wound healing by inhibition/prevention/delay of biological processes that may result in delayed wound healing and tissue regeneration. In certain embodiments, the present invention includes methods of protecting a biological material, or preventing or inhibiting injury to a biological material in need thereof, comprising providing to the biological material an effective amount of a composition of the present invention. In particular embodiments, the composition comprises an effective amount of one or more halides and/or one or more chalcogenides, and optionally one or more additional active agents, including any of those described herein. In this context, in scenarios in which there is a substantial wound to the limb or organism, contacting the biological matter with a composition of the present invention aids in the wound healing and tissue regeneration process by managing the biological processes that inhibit healing and regeneration. In addition to wound healing, methods of the invention can be implemented to prevent or treat trauma such as cardiac arrest or stroke, or hemorrhagic shock. The invention has importance, e.g., with respect to the risk of trauma from emergency surgical procedures, such as thoroacotomy, laparotomy, and splenic transaction or cardiac surgery, aneurysm, surgery, brain surgery and the like.

In certain embodiments, methods of the present invention can be implemented to enhance survivability or inhibit/prevent ischemic injury or inhibit/prevent reperfusion injury, e.g., resulting from cardiac arrest or stroke. Accordingly, in one embodiment, the present invention includes methods of enhancing survivability or reducing ischemic or reperfusion injury by providing to a biological material diagnosed with or at risk of ischemic injury or inhibit/prevent reperfusion injury, e.g., resulting from cardiac arrest or stroke, with a composition of the invention, e.g., a composition comprising a halogen compound, optionally in combination with one or more additional active agents, such as a chalcogenide. This may be, e.g., in a subject suffering from or at risk of cardiac arrest or stroke, comprising providing an effective amount of a composition of the invention to the subject before, after, or both before and after myocardial infarction, cardiac arrest or stroke.

"Ischemia" refers to a restriction in blood supply to tissues, causing a shortage of oxygen and glucose needed for cellular metabolism. It can be caused by problems with blood vessels, leading to damage to the affected tissue. In certain embodiments, it results from vasoconstriction, thrombosis, myocardial infarct, stroke, or embolism. As used herein, "reperfusion injury" refers to tissue damage resulting from blood returning to tissue after a period of ischemia or lack of oxygen. It is believed that the absence of oxygen and nutrients from blood during the ischemic period creates a condition in which the restoration of circulation results in inflammation and oxidative damage through the induction of oxidative stress. In certain embodiments, the method results in a reduced infarct size as compared to the size in the absence of treatment with the stable composition.

In certain embodiments, methods of the present invention include pre-treating a biological material, e.g., a subject, with a composition of the present invention prior to an ischemic, hypoxic, or reperfusion injury or event or disease insult. These methods can be used when an injury or disease with the potential to cause ischemia or hypoxia is scheduled or elected in advance, or predicted in advance to likely occur. Examples include, but are not limited to, major surgery where blood loss may occur spontaneously or as a result of a procedure, cardiopulmonary bypass in which oxygenation of the blood may be compromised or in which vascular delivery of blood may be reduced (as in the setting of coronary artery bypass graft (CABG) surgery), or in the treatment of cell, tissue or organ donors (or donor cells, tissues, or organs) prior to removal of donor cells, tissues, or organs for transport and transplantation into a recipient in need of a cell, tissue, or organ transplant. In various embodiments, the donor cell, tissue, or organ is autologous or heterologous to the graft or transplant recipient. Examples include, but are not limited to, medical conditions in which a risk of injury or disease progression is inherent (e.g., in the context of unstable angina, following angioplasty, bleeding aneurysms, hemorrhagic strokes, following major trauma or blood loss), or in which the risk can be diagnosed using a medical diagnostic test.

In certain embodiments, compounds, compositions and methods of the present invention are used to treat, inhibit, reduce or prevent any of the following diseases or conditions, or an injury related to or resulting from any of the following treatments: transplantation (e.g., kidney transplant, cadaveric kidney transplant, liver transplant, bowel transplant, lung transplant, or flap transplant); ileus (e.g., failure of peristalsis and post-operative ileus); graft vs. host disease; radiation-induced lung injury; ventilator induced lung injury; cataract (e.g., incipient cataract, senile cataract, or incipient senile cataract); Hanta pulmonary virus (HPV); Ebola virus; *Salmonella* infection, bacterial infection; ischemic birth (e.g., Hypoxic Ischemic Encephalopathy (HIE) or birth asphyxia); peripheral vascular disease; permanent ischemia; ST segment elevation myocardial infarction (STEMI); hearing loss (e.g., loud noise hearing loss or acute hearing loss); status epilepticus (epilepsy), superior mesenteric artery ischemia/reperfusion injury (e.g., ischemia-reperfusion injury following superior mesenteric artery occlusion); sickle cell anemia or sickle cell crisis; or contrast-induced nephropathy. In certain embodiments, any of these diseases, disorder or injuries are treated with a composition comprising a chalcogenide, or a composition comprising a halide. In particular embodiments, the composition comprising a chalcogenide comprises sulfide or selenide, e.g., in a reduced form, including any of the compositions described herein, such s those that maintain the sulfide or selenide in a reduced form.

In certain embodiments, the invention comprises treating or preventing radiocontrast agent induced kidney injury in a subject in need, comprising providing to the subject an effective amount of a composition comprising a halogen (e.g., iodide) or a chalcogenide (e.g., sulfide or selenide). Radiocontrast agent induced kidney injury (contrast-induced nephropathy) represents a significant clinical problem and has been associated with increased patient mortality and longer hospitalizations. Radiocontrast agent administration, conducted in conjunction with imaging of the coronary arteries, the peripheral arteries or the kidneys is a common medical intervention. However, radiocontrast agent administration often leads to significant kidney damage in a subset of patients with certain risk factors. For example, patients who are elderly, have an underlying disease (e.g., diabetes or atherosclerosis) and/or have a borderline impairment in their renal function are especially predisposed to kidney injury. In one embodiment, the radiocontrast agent is administered before or during kidney diagnostic imaging. In another exemplary embodiment, the radiocontrast agent is administered before or during heart blood vessel diagnostic imaging. In another exemplary embodiment of the method, the radiocontrast agent is an iodinated radiocontrast agent. In another exemplary embodiment of the method, the subject (e.g., human patient in need of treatment thereof) has a pre-existing impairment of renal function prior to administration of the radiocontrast agent. In another exemplary embodiment of the method, the human has a baseline creatinine level greater than or equal to 120 µmol/L, a glomerular filtration rate of less than 60 mL/min per 1.73 $m^2$ and/or a creatinine clearance of less than 60 mL/min. In another exemplary embodiment of the method, the human has one of more conditions selected from type 1 or 2 diabetes mellitus, atherosclerosis, congestive heart failure, an intraarterial balloon pump, anemia, a systolic blood pressure of less than 80 mm Hg, an age greater than 50 years, a glomerular filtration rate of less than 60 mL/min per 1.73 $m^2$ and reduced intravascular volume. In another exemplary embodiment of the method, the radiocontrast agent induced kidney injury is radiocontrast agent induced nephropathy or acute renal dysfunction.

Thus, in certain embodiments, the present invention includes a method of treating, preventing, reducing, inhibiting (or reducing or inhibiting an injury associated with) any of the disorders or procedures described herein in a biological material (e.g., a subject), comprising providing an effective amount of a compound or composition described herein to the biological material (e.g., the subject).

In certain embodiments, the present invention includes a method of treating, preventing, reducing, inhibiting chronic heart failure in a subject in need thereof, comprising providing an effective amount of a compound or composition described herein to the subject (e.g., the subject). In particular embodiments, the subject has been diagnosed as having or being susceptible to chronic heart failure, e.g., systolic heart failure. CHF may be diagnosed based on the history of the symptoms and a physical examination with confirmation by echocardiography. In addition, blood tests, electrocardiography, and chest radiography may be useful to determine the underlying cause. In particular embodiments, the subject has been diagnosed with chronic heart failure due to left ventricular dysfunction or systolic heart failure. In particular embodiments, the subject has undergone a heart attack, e.g., within the one day, one week, one month, 6 months, one year, or 5 years prior to the commencement of the treatment. In certain embodiments, the subject is provided with a halogen, such as an iodine-containing halogen, e.g., iodide. In particular embodiments, the subject is provided with a pharmaceutical composition comprising a reduced form of a halogen compound, e.g., a reduced form of iodine, such as iodide or iodiate, and a pharmaceutically acceptable carrier, diluent, or excipient. In certain embodiments, the pharmaceutical composition further comprises glutathione. In certain embodiments, the glutathione is present in an amount sufficient to maintain the halogen or halogen compound in its reduced state. In particular embodiments, the subject is provided with any of the compositions, e.g., pharmaceutical compositions, or unit dosage forms described herein via any of the routes of administration described herein. In particular embodiments, the subject is provided with the halogen compound orally or intravenously.

In particular embodiments of methods of treating or preventing CHF, e.g., systolic heart failure, a halogen compound is provided to the subject in combination with one or more other active agents used to treat CHF. In certain embodiments, the subject is provided an effective amount of a first pharmaceutical composition comprising a reduced form of a halogen compound, e.g., a reduced form of iodine, such as an iodide or iodiate, and a pharmaceutically acceptable carrier, diluent, or excipient, and an effective amount of a second pharmaceutical composition comprising another active agent used to treat CHF. It is understood that the effective amount of each pharmaceutical composition when used in combination may be less than the effective amount of one or both compositions when they are used alone. In certain embodiments, the two pharmaceutical compositions act synergistically to treat or prevent CHF.

In certain embodiments, the another active agent used to treat CHF, e.g., CHF due to left ventricular dysfunction, is an angiotensin converting enzyme (ACE) inhibitors or a beta blocker. In other embodiments, the another active agent is an aldosterone antagonist, an angiotension receptor blocker, or hydralazine with a nitrate. In additional embodiments, the another active agent is an anticoagulant, an antiplatelet therapy, an angiotensin II receptor blocker, a calcium channel blocker, a diuretic, a vasodilator, or a statin. In particular embodiments, a biological material, e.g., a mammalian cell, tissue, organ or a mammal, is pre-treated with a composition of the invention, e.g., a composition comprising a halogen compound, prior to an ischemic, hypoxic or reperfusion event or injury. In particular embodiments, the biological material is contacted with the composition for at least or about one hour, at least or about two hours, at least or about four hours, at least or about six hours, at least or about eight hours, at least or about ten hours, at least or about 12 hours, at least or about 16 hours, at least or about 20 hours, at least or about 24 hours, at least or about 36 hours, at least or about 48 hours, at least or about three days, at least or about four days, at least or about five days, at least or about one week, at least or about two weeks, at least or about one month, between one hour and one week, between one hour and 48 hours, between one hour and 24 hours, between two hours and one week, between two hours and 48 hours, between two hours and 24 hours, between four hours and one week, between four hours and 48 hours, between four hours and 24 hours, between twelve hours and one week, between twelve hours and 48 hours, between twelve hours and 24 hours, between 24 hours and one week, or between 24 hours and 48 hours prior to or immediately prior to the ischemic, hypoxic or reperfusion event or injury. In certain embodiments, there is a period of time after treatment and immediately prior to the ischemic, hypoxic or reperfusion event or injury during which the biological matter is not contacted with the composition of the present invention, e.g., a period of time of about five minutes, about ten minutes, about 20 minutes, about 30 minutes, about one hour, about two hours, about four hours, about eight hours, about 12 hours, or about 24 hours. In particular embodiments, the biological material, e.g., cell, tissue or organ, is grafted or transplanted to a recipient, either while being treated or after being treated with a composition of the present invention. In particular embodiments, the grafter or transplanted biological material is autologous or heterogonous to the recipient.

Relatedly, additional embodiments of the invention concern enhancing survivability and preventing irreversible tissue damage from blood loss or other lack of oxygenation to cells or tissue, such as from lack of an adequate blood supply. In certain embodiments, the present invention includes methods of enhancing survivability or preventing tissue damage from blood loss or other lack of oxygenation to cells or tissue in a biological material in need thereof, comprising providing to the biological material an effective amount of a composition of the present invention. In particular embodiments, the composition comprises an effective amount of one or more halides and/or one or more chalcogenides, and optionally one or more additional active agents, including any of those described herein. Lack of adequate blood supply may be the result of, for example, actual blood loss, or it may be from conditions or diseases that cause blockage of blood flow to cells or tissue, that reduce blood pressure locally or overall in an organism, that reduce the amount of oxygen that is carried in the blood, or that reduces the number of oxygen carrying cells in the blood. Conditions and diseases that may be involved include, but are not limited to, blood clots and embolisms, cysts, growths, tumors, anemia (including sickle cell anemia), hemophilia, other blood clotting diseases (e.g., von Willebrand, or ITP), and atherosclerosis. Such conditions and diseases also include those that create essentially hypoxic or anoxic conditions for cells or tissue in an organism because of an injury, disease, or condition.

In one embodiment, the present invention provides methods and compositions to enhance the survivability of or reduce or prevent injury or damage to biological material (e.g., a mammal or tissue or organ within a mammal) undergoing hemorrhagic shock or undergoing reperfusion, which include contacting the biological material at risk of or in a state of hemorrhagic shock with an effective amount of a composition of the present invention as soon as practical, e.g., within one hour of the injury. This method allows for the subject to be transported to a controlled environment (e.g., surgery), where the initial cause of the injury can be addressed, and then the patient can be brought back to normal function in a controlled manner. For this indication, the first hour after injury, referred to as the "golden hour," is crucial to a successful outcome.

In various other embodiments, the methods and compositions of the present invention may be used in the treatment or prevention of neurodegenerative diseases associated with ischemia, hypoxia or reperfusion, in the treatment of hypothermia, in the treatment of hyperproliferative disorders, and in the treatment of immune disorders. In various other embodiments, the biological condition is any one or combination of the following: neurological disease, cardiovascular disease, metabolic disease, infectious disease, lung disease, genetic disease, autoimmune disease, and immune-related disease. In certain embodiments, the methods and compositions of the present invention are used to enhance the survivability of ex vivo biological matter subjected to hypoxic or ischemic conditions, including, e.g., isolated cells, tissues and organs. Specific examples of such ex vivo biological material include platelets and other blood products, as well as cells, tissues and organs to be transplanted, e.g., for autologous or heterologous transplantation. In various embodiments, biological material for transplantation is treated with a composition described herein while still in the donor, after removal from the donor, or after transplantation into the recipient, or any combination thereof. In particular embodiments transplant recipient is treated with a composition described herein before, during or after transplantation of a biological material, e.g., cells, tissue or organ.

Methods of the present invention may be used to regulate the reducing environment of blood, a tissue, or cells, including, e.g., those present at the site of injury or disease, such as, e.g., a myocardial infarct. In certain embodiments, the present invention includes methods of regulating the reducing environment in a biological material, comprising providing to the biological material an effective amount of a composition of the present invention. In particular embodiments, the composition comprises an effective amount of one or more halides and/or one or more chalcogenides, and optionally one or more additional active agents, including any of those described herein. Without wishing to be bound to any particular theory, it is understood that under normal conditions, there exists in the red cells a constant ratio of reduced to oxidized glutathione of about 99:1. Under these conditions, anions such as selenite and iodate enter red cells via the anion transporter/band 3 protein on the plasma membrane, and upon being exposed to the highly reduced glutathione become transformed/reduced to selenide and iodide. An additional by product of this reaction is the production of a small amount of oxidized glutathione. This oxidized glutathione is re-reduced using energy generated from the oxidation of glucose via the pentose phosphate pathway. The selenide and iodide leave via the anion transporter/band 3 protein and have the effect of moving the reducing power of the red cell to other parts of the body. When this pathway becomes overwhelmed, such as, e.g., during injury or disease, the ratio of reduced to oxidized glutathione falls, e.g., below 90:10, below 80:10, below 70:10 below 60:10 or as low as 50:50 following a heart attack. In addition, it is thought that the amount of reduced anions, such as selenide and iodide, that are produced by the red blood cells and released into the bloodstream and tissues is also reduced, resulting in a lower amount of reducing agents in the bloodstream and tissues, including, e.g., injured or diseased tissues. The lower amount of reducing agents (iodide and selenide) results in a diminish capacity to neutralize free radicals, which result in oxidative stress and causes tissue damage, e.g., damage resulting from hypoxia, ischemia, or reperfusion. This phenomenon is referred to as a "blood attack." This and related mechanisms are discussed in, e.g., D'Alessandro, A. et al. Blood Transf, 2013: 11: 75-87; Salmi, H. et al., Pediatric Endocrinology, Diabetes, and Metabolism 2011, 17, 1, 14-19; Snethil, S. et al., Clinica Chimica Acta 348 (2004) 131-137; and Tolan, N. et al., Anal. Chem. 2009, 81, 31202-3108. Furthermore, addition of exogenous iodide and selenide into the blood stream relieves the burden on the red cells to produce selenide and iodide and enables the red cells to use the reminding reducing power for the maintenance of hemoglobin.

Glutathione (GSH) is a tripeptide with a gamma peptide linkage between the amine group of cysteine (which is attached by normal peptide linkage to a glycine) and the carboxyl group of the glutamate side-chain. It is an antioxidant, preventing damage to important cellular components caused by reactive oxygen species such as free radicals and peroxides. Thiol groups are reducing agents, existing at a concentration of approximately 5 mM in animal cells. Glutathione reduces disulfide bonds formed within cytoplasmic proteins to cysteines by serving as an electron donor. In the process, glutathione is converted to its oxidized form glutathione disulfide (GSSG), also called L-(−)-glutathione. Oxidized glutathione can be reduced by glutathione reductase, using NADPH as an electron donor. The ratio of reduced glutathione to oxidized glutathione within cells is often used as a measure of cellular toxicity.

Accordingly, the present invention provides a method of treating or preventing an injury or disease, including any of those described herein, including but not limited to ischemic or reperfusion injury, in a subject in need thereof, by inhibiting or preventing a decrease in the ratio of the amount or molar concentration of reduced forms of glutathione to the amount or molar concentration of oxidized forms of glutathione in the subject's bloodstream or at a site of disease or injury, e.g., in a diseased or injured tissue. In certain embodiments, the method comprises providing to the subject an effective amount of a composition of the present invention. In particular embodiments, the composition comprises an effective amount of one or more halides and/or one or more chalcogenides, and optionally one or more additional active agents, including any of those described herein. The method may also be used to increase the ratio of the amount or molar concentration of reduced forms of glutathione to the amount or molar concentration of oxidized forms of glutathione in the subject's bloodstream or at the site of disease or injury. In particular embodiments, the methods comprise providing a halogen compound and/or a chalcogenide systemically to the subject prior to, at the time of, or after onset of said disease or injury. In certain embodiments, a halogen compound, e.g., iodide, and is provided to the subject prior to the onset of the disease or injury. In particular embodiments, a chalcogenide, e.g., selenide, is provided to the subject prior to the onset of the disease or injury, during the onset or occurrence of the disease or injury, of after the onset of the disease or injury. It is further understood that other compounds that impede thyroid hormone production, activity or function, including goitrogens, may be used instead of or in combination with the halogen compound or chalcogenide to practice these or other methods of the invention. Chalcogenides and halogen compounds may be used at any of the various amounts described herein. In certain embodiments, about 1 pg/kg to about 1 g/kg of chalcogenide, sulfide, or selenide is provided to the subject, about 10 μg/kg to about 10 mg/kg of chalcogenide, sulfide or selenide is provided to the subject. In certain embodiments, the halogen compound is iodide and about 10 pg/kg to about 1 g/kg of iodide is provided to the subject. In certain embodiments, about 10 μg/kg to about 10 mg/kg of iodide is provided to the subject.

In certain embodiments, the methods of the invention inhibit or maintain the ratio of the amount or molar concentration of reduced forms of glutathione to the amount or molar concentration of oxidized forms of glutathione in the subject's bloodstream or at the site of disease or injury from falling below 99%, below 98%, below 97%, below 96%, below 95%, below 94%, below 93%, below 92%, below 91%, below 90%, below 80%, below 70%, below 60%, below 50%, below 40%, below 30%, below 20%, or below 10% after onset of the disease or injury. In certain embodiments, the methods of the invention increase the ratio of the amount of reduced forms of glutathione to the amount of oxidized forms of glutathione in the subject's bloodstream or at the site of disease or injury to at or above 99%, at or above 98%, at or above 97%, at or above 96%, at or above 95%, at or above 94%, at or above 93%, at or above 92%, at or above 91%, at or above 90%, at or above 80%, at or above 70%, at or above 60%, at or above 50%, at or above 40%, at or above 30%, at or above 20%, or at or above 10% after onset of the disease or injury. In particular embodiments, the recited ratios are achieved within or maintained for 1 minute, 5 minutes, 30 minutes, one hour, 2 hours, four hours, eight hours, 12 hours, 24 hours, 48 hours, or 48 hours of the time when the composition is provided to the subject.

The present invention further provides methods of determining or monitoring the therapeutic effect of a composition or treatment, including any of the compositions or methods described herein, which may be practiced alone or in combination with any of the methods described herein. These methods comprise determining the ratio of the amount or concentration of reduced glutathione to the amount or molar concentration of oxidized glutathione. The ratio of the amount or molar concentration of reduced glutathione to the amount or molar concentration of oxidized glutathione may be determined, e.g., for a blood sample, e.g., as described in any of the previously cited articles. An increase or inhibition of further reduction in the ratio following treatment is indicative of efficacy, whereas a decrease in the ratio suggests that the treatment has limited or no therapeutic value.

In some embodiments, the present invention relates to a method of preventing, inhibiting, or reducing an immune response in a biological material or subject in need thereof, comprising providing to the biological material or subject an effective amount of a composition of the present invention. In particular embodiments, the composition comprises an effective amount of one or more halides and/or one or more chalcogenides, and optionally one or more additional active agents, including any of those described herein. In some embodiments, an immune response generally refers to any response elicited by the innate or adaptive immune system. In some embodiments, the immune response is initiated by the activation of a T cell. In some embodiments, the immune response is initiated by the activation of a B cell. Immune responses contemplated herein may be stimulated any means. In some embodiments, an immune response is induced by a pathogen. In some embodiments, an immune response is an autoimmune response. In some embodiments, immune response refers to inflammation. In certain embodiments, an autoimmune response is induced following transplantation of cells, tissue or an organ. In certain embodiments, an autoimmune response is the result of an autoimmune disorder.

In some embodiments, inflammation refers to a nonspecific first reaction mounted by the immune system in response to a perceived injury or threat. It is an innate defensive response, distinguished from the more precisely tailored adaptive responses of the immune system. Inflammation may work cooperatively with adaptive responses of the immune system, which develop more slowly but are more precisely targeted to a harmful agent such as a chemical or pathogen that may be causing localized injury.

Inflammation may be associated with infections, but it occurs in response to virtually any type of injury or threat, including physical trauma, cold, burns from radiation, heat or corrosive materials, chemical irritants, bacterial or viral pathogens, localized oxygen deprivation (ischemia) or reperfusion (sudden reinfusion of oxygen to ischemic tissue), and others. It includes the classic symptoms of redness, heat, swelling, and pain, and may be accompanied by decreased function of the inflamed organ or tissue. It may be a generalized reaction involving several effects that may tend to combat an injurious agent that may be present at the site where an injury or threat was detected, or it may tend to contain the injury or threat to its initial location, to keep it from spreading rapidly.

In some embodiments, an autoimmune response is generally defined as any response in an organism that results in a immune attack against its own cells and tissues. The etiology of autoimmunity is very broad, comprising genetic and environmental factors as well as immunological mechanisms including, e.g, but not to be limited in anyway: T-Cell Bypass; T-Cell-B-Cell discordance; Aberrant B cell receptor-mediated feedback; Molecular Mimicry; Idiotype Cross-Reaction; Cytokine Dysregulation; Dendritic cell apoptosis; Epitope spreading, epitope drift; Epitope modification or Cryptic epitope exposure.

In some embodiments, autoimmunity refers to systemic autoimmune diseases, which are defined as autoimmune diseases that damage many organs; such as e.g., lupus erythematosus, Sjögren's syndrome, scleroderma, rheumatoid arthritis, and autoimmune myositis such as dermatomyositis, polymyositis, vasculitis (e.g., Churg-Strauss Syndrome), Sarcoidosis, general allergies etc.

In some embodiments, autoimmunity refers to local autoimmune syndromes, which are defined as autoimmune disease that affect a single organ or tissue; such as e.g., diabetes mellitus type 1; Hashimoto's thyroiditis; Addison's disease; Celiac disease; Crohn's Disease; Graves' disease, Pernicious anaemia; Psoriasis; Pemphigus vulgaris; Vitiligo; Autoimmune haemolytic anaemia; Idiopathic thrombocytopenic purpura; Myasthenia gravis; etc.

Some embodiments of the present invention relate to the treatment, prevention, or amelioration of organ rejection or graft-versus-host disease (GVHD) and/or conditions associated therewith. In certain embodiments, the present invention includes methods of treating or preventing organ rejection or graft-versus-host disease (GVHD) and/or conditions associated therewith in a subject in need thereof, comprising providing to the subject an effective amount of a composition of the present invention. In certain embodiments, the present invention includes methods of treating or preventing organ rejection or graft-versus-host disease (GVHD) and/or conditions associated therewith in a subject in need thereof, comprising providing contacting the transplanted cells, tissue or organ with an effective amount of a composition of the present invention. In particular embodiments, the composition comprises an effective amount of one or more halides and/or one or more chalcogenides, and optionally one or more additional active agents, including any of those described herein. Organ rejection occurs by host immune cell destruction of the transplanted tissue through an immune response. Similarly, an immune response is also involved in GVHD, but, in this case, the foreign transplanted immune cells destroy the host tissues. The administration of the halogen or chalcogenide compounds of the invention, that inhibit an immune response, may be an effective therapy in preventing organ rejection or GVHD.

Some embodiments relate to the treatment, prevention, or amelioration of inflammation resulting from an ischemic or reperfusion injury. In certain embodiments, the present invention includes methods of treating or preventing inflammation, e.g., inflammation resulting from an ischemic or reperfusion injury in a subject in need thereof, comprising providing to the subject an effective amount of a composition of the present invention. In certain embodiment, the composition comprises an effective amount of a halide and/or an effective amount of a chalcogenide, and optionally one or more additional active agents, including any of those described herein. In certain embodiments, reperfusion injuries occur when blood supply to an organ has been cut off for a period of time, such as e.g. following myocardial infarction, stroke, and other thrombotic events. During ischemia, tissues become stressed due to lack of oxygen, and eventually, if the ischemia is prolonged, the tissue will become necrotic, resulting in the accumulation of various metabolic intermediates. Restoration of blood flow results in a rapid increase in oxygen radical that lead to inflammation. Thus embodiments of the present invention relate to the use of halogen compounds such as iodide, or chalcogenide compounds such as selenide or sulfide to reduce the formation of the reactive oxygen species.

There are many different assays described in the art that are useful for detecting the activation of an immunological response. Some typical non-limiting examples of these include, but are in know way limited to: methods to detect lymphocytes (i.e., T cells, B cells, and NK cells), monocytes, and dendritic cells. Examples of such assays include e.g., ELISPOT; flow cytometry-based analysis of cytokine expression; HLA-peptide multimer staining; MHC Tetramer analysis; carboxyfluorescein succinimidyl ester assay; antigen-specific immune responses: delayed-type hypersensitivity, PCR-based detection of T-cell receptor gene usage or cytokine production, mixed lymphocyte reactions to measure T cell proliferation, etc.

In embodiments, any assay capable of detecting an immune response generated by any stimulus, is useful for measuring the effect that a halogen compound or a chalcogenide compound may have on the suppression of an immune response.

In particular embodiments, immunosuppression induced by halogen or chalcogenide compounds is assessed by measuring T cell proliferation, e.g., in response to activated antigen presenting cells. Essentially a mixed lymphocyte reaction, this assay exploits that fact that T cell exposure to presented antigens result in T cell activation and proliferation, as well as supportive increases in DNA synthesis. PBMCs were isolated from two donors and then the samples were split into two groups, one that receives irradiation and one that does not. Irradiation results in the presentation of numerous antigens to antigen presenting cells, thus the irradiated cells serve as potent activators of T cells. By mixing the irradiated cells with the non-irradiated cells, strong T cell proliferation will occur. This proliferation can be measured using any proliferation assay, as would be commonly known to the skilled artisan. In one embodiment, proliferation is assessed by measuring DNA synthesis. Mixed PBMC were cultured in the presence or absence of halogen or chalcogenide compounds for 5 days, and then pulsed with tritiated thymidine for 18 hours to label newly synthesized DNA. The degree of labeling is directly correlated with the degree of T cell activation, thus low levels of labeling correlate with immunosuppression.

In some embodiments, halogen or chalcogenide compound immunosuppression is assessed using this assay, and the halogen compound is found to result in a 10% reduction in tritiated thymidine incorporation, thus indicating 10% immunosuppression. In some embodiments, treatment with a halogen compound in this way results in 20% immunosuppression, or 30%, 40%, 50%, 60%, 70%, 80%, 90%, or 100% immunosuppression. In particular embodiments, the halogen compound comprises iodide. In particular embodiments the chalcogenide compound that induces immunosuppression comprises selenide or sulfide.

In certain embodiments of methods of the invention, the amount of or effective amount of a halogen compound that is provided to a biological material, e.g., a mammal or tissue therein, is about, at least, at least about, or at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mg, mg/kg, or mg/m$^2$, or any range derivable therein. Alternatively, the amount may be expressed as 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mM or M, or any range derivable therein.

In certain embodiments of methods of the invention, the halogen compound comprises iodine or iodide, e.g., NaI, and the effective amount is greater than or equal to about 150 µg, greater than or equal to about 300 µg, greater than or equal to about 500 µg, greater than or equal to about 1 mg, greater than or equal to about 2 mg, greater than or equal to about 5 mg, greater than or equal to about 10 mg, greater than or equal to about 15 mg, or greater than or equal to about 20 mg. In certain embodiments, the effective amount is 150 µg to 1000 mg, 300 µg to 1000 mg, 500 µg to 1000 mg, 1 mg to 1000 mg, 2 mg to 1000 mg, 5 mg to 1000 mg, 10 mg to 1000 mg, 150 µg to 100 mg, 300 µg to 100 mg, 500 µg to 100 mg, 1 mg to 100 mg, 2 mg to 100 mg, 5 mg to 100 mg, or 10 mg to 100 mg. In certain embodiments, the effective amount is 150 µg to 50 mg, 300 µg to 20 mg, 500 µg to 10 mg, 1 mg to 20 mg, 1 mg to 10 mg, or about 5 mg, about 10 mg, about 15 mg, or about 20 mg.

In particular embodiments of any of the methods of the present invention, a biological material, e.g., a subject, is treated with or contacted with an effective amount of a composition or compound of the present invention, wherein said effective amount of about 0.01 mg/kg to about 20 mg/kg, about 0.05 mg/kg to about 10 mg/kg, about 0.1 mg/kg to about 5 mg/kg, about 0.5 mg/kg to about 2 mg/kg, about 0.5 mg/kg to about 1 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg or about 1.2 mg/kg.

In particular embodiments, an effective amount of iodine or iodide is an amount at least or about two-fold, three-fold, four-fold, five-fold, six-fold, seven-fold, eight-fold, nine-fold, ten-fold, twelve-fold, fifteen-fold, or twenty-fold of the average daily recommended amounts as listed below. In particular embodiments, the effective amount of iodine or iodide is an amount between two-fold and twenty-fold, between five-fold and fifteen-fold, or between five-fold and ten-fold of the average daily recommended amounts of iodine as listed below.

| Life Stage | Recommended Amount[1] (mcg) |
|---|---|
| Birth to 6 months | 110 |
| Infants 7-12 months | 130 |
| Children 1-8 years | 90 |
| Children 9-13 years | 120 |
| Teens 14-18 years | 150 |
| Adults | 150 |
| Pregnant teens and women | 220 |
| Breastfeeding teens and women | 290 |

[1]NIH Office of Dietary Supplements Iodine Fact Sheet for Consumers, reviewed Jun. 24, 2011, obtained 2013.

In particular embodiments of any of the methods of the present invention, the methods further comprising measuring or determining the amount or concentration of halogen compound present in a biological material or subject to be treated (e.g., the concentration present in a subject's bloodstream), and then providing to the biological material or subject an amount of composition comprising a halogen compound to achieve a desired total amount or concentration of halogen compound in the biological material or subject, wherein the total amount or concentration includes both the amount or concentration measured or determined in the biological material or subject and the amount provided to the biological material or subject. In particular embodiments, the desired total amount is an effective amount for the treatment or prevention of the disease or injury afflicting a subject, or an effective amount for preventing inflammation or rejection of a transplanted organ. In certain embodiments of methods of the invention, the halogen compound comprises iodine, e.g., NaI, and the effective amount is about 0.01 mg/kg to about 20 mg/kg, about 0.05 mg/kg to about 10 mg/kg, about 0.1 mg/kg to about 5 mg/kg, about 0.5 mg/kg to about 2 mg/kg, about 0.5 mg/kg to about 1 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg or about 1.2 mg/kg. In certain embodiments, the halogen compound comprises iodine, and the effective amount is an amount that achieves about the same concentration or amount that is achieved by an effective amount of iodine that is at least or about two-fold, three-fold, four-fold, five-fold, six-fold, seven-fold, eight-fold, nine-fold, ten-fold, twelve-fold, fifteen-fold, or twenty-fold of the average daily recommended amounts as listed below. In particular embodiments, the effective amount of iodine or iodide is an amount between two-fold and twenty-fold, between five-fold and fifteen-fold, or between five-fold and ten-fold of the average daily recommended amounts of iodine as listed below.

| Life Stage | Recommended Amount[1] (mcg) |
|---|---|
| Birth to 6 months | 110 |
| Infants 7-12 months | 130 |
| Children 1-8 years | 90 |
| Children 9-13 years | 120 |
| Teens 14-18 years | 150 |
| Adults | 150 |
| Pregnant teens and women | 220 |
| Breastfeeding teens and women | 290 |

[1]NIH Office of Dietary Supplements Iodine Fact Sheet for Consumers, reviewed Jun. 24, 2011, obtained 2013.

In additional embodiments wherein a composition comprising a halogen compound is provided in combination with one or more additional active agent (or composition comprising the same), the amount or effective amount of the additional active agent is any of the concentrations or dosages described herein with respect to the halogen compound. In addition, the additional active agent may be provided by any of the routes of administration described herein with respect to the composition comprising the halogen compound. In addition, the composition comprising the halogen compound and the composition comprising the additional active agent, e.g., a chalcogen such as a sulfide or selenide, may be provided to the subject at the same time, at different times, or during overlapping time periods.

In particular embodiments where the composition comprises glutathione and either or both of a halogen compound and a chalcogenide, the halogen compound and chalcogenide (when present) are administered at any of the amounts described herein for either active agent. In certain embodiments glutathione is present in an amount sufficient to inhibit oxidation of the chalcogenide and/or halogen compound, including any of the ranges described herein. In particular embodiments, the halogen compound is iodide, e.g., NaI, and the chalcogenide is sulfide or selenide.

In particular embodiments of the present invention, an effective amount of a composition is administered to a biological material, e.g., a tissue or subject, prior to reperfusion, e.g., for at least one, two three, four, five or ten minutes of the ten minutes or thirty minutes immediately prior to ischemia or reperfusion. In particular embodiments, this administration of the composition results in reduced ischemic or reperfusion injury. In certain embodiments, the reperfusion injury is less than 80%, less than 70%, less than 60%, less than 50%, less than 40%, or less than 30% the reperfusion injury in the absence of treatment with the composition.

In particular embodiments, treatment of a biological material, i.e., a subject, with a composition of the present invention following an injury, e.g., heart attack or stroke, results in a reduced injury, e.g., infarct size. In certain embodiments, the injury or infarct size is less than 80%, less than 70%, less than 60%, less than 50%, less than 40%, or less than 30% the severity or infarct size in the absence of treatment with the stable composition.

In particular embodiments, treatment of a biological matter, e.g., a subject within 10 minutes, within 30 minutes, within one hour, or within two hours or a heart attack, with a composition of the present invention results in a decrease in heart damage or an increase in fractional shortening or left ventricular function, as compared to in the absence of treatment with the composition. In particular embodiments, the decrease in heart damage is at least 10%, at least 20%, at least 30%, at least 40%, or at least 50%, as compared to in the absence of treatment with the composition. Decrease in heart damage may be detected by assessing levels of the heart specific protein, cardiac troponin I, in the blood of a subject after treatment. In particular embodiments, the increase in fractional shortening or left ventricular function is at least 20%, at least 30%, at least 40%, or at least 50%, as compared to in the absence of treatment with the composition.

In certain embodiments, the present invention includes a method of reducing inflammation in the heart of a subject, e.g., a mammal, after heart attack, by administering to the subject a composition of the present invention. In certain embodiments, the decrease in heart inflammation is at least 10%, at least 20%, at least 30%, at least 40%, or at least 50%, as compared to in the absence of treatment with the composition.

In various embodiments of methods of the present invention, a biological material, e.g., an organ, a subject, or a tissue therein, is exposed to a composition of the current invention for about, at least, at least about, or at most about 30 seconds, 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days or more, and any range or combination therein.

Furthermore, when administration of a composition according to the present invention is intravenous or by infusion, it is contemplated that the following parameters may be applied. A flow rate of about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 gtts/min or μgtts/min, or any range derivable therein. In some embodiments, the amount of the composition is specified by volume, depending on the concentration of the halogen compound present in the composition. An amount of time may be about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months, or any range derivable therein.

Volumes of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 mls or liters, or any range therein, may be administered overall or in a single session.

According to various embodiments of the methods of the present invention, a biological material is provided with a composition of the invention, e.g., intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, intraocularly, subcutaneously, subconjunctival, intravesicularly, mucosally, intrapericardially, intraumbilically, intraocularally, orally, topically, locally, by injection, by infusion, by continuous infusion, by absorption, by adsorption, by immersion, by localized perfusion, via a catheter, or via a lavage. In particular embodiments, it is provided parenterally, e.g., intravenously, or by inhalation. "Parenteral" refers to any route of administration of a substance other than via the digestive tract. In specific embodiments, a halogen compound is provided to the subject by intravenous administration or infusion.

In certain embodiments, a method or composition of the present invention is used to treat or prevent a disease or injury selected from any of the following, or which is caused by or results from any of the following: ablation therapy, adrenalectomy, aortic aneurysm, aortic root surgery, aortic stenosis, aortic valve disease, arrhythmia, atherosclerosis, atrial flutter, atrial fibrillation, atrial septal defect, arteriovenous malformation, awake brain surgery, bariatric surgery, bone marrow transplant, brachial plexus injuries, bradycardia, brain aneuryism, breast augmentation surgery, breast reduction surgery, burn injury, coronary bypass surgery, coronary artery disease, cardiac ablation, cardiac catheterization, cardiac resynchronization therapy, cardiac surgery, cardiomyopathy, cardiac surgery, cardiovascular diseases, carotid angioplasty and stenting, coarctation of the aorta, congenital heart disease, coronary bypass surgery, coronary artery disease, critical care medicine, chronic obstructive pulmonary disease, elbow replacement surgery, emergency medicine, general internal medicine, general surgery, gastrointestinal bleeding, heart attack, heart transplant, heart valve surgery, hip replacement surgery, hypertrophic cardiomyopathy, hypoxia ischemia encephalopathy, hysterectomy, ileoanal anastomosis (j pouch) surgery, inflammatory bowel disease, ischemic heart disease, ischemia reperfusion injury, irritable bowel syndrome, jaw surgery, kidney transplant, laryngotracheal reconstruction surgery, liver transplant, lung volume reduction surgery, lung transplant, minimally invasive heart surgery, neurosurgery, oral and maxillofacial surgery, orthopedic surgery, pancreas transplant, pancreatitis, partial nephrectomy, pediatric cervical spine surgery, pediatric surgery, pelvic organ prolapse, plastic and reconstructive surgery, pulmonary and critical care medicine, pulmonary atresia, pulmonary vein isolation, rectal prolapse, restrictive cardiomyopathy, retinal detachment, retinopathy of prematurity, robotic surgery, spinal cord injury, spontaneous coronary artery dissection, spontaneous occlusion of the circle of willis, stroke, stroke telemedicine (telestroke), sudden cardiac arrest, stereotactic radiosurgery, surgery, chronic heart failure, systolic heart failure, tachycardia, teare's disease, thoracic aortic aneurysm, thoracic surgery, total elbow arthroplasty, tricuspid valve disease, ulcerative colitis, valve-preserving aortic root repair, vascular and endovascular surgery, vascular medicine, or ventricular tachycardia.

In certain embodiments, the injury or disease is selected from, results from or is caused by inflammation, heart attack, coronary bypass surgery, ischemia, gut ischemia, liver ischemia, kidney ischemia, hypoxic-ischemic encephalopathy, stroke, traumatic brain injury, limb ischemia, eye ischemia, sepsis, smoke, burn, reperfusion, or acute lung injury. In certain embodiments, the injury is an infarct caused by a heart attack or a stroke. In particular embodiments, the injury is caused by coronary bypass surgery, optionally a coronary artery bypass graft (CABG). In one embodiment, the disease is hypoxic-ischemic encephalopathy.

Delivery Devices

In additional embodiments, the present invention includes a drug delivery device designed to limit, prevent or inhibit oxidation of a reduced form of an active agent, such as, e.g., a reduced form of a halogen compound or a reduced form of a chalcogenide. In specific embodiments, the device maintains a reduced form of an active agent in its reduced form. In particular embodiments, the device comprises the reduced form of an active agent, such as the reduced form of a halogen compound or chalcogenide, for example. In specific embodiments, the drug device comprises a composition of the present invention.

Manufacturer-prepared, premixed ready-to-use products represent a useful approach to intravenous drug safety, since they remove error associated with measuring and diluting intravenous or infused drugs. Accordingly, in certain embodiments, the present invention includes a drug delivery device for administration of a ready-to-use product comprising a reduced form of an active agent. In particular embodiments, the reduced form of active agent is a reduced form of a halogen compound and/or a chalcogenide, e.g., selenide or sulfide.

In related embodiments, the present invention comprises a container having therein an effective amount of a composition of the present invention or an effective amount of a halogen compound. The effective amount may be in liquid form, e.g., the active agent may be dissolved in a solution, or it may be in dry form (e.g., dried, lyophilized, or freeze-dried), such that the active agent may be dissolved in a solution prior to administration to a subject.

In all embodiments of compositions described herein, it is understood that the composition may be a pharmaceutical composition.

In addition, it is understood that traditional methods for delivering active agents, which can involve injecting air into a vial comprising the active agent during the process of withdrawing the active agent into a syringe or bag, may result in the undesired oxidation of an active agent that is in a reduced form. Accordingly, the present invention contemplates delivery devices that minimize of prevent contact of an active agent with oxygen during delivery to a subject.

In one embodiment, the present invention includes a drug delivery device, comprising:

a reservoir for containing a composition of the present invention, i.e., comprising a halogen compound or reduced form of a halogen compound, alone or in combination with one or more additional active agents, such as, e.g., a chalcogenide or a reduced form of a chalcogenide, such as a sulfide or selenide; and a fluid communicator, the fluid communicator configured to maintain at least 90% of the reduced form of active agent in the composition in reduced form during delivery to a subject. In particular embodiments, it is configured to maintain at least 95%, at least 96%, at least 97%, at least 98%, or at least 99% of the reduced form of active agent in reduced form during administration to a subject. In certain embodiments, the fluid communicator is in fluid communication with the reservoir. In other embodiments, it is can be placed into fluid communication with the reservoir.

In certain embodiments, the reservoir is oxygen impermeable, and/or it is formed of an oxygen impermeable polymer. In certain embodiments, the reservoir comprises an oxygen impermeable layer, e.g., at its inner surface, which may comprise: polyethylene (LDPE), polystyrene (PS), polyethylene (PE), polycarbonate (PC), polyvinyl acetate (PVAc), APET, polyvinly chloride (PVC), nylon 6 (Ny6), polyvinyl fluoride (PVF), polyvinylidene chloride (PVdC), polyacetonitrile (PAN), ethylene vinyl alcohol (EVOH), or Polyvinyl alcohol (PVA). In certain embodiments, the oxygen transmission coefficient of said polymer is less than $10^{-10}$ [cm$^3$(STP)/cm/(cm$^2$+s+Pa)]. In related embodiments, it is less than $10^{-9}$, less than $10^{-8}$, or less than $10^{-7}$ [cm$^3$(STP)/cm/(cm$^2$+s+Pa)]. In related embodiments, the reservoir includes multiple layers of oxygen impermeable polymers.

In particular embodiments, the reservoir includes a resealable port. A resealable port may be used for introducing a solution comprising a therapeutic agent, such as a reduced form of a halogen compound and/or a reduced form of a chalcogenide, into the reservoir. A resealable port may be used for coupling to the fluid communicator. In particular embodiments, the reservoir includes a plurality of resealable ports. In certain embodiments, the reservoir is a bottle, a bag, a tube, a vial, or a syringe. In particular embodiments, it is an intravenous bag or a syringe. In particular embodiments, it is a tubular member, the tubular member having a septum configured to hermetically seal the tubular member. In one embodiment, the tubular member is a Hungate tube.

In particular embodiments, the fluid communicator is configured to be fluidically coupled to the reservoir through a resealable port. In related embodiments, the fluid communicator is configured to intravenously deliver an active agent, e.g., a reduced form of a halogen compound and/or a reduced form of a chalcogenide, from the reservoir to a subject in need thereof. In certain embodiment, the fluid communicator includes at least one of a needle and a cannula.

In certain embodiments, the device, including the fluid communicator, is disposed in a reduced oxygen or oxygen-free environment. In particular embodiments, the reduced oxygen or oxygen-free environment is within a container, optionally wherein said container is a bag or a malleable container, e.g., that allows manipulation of components of the device through the bag, such as coupling of the fluid communicator to the reservoir in embodiments where they are not initially coupled. In particular embodiment, the container comprises one or more oxygen impermeable polymer, including any of those described above. In particular embodiments, the walls of the container comprise multiple layers of one or more oxygen impermeable polymers.

In particular embodiments, the device comprises in the reservoir a composition comprising a reduced form of a halogen compound and/or a chalcogenide. In certain embodiments, the reduced form of halogen compound is an iodide, e.g., sodium iodide, potassium iodide, or hydrogen iodide, and/or the reduced form a chalcogenide is H$_2$Se, Na$_2$Se or NaHSe or a sulfide compound.

In particular embodiments, the device allows for delivery of the reduced form of active agent, e.g., a reduced form of a halogen compound, such as iodide and/or a reduced form of a chalcogenide, such as selenide or sulfide, wherein at least 90%, at least 95%, at least 96%, at least 97%, at least 98%, or at least 99% of the active agent is delivered to the subject in reduced form.

The present invention further includes a method for reducing injury or treating a disease in a subject by providing to said subject a composition of the invention, wherein said composition is provided to said subject using the device of the present invention. In particular embodiments, the injury or disease is any of those described herein, including but not limited to an injury resulting from ischemia or reperfusion. In particular embodiments, the injury is an infarct caused by a heart attack or stroke, or chronic hear failure. In other embodiments, the injury is caused by inflammation. In certain embodiments, the composition comprising a halogen compound is provided to a subject using a device described herein. In certain embodiments wherein the composition comprising a halogen compound also comprises an additional therapeutic agent or wherein the composition comprising a halogen compound is provided in combination with a composition comprising an additional active agent, such as a reduced form of a chalcogenide, the composition comprising the halogen compound and/or the other composition are provided using a device described herein.

Further, the present invention also includes a method of delivering a composition comprising a reduced form of an active agent, wherein the composition comprises a halogen compound, to a patient in need thereof, the method comprising:

containing the composition comprising a reduced form of active agent in a reservoir, the reservoir configured to maintain the active agent in a reduced form;

establishing fluid communication between the reservoir and the subject;

delivering a predetermined volume of the composition from the reservoir to the subject in an environment substantially free of oxygen.

In particular embodiments, a device of the present invention comprises: (1) an i.v. bag comprising a composition of the present invention, wherein said i.v. bag is oxygen impermeable; and (2) a tubing, wherein said tubing is coupled at a first end of the tubing to the i.v. bag through a port in the i.v. bag, or wherein said tubing is capable of being coupled at a first end of the tubing to the i.v. bag through a port in the i.v. bag, wherein said tubing is coupled at a second end of the tubing to a needle or cannula, or wherein said tubing is capable of being coupled at a second end of the tubing to a needle or cannula, wherein said device is contained within a bag comprising a reduced oxygen or oxygen-free environment. In particular embodiments, the i.v. bag and/or the bag comprise one or more oxygen impermeable polymers described herein. In particular embodiments, the bag is flexible, such as to allow a user to couple the tubing to the i.v. bag and/or needle while the device remains sealed in the bag.

In particular embodiments, a device of the present invention comprises: (1) an i.v. bag comprising a composition of the present invention, wherein said i.v. bag is oxygen impermeable; and (2) a tubing, wherein said tubing is coupled at a first end of the tubing to the i.v. bag through a port in the i.v. bag, or wherein said tubing is capable of being coupled at a first end of the tubing to the i.v. bag through a port in the i.v. bag, wherein said tubing is coupled at a second end of the tubing to a needle or cannula, or wherein said tubing is capable of being coupled at a second end of the tubing to a needle or cannula, wherein said device is contained within a bag comprising a reduced oxygen or oxygen-free environment. In particular embodiments, the i.v. bag and/or the bag comprise one or more oxygen impermeable polymers described herein. In particular embodiments, the bag is flexible, such as to allow a user to couple the tubing to the i.v. bag and/or needle while the device remains sealed in the bag, and/to apply pressure to the i.v. bag to begin flow of the composition through the tubing towards or into the needle or cannula.

In particular embodiments, a device of the present invention comprises: (1) an syringe comprising a composition of the present invention, wherein said syringe is oxygen impermeable; and (2) a needle or cannula, wherein said needle or cannula is coupled to the syringe through a port in the syringe, or wherein said needle or cannula is capable of being coupled to the syringe through a port in the syringe, wherein said device is contained within a bag comprising a reduced oxygen or oxygen-free environment. In particular embodiments, the syringe and/or the bag comprise one or more oxygen impermeable polymers described herein. In particular embodiments, the bag is flexible, such as to allow a user to couple the needle or cannula to the syringe while the device remains sealed in the bag, and/to apply pressure on the syringe to begin flow of the stable composition into the needle or cannula.

In particular embodiments, the device comprises a therapeutically effective amount of an agent or composition of the present invention.

EXAMPLES

Example 1

Sodium Iodide Improves Myocardial Infarction Outcome

This example demonstrates that sodium iodide (NaI) improves outcome in a mouse model of heart attack by reducing infarct size.

Figure 1:
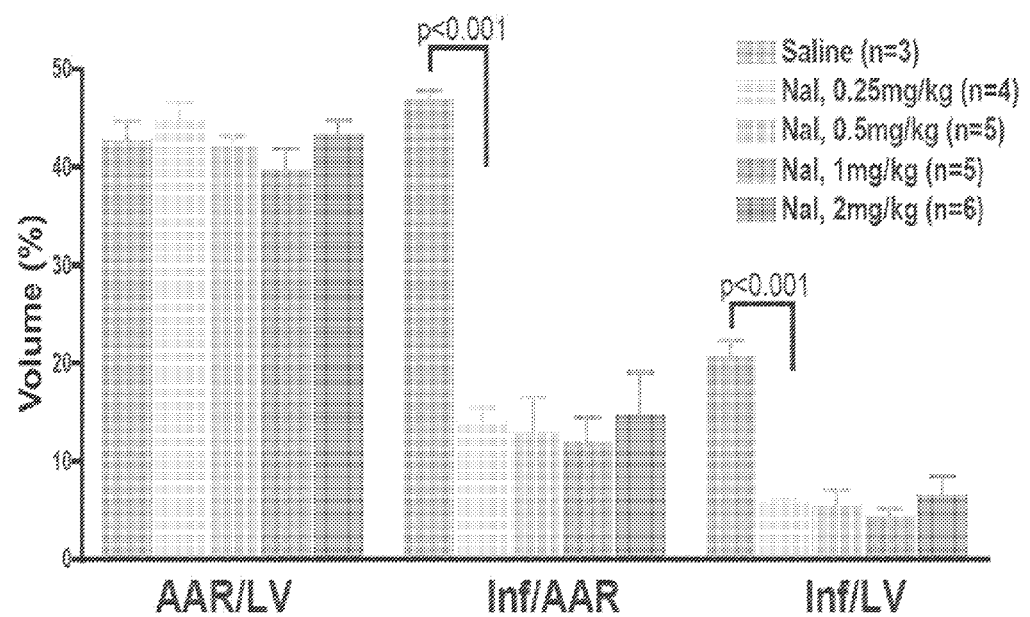
FIG. 1 provides a graph and table demonstrating NaI protection against infarct following ligation-induced ischemia. Ischemic conditions were induced in mice via open chest ligation of the left descending coronary artery. In the graph, the Inf/AAR and Inf/LV bars represent morphometric analysis of the infarct size (Inf) in relation to the total size of the area at risk (AAR) or left ventricle (LV), respectively, in the presence of saline control or increasing amounts of NaI (as indicated). The AAR/LV bars shows the ratio of the size of the area at risk to the size of the left ventricle in the presence of saline control or increasing amounts of NaI (as indicated), and demonstrates that similar sampling was performed on all test subjects. For each of the sets of bars for Inf/AAR, Inf/LV and AAR/LV, the bars from left to right correspond to the bars from top to bottom shown in the legend. The table beneath the graph provides the mean volume (%) and standard error for each data point.

In order to examine the effect of NaI on myocardial infarct size in a mouse model of heart attack, open chest ligation of the left descending coronary artery (LAD ligation) was performed in mice. At 55 minutes post initiation of ischemia, either vehicle (saline) or test agent (NaI) was injected into the femoral vein of each mouse. The heart muscle was reperfused by releasing the ligature at 60 minutes post initiation of ischemia. After 2 hours of reperfusion, infarct size was measured by morphometry (FIG. 1). Five groups of mice were utilized in this study, including a saline vehicle group (n=3) and five test groups that received 0.25 mg/kg (n=4), 0.5 mg/kg (n=5), 1 mg/kg (n=5), or 2 mg/kg (n=6) of NaI. To be certain that all animals in the study were treated in a similar way, the area at risk (AAR) as a proportion of the left ventricle was determined (FIG. 1). Area at risk (AAR) and infarct size (Inf) were measured using the specific dyes TTC and Evans blue. Processed images were generated in an unbiased way by setting constant thresholds and allowing Photoshop® to generate the images that were quantitated to generate the data presented in FIG. 1.

These results show that there were statistically significant decreases in infarct size when comparing the saline group to all four test groups that received NaI (FIG. 1). For each dosage tested, treatment with NaI resulted in an approximately 70% reduction in infarct size in comparison to vehicle alone.

Figure 2:
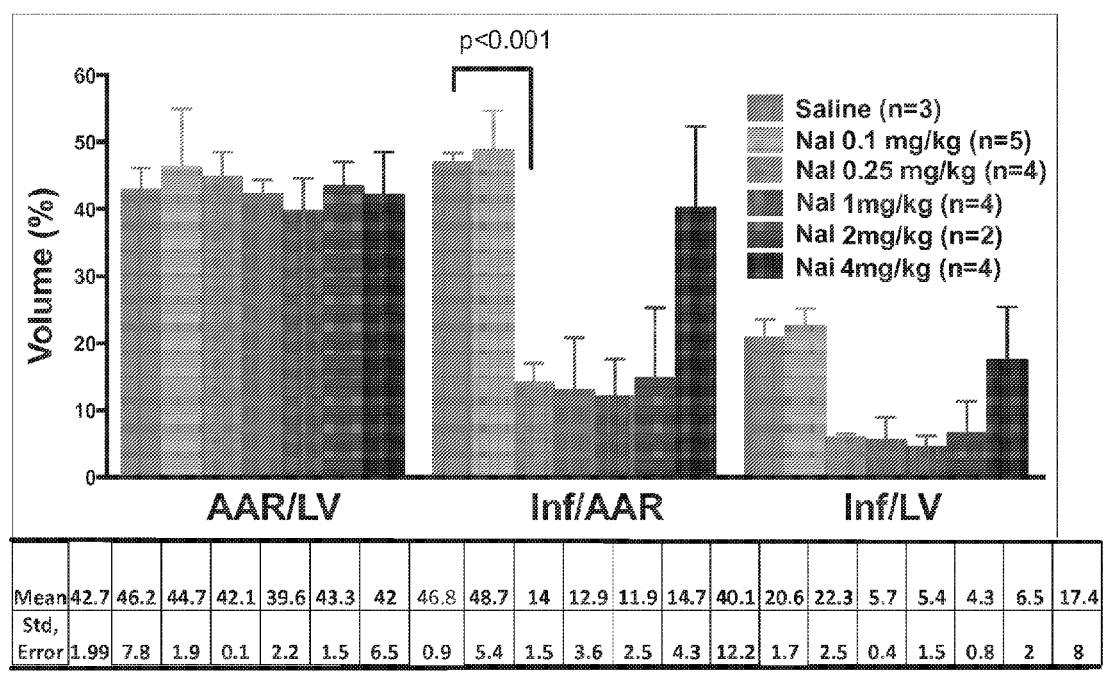
FIG. 2 provides a graph and table demonstrating NaI protection against infarct following ligation-induced ischemia. Ischemic conditions were induced in mice via open chest ligation of the left descending coronary artery. In the graph, the Inf/AAR and Inf/LV bars represent morphometric analysis of the infarct size (Inf) in relation to the total size of the area at risk (AAR) or left ventricle (LV), respectively, in the presence of saline control or increasing amounts of NaI (as indicated). The AAR/LV bars shows the ratio of the size of the area at risk to the size of the left ventricle in the presence of saline control or increasing amounts of NaI (mg/kg), and demonstrates that similar sampling was performed on all test subjects. For each of the sets of bars for Inf/AAR, Inf/LV and AAR/LV, the bars from left to right correspond to the bars from top to bottom shown in the legend. The table beneath the graph provides the mean volume (%) and standard error for each data point.

An additional test was performed under the same conditions but using an expanded range of concentration of NaI. The results of this test also show that there were statistically significant decreases in infarct size when comparing the saline group to all four test groups that received NaI (FIG. 2).

To determine whether pretreatment with NaI prior to heart attack improves heart attack outcome, open chest ligation experiments were performed in mice where either vehicle (saline) or test agent (NaI) was injected into the femoral vein of each mouse either 5 minutes or 48 hours before initiation of ischemia. Open chest ligation of the left descending coronary artery (LAD ligation) was then performed, and the heart muscle was reperfused by releasing the ligature at 60 minutes post initiation of ischemia. After 2 hours of reperfusion, infarct size was measured by morphometry as described above (FIG. 3). Three groups of mice were utilized in this study, including a saline vehicle group (n=1) and two test groups that received 1 mg/kg NaI 5 minutes before LAD ligation (n=4) or 1 mg/kg NaI 48 hours before LAD ligation (n=1).

Figure 3:
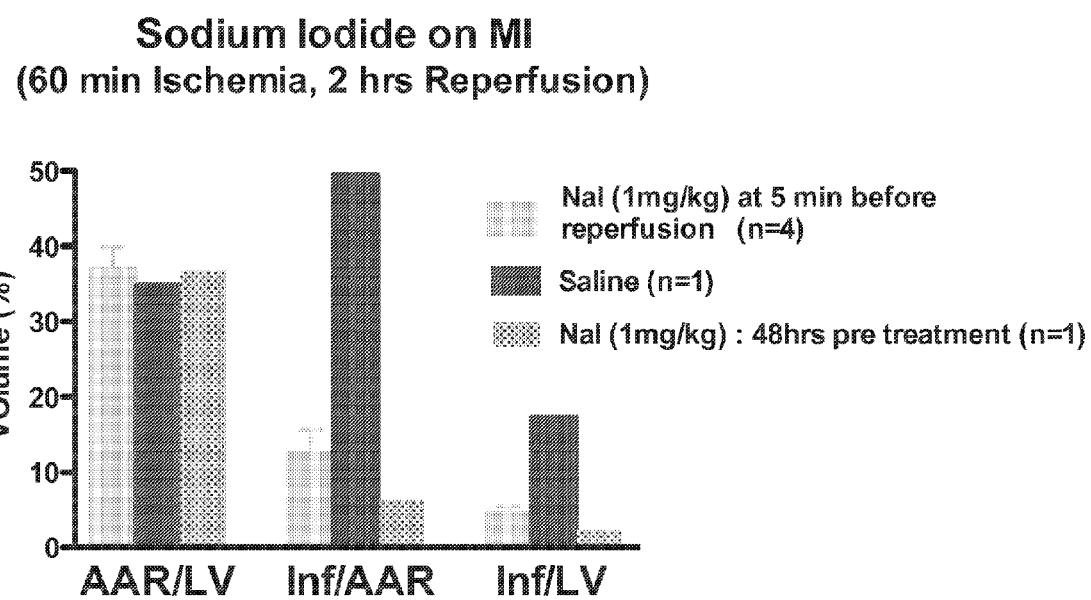
FIG. 3 provides a graph demonstrating protection from infarct by prophylactic treatment with NaI 5 minutes or 48 hours prior to ligation-induced ischemia. Subjects were injected with either saline or NaI (1 mg/kg) 5 minutes or 48 hours prior to the induction of ischemia by open chest ligation of the left descending coronary artery. After 60 min of ischemic conditions, ligatures were released to induce reperfusion, and infarct size was measured and reported in relation to the total size of the area at risk (AAR) and left ventricle (LV). For each of the sets of bars for Inf/AAR, Inf/LV and AAR/LV, the bars from left to right correspond to the bars from top to bottom shown in the legend. The table beneath the graph provides the mean volume (%) and standard error for each data point.

These results show that there were statistically significant decreases in infarct size when comparing the saline group to both test groups that received NaI (FIG. 3). For each dosage tested, pre-treatment with NaI resulted in an approximately 70% reduction in infarct size in comparison to vehicle alone.

Figure 4:
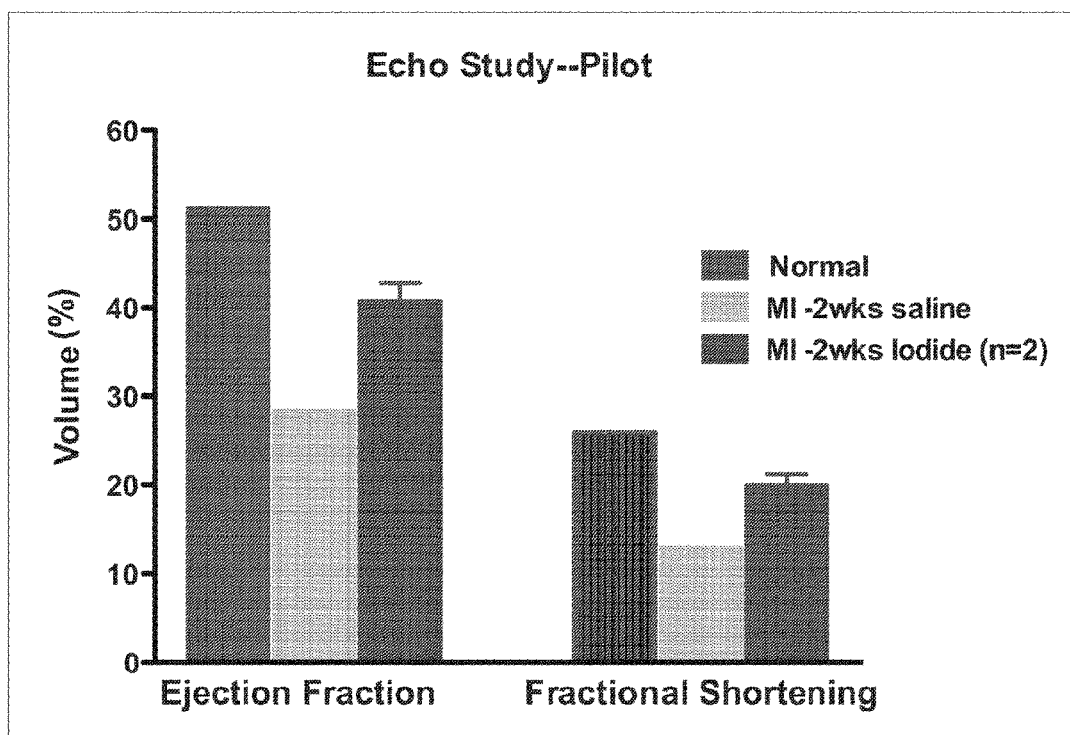
FIG. 4 provides a graph demonstrating protection from infarct by prophylactic treatment with NaI by a single intravenous administration two days prior to ligation-induced ischemia as determined by echocardiogram. The graph shows the mean volume (%) for ejection fraction and fractional shortening in normal animals (no infarct induced), and animals treated with saline as control or with NaI. For each of the sets of bars for Ejection Fraction and Fractional Shortening, the bars from left to right correspond to the bars from top to bottom shown in the legend.

In addition, the protective effect of NAI was confirmed by echocardiography, as shown in FIG. 4. In vivo transthoracic echocardiography of the left ventricle (LV) using a 30-MHz RMV scanhead interfaced with a Vevo 770 (Visualsonics) was performed, and two-dimensional echocardiography images were obtained. LV end-diastolic diameter (EDD) and LV end-systolic diameter (ESD) were measured at a day before for a baseline and one and 4 weeks after myocardial ischemia and reperfusion. LV percent fractional shortening (FS) and LV ejection fraction (EF) were calculated.

Example 2

Glutathione Stabilizes Selenide

Figure 5:
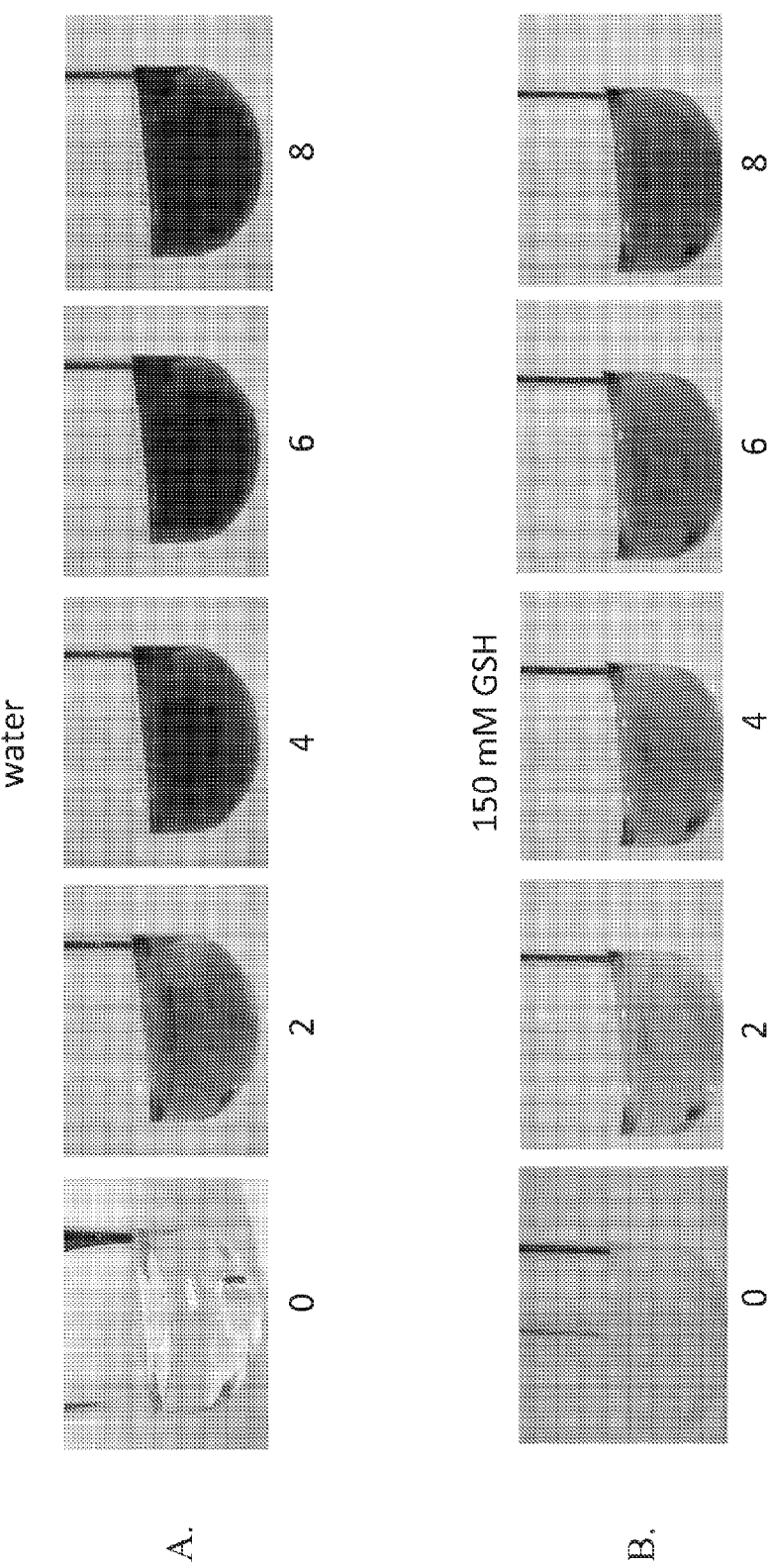
FIG. 5 provides photographs demonstrating that glutathione prevents selenide from oxidation. The photographs show samples of 50 mM selenide in either water (FIG. 5A)

To demonstrate that glutathione prevents selenide from oxidation, solutions of 50 mM selenide were prepared in either water or 150 mM GSH and observed for the 8 minutes immediately following preparation. In FIG. 5, the oxidized forms of selenide appear dark in the solutions, with the samples in glutathione clearly showing reduced levels of oxidation at each time point.

Example 3

Immunosuppressant Properties of Halogen Compounds and Chalcogenides

To demonstrate the immunosuppressant properties of iodide and selenide, blood was obtained from two donors (A and B), and peripheral blood mononuclear cells (PBMC) were purified from the blood. PBMC were either irradiated with 3500 rads (Ax and Bx) or not (A and B). Irradiated and unirradiated PBMC from each patient were mixed (100,000 from each) and placed into culture medium containing various amounts of cyclosporin A (CSA, positive control), iodide (Iod), selenide (Sel), or just the media for 5 days. The specific amounts of each compound are shown in FIG. 6. Following this incubation, the cells were pulsed with tritiated thymidine for 18 hours to determine the amount of DNA synthesis. Cells were lysed, the lysate filtered to trap the DNA on the filter and the filters counted in a scintillation counter. The amounts of incorporated tritium were recorded and are shown in FIG. 7. PBMC from donor A not mixed with others cells or mixed with irradiated PBMC from donor A served as negative controls; likewise for donor B. The positive control was PBMC from A mixed with Bx or visa versa. All concentrations of selenide reduced the labeling to control levels. Iodide at the highest concentration reduced the amount of labeling. Others have shown that the degree of labeling is directly correlated with the degree of T cell activation. Low levels of labeling correlate with immunosuppression. These experiments demonstrate that selenide and iodide have immunosuppressant effects.

Example 4

Sodium Iodide Improves Myocardial Infarct Outcome

This example demonstrates that treatment with sodium iodide (NaI) in drinking water for two days prior to induced infarct improves outcome in a mouse model of heart attack.

In order to examine the effect of pre-treatment with drinking water containing NaI on myocardial infarct size in a mouse model of heart attack, three groups of mice were provided with drinking water containing various concentrations of iodide to achieve dosages of 0.07 mg/kg/day (normal drinking water) for the first group; 0.77 mg/kg/day for the second group; or 7.07 mg/kg/day for the third group, for two days immediately prior to open chest ligation of the left descending coronary artery (LAD ligation) to initiate ischemia. A fourth group of mice was provided with normal drinking water for the two days prior to the initiation of ischemia, but at 55 minutes post initiation of ischemia, either vehicle (saline) or test agent (NaI) was injected into the femoral vein of each of these mice. The heart muscles of the mice were then reperfused by releasing the ligatures at 60 minutes post initiation of ischemia. After two hours of reperfusion, infarct size was measured by morphometry (FIG. 1). To be certain that all animals in the study were treated in a similar way, the area at risk (AAR) as a proportion of the left ventricle was determined (FIG. 8). Area at risk (AAR) and infarct size (Inf) were measured using the specific dyes TTC and Evans blue. Processed images were generated in an unbiased way by setting constant thresholds and allowing Photoshop® to generate the images that were quantitated to generate the data presented in FIG. 8.

These results show that there were statistically significant decreases in infarct size when comparing the group pre-treated with normal water to the groups pre-treated with water containing higher concentrations of iodide (FIG. 8). These decreases were somewhat less or comparable to those observed in mice intravenously administered iodide at the time of reperfusion.

Example 5

Sodium Iodide Improves Chronic Heart Failure

This example demonstrates that treatment with sodium iodide (NaI) improves outcome in a mouse model of chronic heart failure.

In order to examine the effect of drinking water containing NaI on chronic heart failure following heart attack in a mouse model, two groups of mice were provided with drinking water lacking iodide or drinking water containing 0.77 mg/kg/day iodide starting immediately following open chest ligation of the left descending coronary artery (LAD ligation) to initiate ischemia, and continuing until the end of the study, which lasted 12 weeks. Prior to the LAD ligation and at 1 week, 2 weeks, 4 weeks, 8 weeks, and 12 weeks following the LAD ligation, mice were examined by echocardiography to determine their left ventricle ejection fraction and their left ventricle fractional shortening. The results are shown in FIG. 9. This study was repeated as described above with more mice, and the combined results of both studies are shown in FIG. 10.

These results show that there were statistically significant increases in left ventricle ejection fraction reduction and left ventricle fractional shortening in the group treated with water containing 0.77 mg/kg/day iodide as compared to the group treated with normal drinking water (FIG. 9). These results demonstrate that treatment may be used to treat or prevent chronic heart failure, including chronic heart failure following myocardial infarct.

Example 6

Sodium Iodide is Efficacious in the Treatment of Acute Myocardial Infarction This study demonstrates the efficacy of sodium iodide, administered at 1 mg/kg as an i.v. bolus, in a rat model of acute myocardial infarction (AMI) by comparing 4 and 24 hr plasma cardiac troponin I (cTpnI) values and myocardial infarct sizes at 24 hrs between a placebo cohort receiving saline only and subject to 30 min ischemia, an ischemic preconditioned cohort (5 min ischemia/5 min reperfusion, 3×) subject to 30 min of ischemia, and a treatment cohort receiving 1 mg/kg NaI as an i.v. bolus and subject to 30 min of ischemia.

Methods

Male CD® IGS Rats (300-450 g) were subjected to 30 minutes of LAD occlusion followed by 24-30 hrs of reperfusion. 200-400 uL of blood was drawn at 4 and 24-30 hrs post-reperfusion for plasma cTpnI measurements by EIA. After the 24-30 hr blood draw, the LAD was re-occluded, and the heart was excised following i.v. administration of Evans Blue. The hearts were frozen overnight, sectioned, and stained with triphenyl tetrazolium chloride for subsequent blinded infarct analysis.

Animal Preparation and Surgery

Rats were anesthetized with a ketamine/xylazine mixture (100 mg/kg and 10 mg/kg, respectively) and maintained under 2-3% isoflurane in 100% medical oxygen after intubation with a 16 gauge angiocatheter sheath (Terumo® Surflo i.v. catheter, 16 G×2", VWR Cat.# TESR-OX1651CA). Animals were ventilated using a Harvard Apparatus Model 683 small animal ventilator equipped with a 5 cc cylinder at a tidal volume of 1.5-2.0 mL/stroke and a respiratory rate of 105 strokes/min. With the rat lying on its right side, animal fur was removed from the surgical area with clippers and then cleaned with alcohol pads. The heart beat was visualized through the chest wall and a dorsoventral incision in the left chest wall was made directly over the beating heart. The underlying fascia was dissected away to reveal the ribs and intercostal muscles. A left thoracotomy was then performed in the $4^{th}$ intercostal space and the ribs were separated using alm retractors (Fine Science Tools Cat. #17008-07). The pericardium was then carefully opened and used to keep the lungs and thymus out of the surgical field. The left anterior descending coronary artery was visualized, and a 5-0 prolene suture with an RB-2 tapered needle (Ethicon Cat. #8710H) was passed underneath twice at the boundary of the left atrial appendage to completely encircle the artery. The ends of the suture were passed through a 1 cm length of PU-50 tubing, and ischemia was induced by tightening the suture against the tubing and securing in place with hemostats. Ischemia was verified by visual confirmation of cyanosis and akinesis in the left ventricular wall. Reperfusion was achieved by removing the hemostats and raising the tubing off of the ventricular wall, thereby loosening the suture around the LAD. Reperfusion was confirmed by visualizing the reversal of cyanosis in the ventricular wall. The suture around the LAD was left in place, and the chest was then closed by re-approximating the edges of the ribs and stitching the musculature with a continuous 5-0 silk suture. As the last suture was being placed, the lungs were transiently overinflated by obstructing the expiratory limb of the respirator for 3-4 cycles to expel air from the chest cavity. The suture was then tightened to seal the thoracic cavity, the facia over the ribs and intercostal muscles was sutured closed with 5-0 silk, and the skin was then sutured closed with 5-0 silk. The anesthesia was then turned off, and the animal was removed from the ventilator once spontaneous breathing resumed. The endotracheal tube was removed once the animal regained consciousness. Over the course of the entire surgical procedure, the animals were on a heated, circulating water pad and under a heat lamp to maintain core body temperature. After recovery, all animals remained in cages under heat lamps until the 4 hr blood draw, at which point they were placed back in the animal housing facility.

Plasma Sample Prep and cTpnI EIA

Under isoflurane anesthesia (3% for induction, 2% for maintenance), 4 hr blood draws were collected (by tail bleed for naïve and from carotid artery catheter for pre-cathed animals) into heparinized microtainer plasma separator tubes (VWR Cat. #VT365985) while 24-30 hr draws were collected from either a carotid artery catheter (pre-cathed from Charles River) or a jugular vein catheter (implanted in naïve animals prior to opening the chest wall and reoccluding the LAD). Blood was centrifuged at 10,000+ rpm for 5 min, and plasma was transferred to 0.5 mL microfuge tube and stored at −20° C.

Cardiac troponin I was measured in a total of 51 plasma samples (26 4 hr samples and 25 24-30 hr samples) which were run at 1:50 dilutions in a Rat Cardiac Troponin-I, High Sensitivity ELISA (Kamiya Biomedical Company Cat. #KT-639) according to the manufacturer's instructions.

Morphometric Analysis

After 24 hr blood draws, the chest wall was reopened through the previous day's incision, and the LAD was re-occluded using the prolene suture left in place around the LAD the prior day. Once ischemia was observed visually, a 10% Evans Blue solution was administered i.v. (via carotid or jugular cannula) until the perfused area of the heart turned blue, and then the heart was excised from the thoracic cavity. Atria, valves, large vessels, and right ventricle were trimmed away after thorough rinsing in water, and the left ventricle was then rinsed briefly again with water, wrapped in cellophane, and frozen overnight at −20° C. The left ventricle was then sliced into six 2 mm thick slices and incubated in 1.5 mL 1% TTC in PBS for 20 min. at 37° C. Images of the apical and basal surfaces of each slice were then obtained on a Nikon DSL 3200 equipped with a macro lens. Infarct analysis was blinded with respect to treatment.

Results

Plasma troponin levels were consistently lower in animals treated with sodium iodide than those treated with placebo (FIG. 10). In addition, infarcts were smaller in animals treated with sodium iodide as compared to those treated with placebo (FIG. 11), whereas infarcts in the ischemic preconditioning cohort showed onlyu nonsignificant trends in reduced size as compared to placebo. These data demonstrate that administration of iodide is effective in treating AMI.

Example 7

Treatment of Human Disease with Elemental Reducing Agents

A variety of human diseases are associated with the formation of reactive oxygen species that cause lipid peroxidation and protein carbonylation, including those diseases shown in the previous examples to benefit from treatment with iodide (or sulfide or selenide). These chemical modifications of biopolymers play a causal role in the loss of cells resulting in disease and death. Accordingly, other diseases associated with the formation of reactive oxygen species may also be treated using iodide or another elemental reducing agent (ERA), including any of those described herein, e.g., sulfide or selenide. The following diseases are tested in animal or ex vivo models of human disease to demonstrate the outcomes expected when the animals or tissues are treated with iodide or another ERA such as sulfide or selenide. All studies include intravenous treatment with ERAs.

Renal Transplant

Kidneys are removed from dogs and pigs, stored for 24 hours and then transplanted into an animal in which they lack a second kidney and, therefore, are dependent on the function of the transplanted kidney. ERAs, e.g., iodide, sulfide, and selenide, are expected to increase the functionality of the stored kidney, establishing that ERAs can be used to improve human kidney transplantation.

Graft Vs. Host Disease

Mice and dogs are irradiated to destroy bone marrow stem cells (BMSC), and unmatched donor BMSC are transplanted into the irradiated animals in the absence of cyclosporine A treatment. It is expected that ERAs, e.g., iodide, sulfide and selenide, will function as cyclosporine and enable unrelated marrow to engraft without graft rejection and loss of life.

Peripheral Vascular Disease

Mice are surgerized to prevent femoral blood flow to the hind limb. Treatment with an ERA, e.g., iodide, sulfide or selenide, twice daily for 2 weeks following surgery is expected to permanently improve blood flow.

Noise-Induced Hearing Loss

Mice are exposed to loud noise and then intravenously treated with an ERA, such as iodide, selenide or sulfide. It is expected that treatment with the ERA will improve outcome compared to untreated control animals, i.e., resulting in decreased hearing loss.

Acute Ischemic Stroke

Rats exposed to temporary loss of blood flow to the brain are reperfused at the same time they are treated with an ERA, such as iodide, sulfide or selenide. It is expected that treatment with the ERA will reduce tissue damage caused by the loss of blood flow, and reduce ischemic-reperfusion infury.

Acute Myocardial Infarction

The left anterior descending coronary artery of animals (mice, rats and rabbits) is ligated temporarily to mimic a heart attack. At the point of reperfusion, an ERA such as iodide, sulfide or selenide is infused. This treatment decreases heart damage and improves heart function.

Contrast-Induced Nephropathy

Mice are treated with a contrast agent under conditions that induce kidney injury to model the type of injury frequently suffered by patients that are exposed to an intravenous contrast agent in the course of vascular imaging. It is expected that treatment with an ERA, e.g., iodide, sulfide or selenide, will reduce damage and improve kidney function.

Sickle Cell Anemia

Mice bearing specific mutant hemoglobin suffer similar red cell hemolysis and vascular damage found in patients with sickle cell anemia. Damage in these mice is exacerbated by acute hypoxic exposure. These mice will be treated with an ERA such as sulfide, selenide or iodide in the presence or absence of acute hypoxic exposure, and it is expected that treatment with the ERA will protect them from this damage.

Postoperative Ileus

Pertioneal surgery is associated with extended recovery owing to a period in which there is a lack of intestinal peristalsis. Such a lack of peristalsis is induced in mice, and the mice are then treated with an ERA, e.g., iodide, sulfide or selenide. It is expected that the ERA will shorten/eliminate this lack of peristalsis following surgery.

Radiation Induced Lung Injury

Radiation treatment in the course of cancer therapy sometimes results in unintended lung injury. Mice are irradiated to generate lung injury. An ERA, e.g., iodide, sulfide or selenide, is administered to the mice prior to and following irradiation. It is expected that treatment with the ERA will decrease lung injury.

Ventilator Induced Lung Injury

Lung ventilation is of great value for some patients; however, ventilation can damage the lung. Mice are exposed to ventilation injury with or without treatment with an ERA such as iodide, sulfide or selenide. It is expected that ERA treatment will decrease lung injury.

*Salmonella* Infection

Bacterial infection with *Salmonella* can be lethal. Mice are infected with *Salmonella* and treated with an ERA, e.g., iodide, sulfide or selenide. It is expected that the ERA will suppress immune and inflammatory responses, thereby improving survival.

Retinopathy

Loss of cells in the retina is thought to come about from reactive oxygen species. ERAs are anti-oxidants. Rats are treated with conditions that cause retinopathy modeling human retinal degeneration and treated with an ERA such as iodide, sulfide or selenide. It is expected that treatment with the ERA will improve retinal cell viability Organ Preservation Organ transplantation involves temporary loss of blood flow. Explanted organs from donor pigs are perfused ex vivo with an ERA, e.g., iodide, sulfide or selenide, in preservation solution before being transplanted into a recipient pig. It is expected that treatment with the ERA will improve the functioning of the organ once it is transplanted into the recipient.

Hypoxia-Ischemia Encephalopathy

Temporary loss of blood flow, followed by reperfusion can result in permanent brain damage. Newborn ferrets are treated with an ERA, e.g., iodide, sulfide or selenide, under conditions that mimic this brain damage. It is expected that treatment with the ERA at birth will decrease brain damage.

Epilepsy

Epilepsy is associated with seizures causing excessive metabolic activity in the brain and damage. ERA treatment decreases metabolic rate. Rats are treated with an ERA, e.g., iodide, sulfide or selenide, under conditions that model epileptic seizures and brain damage. It is expected that ERA treatment of rats suffering seizures will decrease brain damage.

Stem Cell Engraftment

Transplantation of stem cells results in oxidative damage and loss of many of the cells. Cardiomyocytes are transplanted into damaged rat hearts, and the cells and animals are either treated with an ERA, e.g., iodide, sulfide or sulfide, or left untreated. It is expected that treatment of the stem cells and the recipient animals with an ERA will improve stem cell engraftment.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

We claim:

1. A method for treating or inhibiting a reperfusion injury resulting from restoration of blood flow to an ischemic tissue or organ in a subject, comprising providing to said subject a pharmaceutical composition comprising sodium iodide and a pharmaceutically acceptable carrier, diluent, or excipient, wherein said composition is provided to the subject in an amount sufficient to increase the blood concentration of iodide in the subject by at least 500% for at least some time.

2. The method of claim 1, wherein said composition is provided to the subject parenterally.

3. The method of claim 2, wherein said composition is provided to the subject intravenously.

4. The method of claim 1, wherein said reperfusion injury occurs following percutaneous coronary intervention or thrombolysis.

5. The method of claim 1, wherein the subject is provided with the pharmaceutical composition daily, twice daily, or once every two days.

6. The method of claim 5, wherein the subject is provided with a dose of about 0.1 mg/kg to about 5 mg/kg of the sodium iodide.

7. The method of claim 6, wherein the subject is provided with a dose of about 0.5 mg/kg to about 2 mg/kg of the sodium iodide.

8. The method of claim 7, wherein the subject is provided with a dose of about 1.0 mg/kg of the sodium iodide.

* * * * *